(12) United States Patent
Kilgard

(10) Patent No.: US 11,344,727 B2
(45) Date of Patent: May 31, 2022

(54) STEREOGNOSIS TRAINING SYSTEM AND METHOD FOR PATIENTS WITH CHRONIC STROKE, SPINAL CORD INJURY OR NEUROPATHY

(71) Applicant: Board of Regents, The University of Texas System, Austin, TX (US)

(72) Inventor: Michael P. Kilgard, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 262 days.

(21) Appl. No.: 16/681,575

(22) Filed: Nov. 12, 2019

(65) Prior Publication Data

US 2020/0215329 A1 Jul. 9, 2020

Related U.S. Application Data

(60) Provisional application No. 62/855,648, filed on May 31, 2019, provisional application No. 62/758,047, filed on Nov. 9, 2018.

(51) Int. Cl.
| | |
|---|---|
| *A61N 1/36* | (2006.01) |
| *A61N 1/372* | (2006.01) |
| *G09B 19/00* | (2006.01) |
| *A61B 5/11* | (2006.01) |
| *A61B 5/00* | (2006.01) |

(52) U.S. Cl.
CPC ..... *A61N 1/36103* (2013.01); *A61N 1/36053* (2013.01); *A61N 1/36139* (2013.01); *A61N 1/37211* (2013.01); *G09B 19/003* (2013.01); *A61B 5/0077* (2013.01); *A61B 5/1128* (2013.01)

(58) Field of Classification Search
None
See application file for complete search history.

(56) References Cited

U.S. PATENT DOCUMENTS

| | | | |
|---|---|---|---|
| 6,398,222 | B1 | 6/2002 | Everett |
| 8,489,185 | B2 | 7/2013 | Kilgard et al. |
| 8,666,501 | B2 | 3/2014 | Kilgard et al. |
| 8,700,145 | B2 | 4/2014 | Kilgard et al. |
| 8,934,967 | B2 | 1/2015 | Kilgard et al. |
| 9,014,614 | B2 | 4/2015 | Roots et al. |

(Continued)

OTHER PUBLICATIONS

Adkins, et al. TSBVI White paper online: "The Development of Tactile Skills" See http://www.tsbvi.edu/instructional-resources?id=5263, last accessed Sep. 21, 2018.

(Continued)

*Primary Examiner* — Ankit D Tejani
(74) *Attorney, Agent, or Firm* — Schultz & Associates, P.C.

(57) ABSTRACT

Provided is an effective stereognosis training system that integrates hardware and software to provide a simple, reliable, quantitative system to provide tactile rehabilitation and progress monitoring. The system can include an interactive device including a novel set of objects, that are combined with neuromodulatory systems such as wireless closed-loop vagus nerve stimulation to improve neural plasticity and expedite functional recovery. The system can send updates to therapists or clinicians to monitor progress and encourage compliance with prescribed therapy.

13 Claims, 33 Drawing Sheets

(56) References Cited

U.S. PATENT DOCUMENTS

| | | |
|---|---|---|
| 9,084,565 B2 | 7/2015 | Mason et al. |
| 9,089,703 B2 | 7/2015 | Rodriguez et al. |
| 9,089,707 B2 | 7/2015 | Kilgard et al. |
| 9,204,998 B2 | 12/2015 | Kilgard et al. |
| 9,265,660 B2 | 2/2016 | Kilgard et al. |
| 9,265,661 B2 | 2/2016 | Kilgard et al. |
| 9,265,662 B2 | 2/2016 | Kilgard et al. |
| 9,265,663 B2 | 2/2016 | Kilgard et al. |
| 9,272,145 B2 | 3/2016 | Kilgard et al. |
| 9,339,654 B2 | 5/2016 | Kilgard et al. |
| 9,345,886 B2 | 5/2016 | Kilgard et al. |
| 9,460,266 B2 | 10/2016 | Einav et al. |
| 9,474,904 B2 | 10/2016 | Kilgard et al. |
| 9,504,831 B2 | 11/2016 | Kilgard et al. |
| 9,522,085 B2 | 12/2016 | Kilgard et al. |
| 9,522,272 B2 | 12/2016 | Kilgard et al. |
| 9,522,273 B2 | 12/2016 | Kilgard et al. |
| 9,522,274 B2 | 12/2016 | Kilgard et al. |
| 9,533,152 B2 | 1/2017 | Kilgard et al. |
| 10,029,094 B2 | 7/2018 | Kilgard et al. |
| 10,213,577 B2 | 2/2019 | Rodriguez et al. |
| 10,850,160 B2 | 12/2020 | Friedman et al. |
| 2005/0228240 A1* | 10/2005 | Williams ............... A61B 5/00 600/300 |
| 2007/0057457 A1 | 3/2007 | Hoffman |
| 2012/0323084 A1 | 12/2012 | Frost et al. |
| 2016/0023046 A1 | 1/2016 | Evin et al. |
| 2016/0279417 A1 | 9/2016 | Kilgard et al. |
| 2018/0085578 A1 | 3/2018 | Rennaker et al. |
| 2018/0221666 A1 | 8/2018 | Rennaker et al. |

OTHER PUBLICATIONS

Moldovan et al., IEEE International Conference on E-Health and Bioengineering—EHB 2017, p. 325, "Virtual Rehabilitation Programme Using the MIRA Platform, Kinect and Leap Motion Sensors in an 81 Years Old Patient with Ischemic Stroke". (Jun. 2017).

Kilgard, et al. "Vagus nerve stimulation paired with tactile training improved sensory function in a chronic stroke patient". NeuroRehabilitation 42 (2018) 159-169 (Mar. 12, 2018).

* cited by examiner

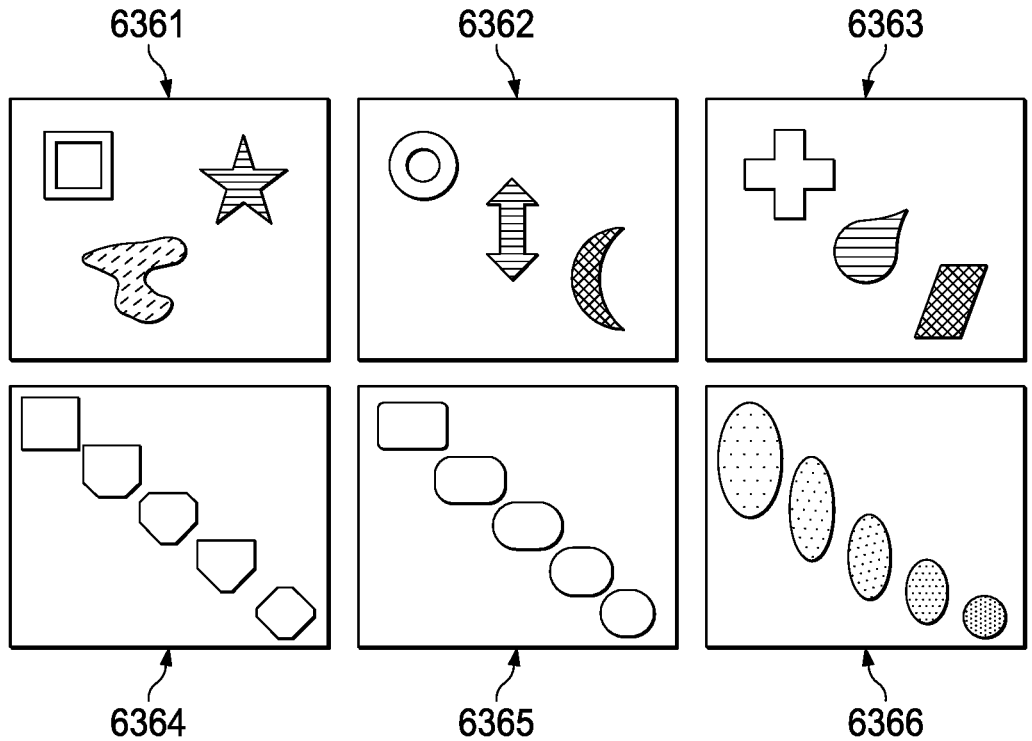
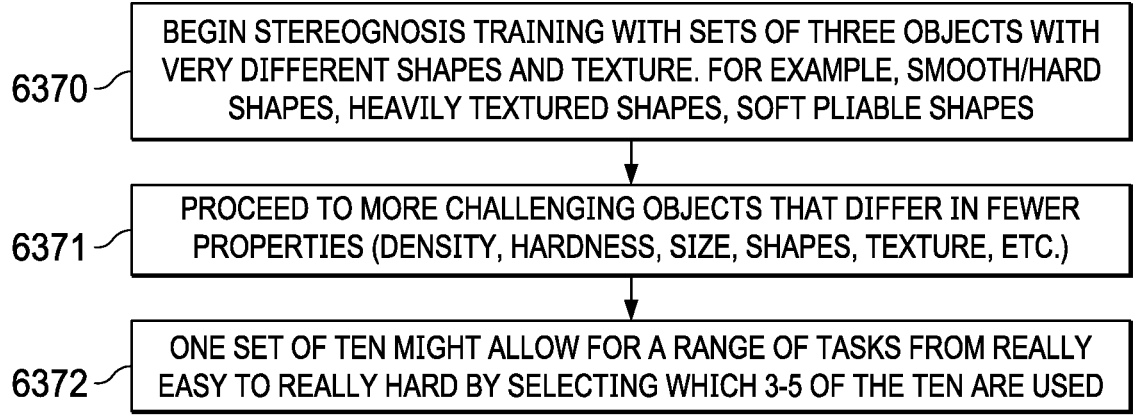
FIG. 6G

| 805 BASIC OBJECT | 806 TYPE | 807 EASY | 808 MEDIUM | 809 HARD | 810 RANGE | 827 SOMATOSENSORY RECEPTOR |
|---|---|---|---|---|---|---|
| 801 | LENGTH | 811 — 2", 4" | 812 — 2", 3", 4" | 813 — 2.5", 3", 3.5" | 814 — 2-4 in | 828 MECHANORECEPTOR RUFFINI ENDINGS |
| 802 | TEXTURE | 815 | 816 | 817 | 824 — 0-0.09 cm² (FEATURE) | 829 MECHANORECEPTOR MEISSNER CORPUSCLES |
| 803 | SHAPE | 818 | 819 | 823 | 825 — 0-6 POINTS | 830 MECHANORECEPTOR MERKEL'S DISKS |
| 804 | WEIGHT | 821 — 42, 85 g | 822 — 42, 64, 85 g | 820 — 53, 64, 74 g | 826 — 42-85 g | 831 PROPRIOCEPTOR |

FIG. 8A

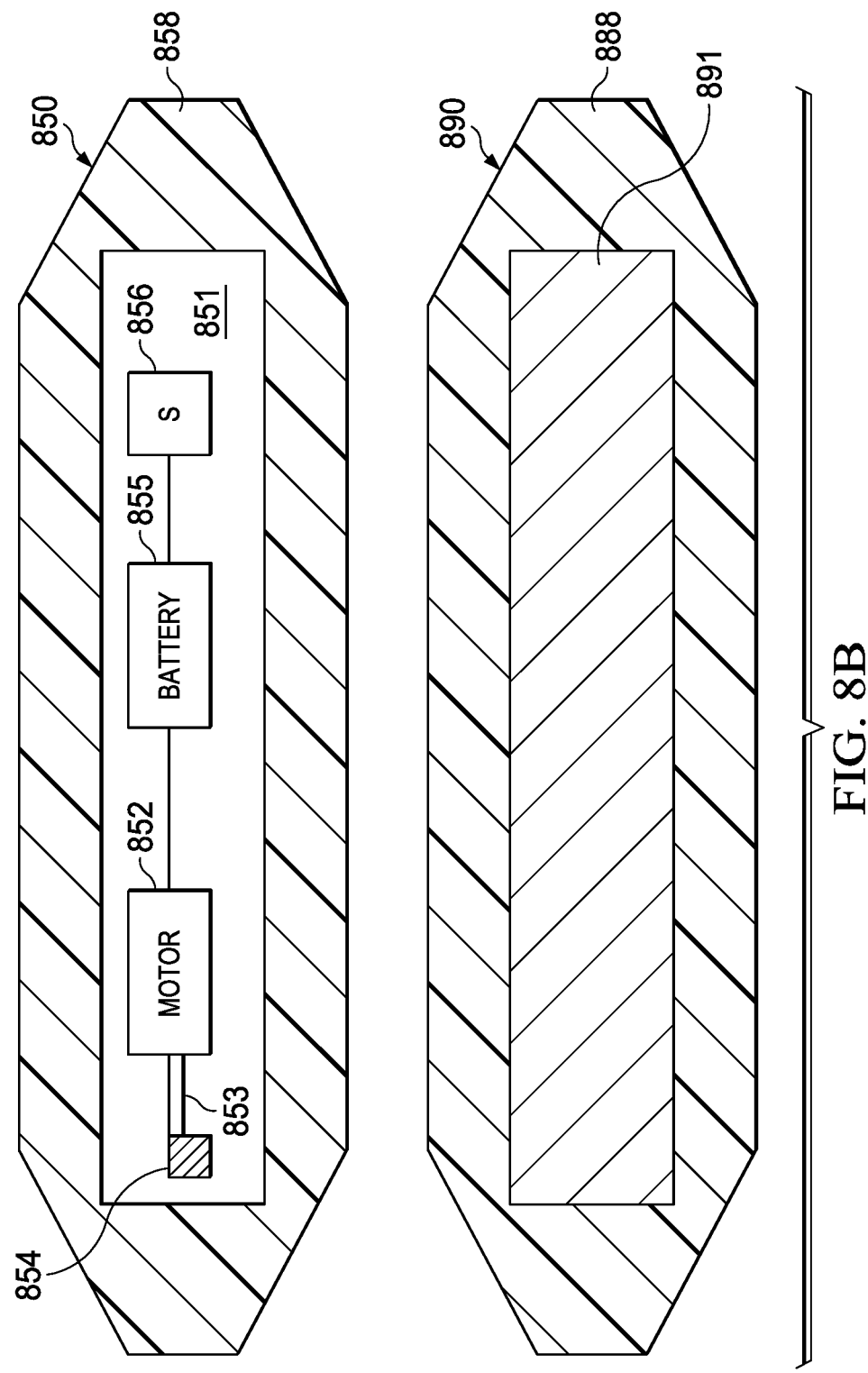

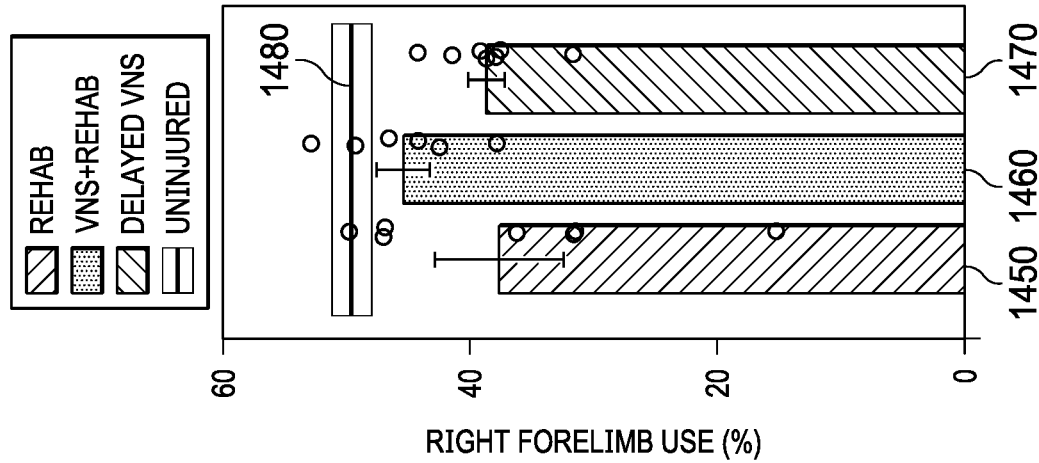
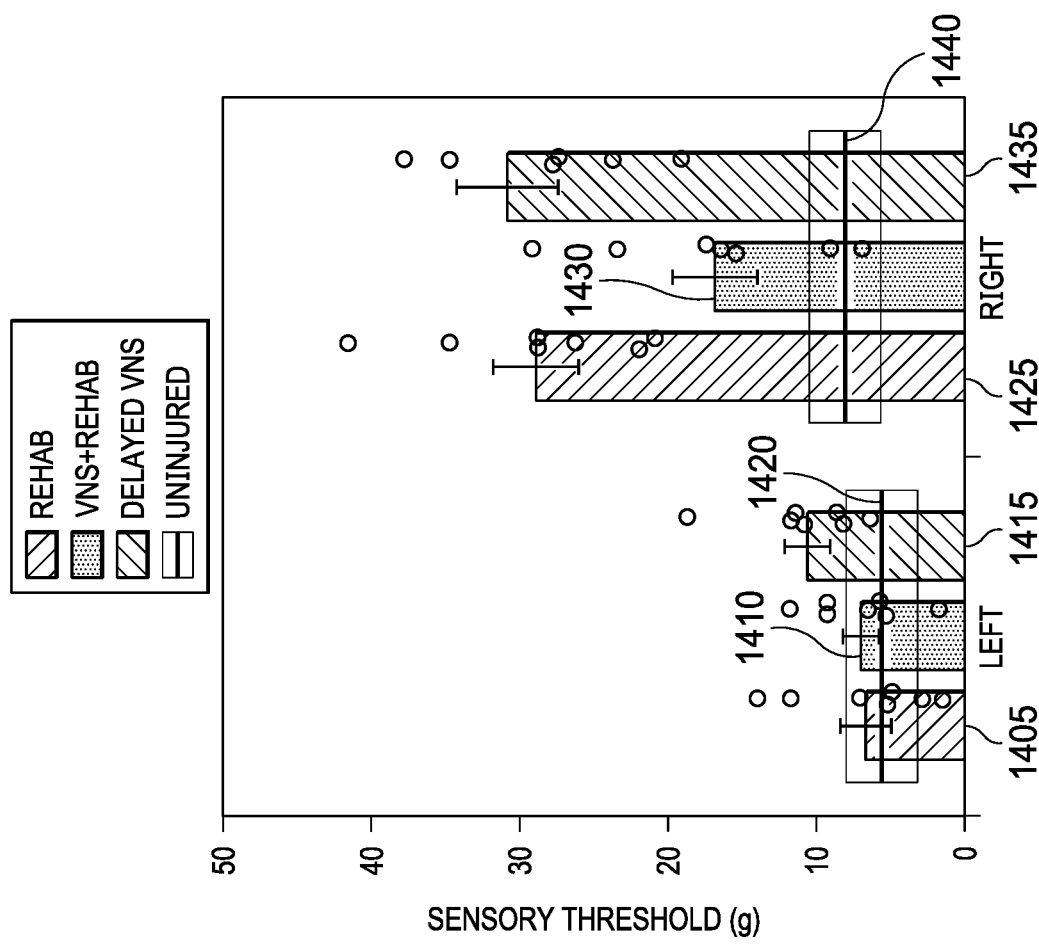

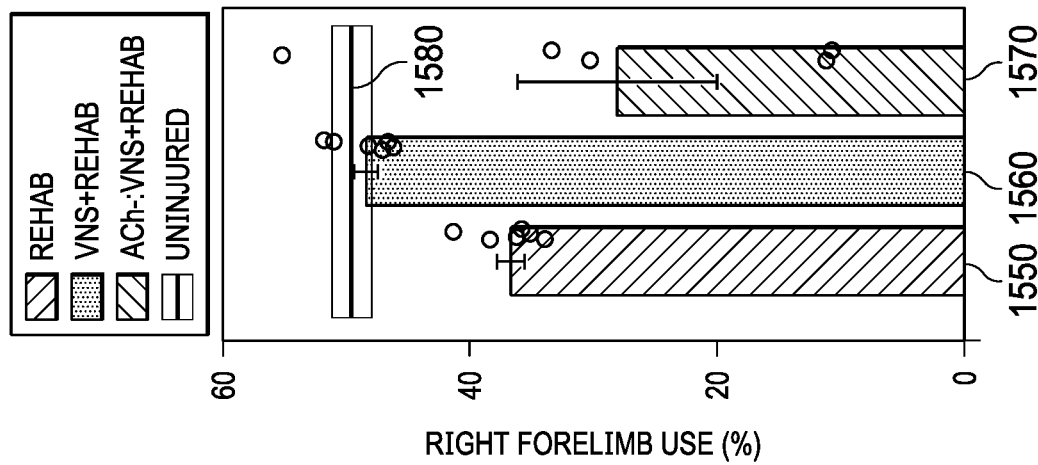
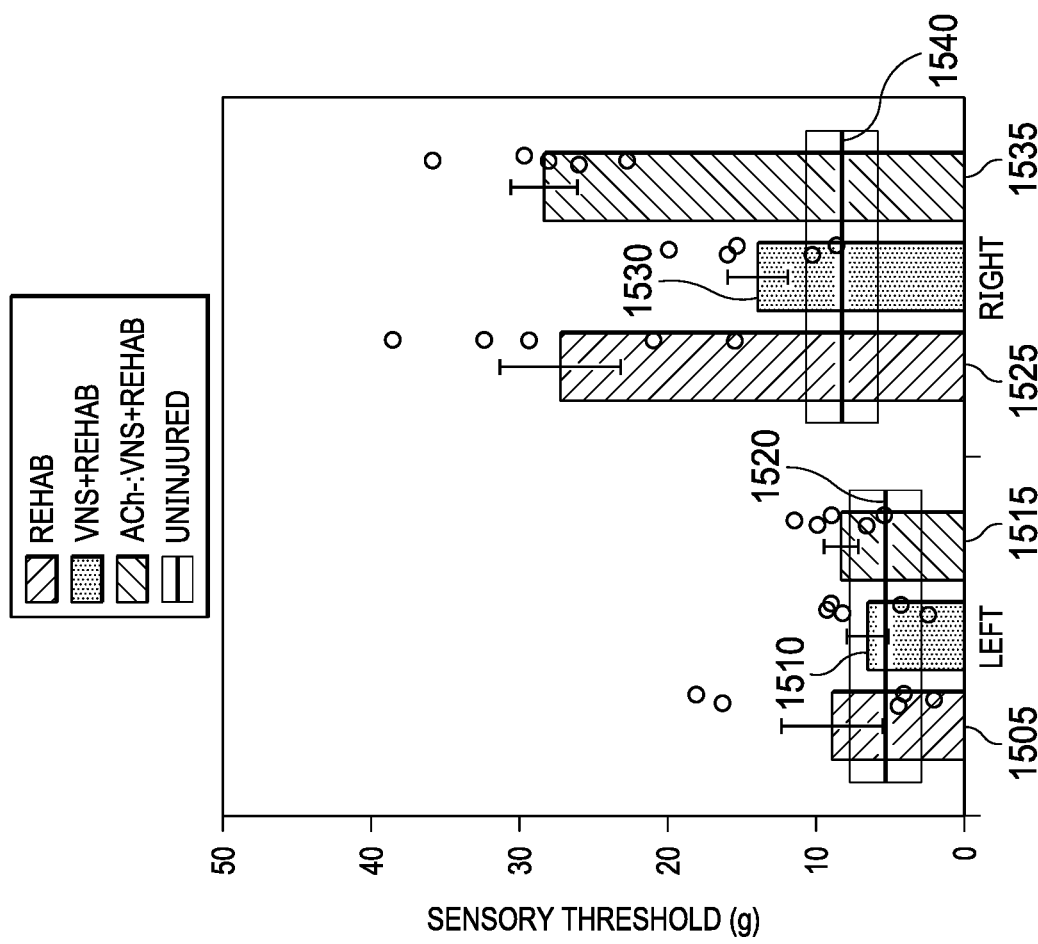

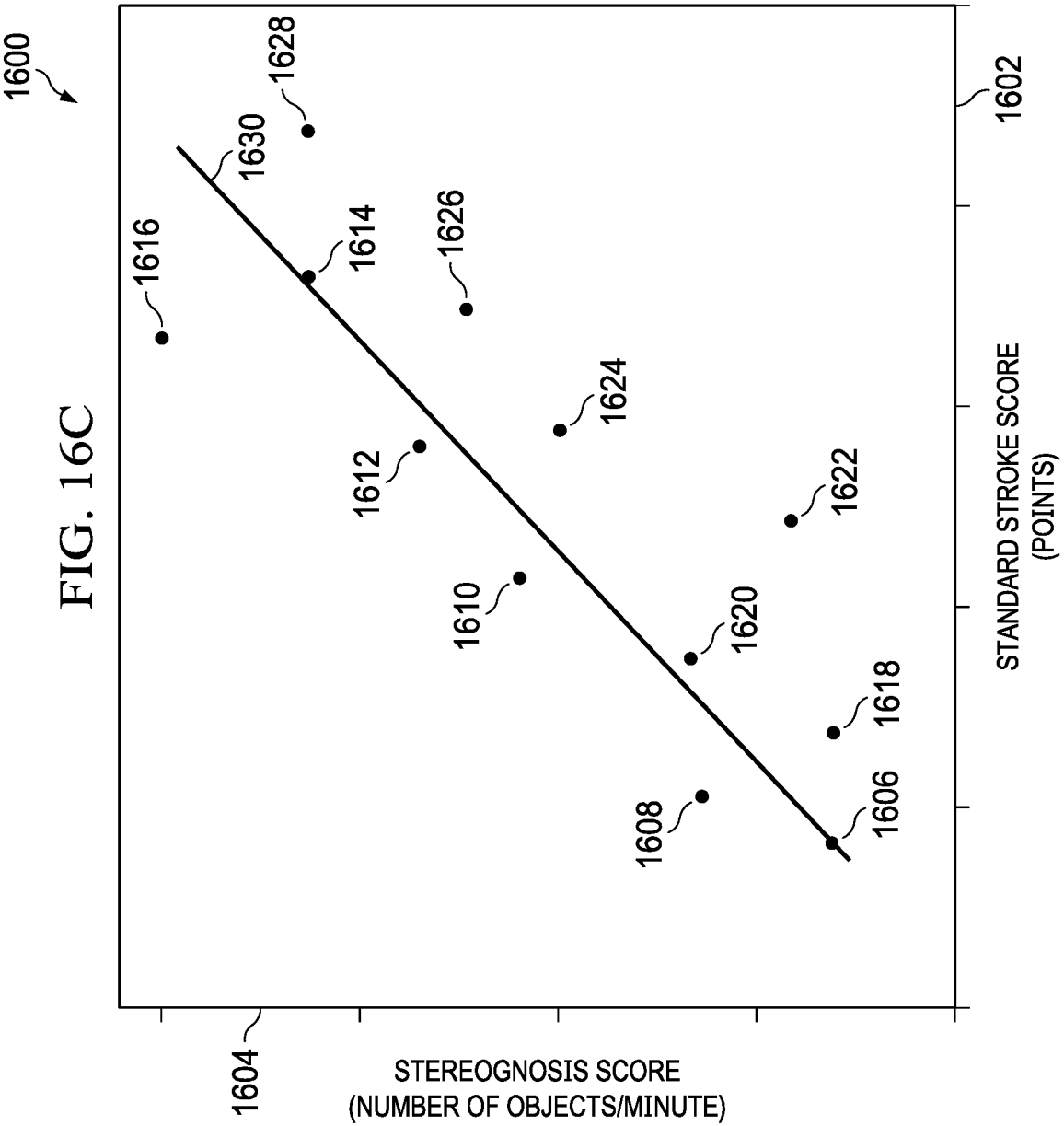

STEREOGNOSIS TRAINING SYSTEM AND METHOD FOR PATIENTS WITH CHRONIC STROKE, SPINAL CORD INJURY OR NEUROPATHY

CROSS-REFERENCE TO RELATED APPLICATIONS

This application claims priority to U.S. Provisional Application No. 62/855,648, filed May 31, 2019, and U.S. Provisional Application No. 62/758,047, filed Nov. 9, 2018. Each patent application identified above is incorporated here by reference in its entirety to provide continuity of disclosure.

STATEMENT OF GOVERNMENT INTEREST

This invention was made with government support under grant number R01-NS094384 awarded by the National Institutes of Health. The government has certain rights in the invention.

FIELD OF THE INVENTION

The present invention relates to a system and method for assessment of and rehabilitation from peripheral nerve damage. More specifically, a unique stereognosis training system and methodology is disclosed. In a preferred embodiment, closed loop vagus nerve stimulation (CL VNS) is paired with assessment of and/or rehabilitation from tactile sensory dysfunction in a patient.

BACKGROUND OF THE INVENTION

Nerve damage is a debilitating neurological disorder that affects over one hundred million people worldwide. Most traumatic nerve injuries occur in the upper extremities, resulting in profound motor and sensory loss and chronic dysfunction of the arm and hand, which can severely reduce quality of life. Despite advances in surgical repair and scaffolding techniques that promote regeneration, long-term prognosis for most patients remains poor. There is a clear and present need to develop interventional strategies that target alternative mechanisms beyond nerve regeneration to restore function in patients after nerve injury.

Immediately after traumatic nerve damage, physical disconnection results in loss of motor and sensory function. This peripheral damage precipitates lasting changes throughout the central nervous system. One consequence of nerve disruption is a sudden and dramatic imbalance of synaptic activity in regions of the brain and spinal cord that control motor and sensory function. This transient perturbation generates profound, long-lasting reorganization as these central networks attempt to compensate for altered peripheral connectivity. Pioneering studies conducted over three decades ago demonstrated that synaptic connections from spared circuits strengthen and dominate central network activity in the absence of competition from the denervated circuits. Over time, injured axons in the damaged nerve sprout, regrow, and establish new connections with targets in the periphery. Despite reconnection of peripheral axons to end targets (e.g., reinnervated muscle fibers and sensory receptors), chronic dysfunction of motor control and sensation often persists. The inability for weakened reinnervated networks to overcome maladaptive central plasticity may contribute to lasting dysfunction.

Indirect evidence supports the role of insufficient central plasticity in chronic dysfunction following nerve injury. Compared to adults, children often display greater recovery despite a similar degree of reinnervation inaccuracies after nerve injury, an effect partially attributed to a greater capacity for plasticity in children. Moreover, imaging studies in humans reveal long-term changes in brain structure and network function that associate with functional impairment. If insufficient central plasticity after nerve damage contributes to chronic dysfunction after nerve damage, then techniques to enhance plasticity and reestablish central network signaling should improve function, even in the absence of changes to the damaged nerve itself.

Sensory impairment of the hand is common after peripheral nerve damage, stroke, spinal cord injury, multiple sclerosis and other neurological conditions. Impaired proprioception, stereognosis and tactile sensation are common after stroke and are associated with poor functional outcomes.

Stereognosis, also known as haptic perception or tactile gnosis, is the ability to perceive and recognize the form of an object, in the absence of visual and auditory information, by using tactile information to provide cues from texture, size, spatial properties, and temperature, etc. Astereognosis is the failure to identify or recognize objects by palpation in the absence of visual or auditory information, even though tactile, proprioceptive, and thermal sensations may be unaffected. Astereognosis can be caused by damage to the posterior association areas of the parietal, temporal, or occipital lobes, or the postcentral gyrus of either hemisphere.

Tactile sensory function is driven by the somatosensory system which processes stimulus such as texture, temperature, pressure etc. The somatosensory system is a complex system of sensory receptors that respond to internal or external stimulus and send sensory information to the brain. Somatosensory receptors are classified into five primary receptor modalities, mechanoreceptors (touch), nociceptors (pain), thermoreceptors (temperature), proprioceptors (position and movement), and chemoreceptors (taste and smell). Proprioceptors are sensitive to the stretch and tension of muscles, tendons, and joints. These receptors allow us to calculate weight and movement.

Mechanoreceptors are found in the dermis or epidermis and are generally associated with the sensation of touch. Mechanoreceptors are broken up into four specialized sensory receptor sub-modalities, Meissner corpuscle, Pacinian corpuscles, Ruffini endings, and Merkel's disks. Meissner corpuscles are sensitive to fine tactile touch and are used to help determine texture. Pacinian corpuscles are sensitive to fast stimulus, such as a jolt, fluttering or vibrating sensations. Ruffini endings are sensitive to skin stretching or movement and give the feeling of object slippage and finger position and control. Merkel's disks are responsive to deep and slow pressure and help determine shapes and edges.

There is no established method to restore tactile sensation after peripheral nerve damage, stroke, spinal cord injury, multiple sclerosis and other neurological conditions. It is widely believed that patients receive inadequate sensory training to promote clinically significant recovery of sensory function. Daily sensory training with a therapist or clinician is prohibitively expensive and requires significant time to travel to and from the clinic.

U.S. Pat. No. 8,489,185 to Kilgard, et al. discloses timing control for paired plasticity. Kilgard discloses a closed loop timing control that is communicably connected to a neural stimulation system and a sensor.

U.S. Pat. No. 8,700,145 to Kilgard, et al. discloses methods, systems, and devices for pairing vagus nerve stimulation with motor therapy in stroke patients. Kilgard discloses a system that may be arranged in a closed loop fashion so that stimulation is automatic, or arranged in an open loop fashion where a therapist is required to intercede before stimulation.

U. S. Publication No. 2018/0221666 to Rennaker, I I, et al. discloses systems and methods for optimizing targeted neuroplasticity. Rennaker discloses a closed loop system for optimizing learning having a vagus nerve stimulator configured to stimulate a vagus nerve of a person with an electrical pulse train; a controller configured to alter one or more parameters of the electrical pulse train while maintaining other parameters of the electrical pulse train constant; and a monitoring device configured to monitor skill learning, where the controller receives feedback from the monitoring device and alters the parameters of the electrical pulse train of the vagus nerve stimulator.

SUMMARY OF THE INVENTION

Millions of people suffer from chronic problems caused by nerve damage, including loss of motor control and paresthesia. These symptoms often persist even after the reestablishment of nerve connectivity, suggesting that denervation alone cannot fully account for dysfunction. It is well-known that nerve damage generates maladaptive neuroplasticity in central networks attempting to compensate for the loss of peripheral connectivity. However, it is not known whether this pathological homeostasis is a critical feature responsible for the expression of peripheral neuropathy symptoms. If pathological central changes contribute to dysfunction, then it is conceived that reversing the changes in central networks should restore motor and sensory function even in the absence of peripheral changes.

Embodiments of this disclosure employ a strategy using brief bursts of closed-loop vagus nerve stimulation (CL-VNS) paired with a well-defined rehabilitation and/or regeneration to reverse the pathological plasticity caused by severe nerve damage. Reversal of aberrant central plasticity results in substantial recovery of motor and sensory function without changes in the nerve or muscle, such that plasticity in brain and spinal networks mediate recovery. Anatomical and physiological studies reveal that CL-VNS therapy drives extensive synaptic reorganization in central networks. Depletion of acetylcholine in the brain blocks plasticity and subsequently eliminates functional recovery. These findings demonstrate that manipulations to enhance plasticity in central networks improves motor and sensory recovery and define CL-VNS therapy as a novel and readily translatable therapy to restore function after nerve damage.

Rehabilitation for astereognosis and tactile sensory dysfunction in the clinic is expensive and produces insufficient numbers of trials per week. At home therapy can be effective with or without the addition of adjuvant therapies such as vagus nerve stimulation (VNS). The present invention allows patients to improve sensory and motor function through stereognosis practice enhanced by the use of mobile technology.

In one aspect of the invention, a method and system of treatment for peripheral nerve damage of a subject includes targeting reversal of maladaptive central network plasticity resulting from the peripheral nerve damage by enhancing plasticity in at least one of a motor or a sensory network of the subject. This treatment releases cortical acetylcholine during rehabilitative training to enhance plasticity in the motor or the sensory network.

In another aspect of the invention, a method and system for treatment for peripheral nerve damage applies a closed-loop vagus nerve stimulation during a rehabilitation of the damaged peripheral nerve wherein a vagus nerve stimulation signal is applied coincidentally with the rehabilitation. In yet another aspect, the rehabilitation comprises applying a stimulus to the sensory network of the subject.

In a further aspect of the invention, a method and system of treatment for peripheral nerve damage wherein a closed-loop vagus nerve stimulation is applied coincidentally upon completing a successful rehabilitative task. The successful rehabilitative task comprises specific movements or exercises during rehabilitation of the damaged peripheral nerve that meet specified quantitative or qualitative criteria predefined by a therapist or a measurement system. In one aspect, the method and system comprises pairing the step of applying a closed-loop vagus nerve stimulation with a regenerative therapy of the peripheral nerve damage wherein the regenerative therapy is as any strategy that promotes nerve regrowth or reinnervation. In another aspect, the regenerative therapy comprises at least one of surgical techniques, nerve conduits, treatment with growth factors, electrical stimulation of the damaged nerve, or pharmacological treatments.

A stereognosis training system for a patient is disclosed comprising a set of objects categorized by tactile sensory function wherein an obstruction visually obscures the set of objects from the patient. In an aspect of the present invention, an interactive device in the system is configured to select a test object, direct the patient to identify and grasp the test object from the set of objects and determine if the patent correctly identified and grasped the test object.

The set of objects of the present invention have many different features and aspects. For example, the set of objects have different feature sizes and/or different colors based on tactile sensory function. One important feature of the set of objects is that subsets of objects can be chosen to stimulate a particular tactile sensory function. In another aspect, the set of objects includes subsets of objects that stimulate a selected receptor group of the somatosensory system or multiple receptor groups of the somatosensory system. The receptor groups may be selected, for example, from cutaneous receptors, mechanoreceptors, nociceptors and thermoreceptors.

In another aspect, the particular tactile sensory functions include size, texture, heat conductance, temperature, weight, density, ductility, flexibility, yield-strength, compliance, homogeneity, vibration, friction, viscosity, stickiness, orientation stability and pain.

In other aspects, a subset of objects is chosen to have a common fixed feature. For example, the subset of objects have the same weight. In yet other aspects, a subset of objects have common varying features. For example, subsets of objects have varying ability to stimulate pain, have varying texture or have varying size. In yet other aspects, a subset of objects have one of more common fixed features for a set of tactile sensory functions while also having one or more common varying features for a different set of tactile sensory functions. For example, the subset of objects have the same size, shape and texture but vary in density.

In one embodiment of the stereognosis training system, an obstruction is provided that visually obscures the set of objects from the patient such as a blindfold. In other embodiments of the stereognosis training system, the obstruction that visually obscures the set of objects from the patient is a curtain or a solid obstruction between the patient's eyes and the set of objects. In each case, the patient's hands remain free to grasp the set of objects.

In another embodiment of the stereognosis training system, the obstruction that visually obscures the set of objects from the patient is a box comprising a set of solid walls, a floor and an opening or penetrable wall sufficient for a hand of the patient to be inserted into the box while obscuring the inside of the box from view of the patient.

In other embodiments, the stereognosis training system is configured to automatically distribute the set of objects on the floor of the box. For example, in one embodiment, the floor is sloping away from the penetrable wall so that the set of objects are distributed away from the penetrable wall so that the patient is better able to locate all of the blocks within the box. In another embodiment, the set of objects are automatically distributed with random placement inside the box utilizing, for example, a guide for loading and distributing the set of objects inside the box.

In another aspect of the present invention it is conceived that the interactive device be a smart phone or other computer device. There are many features and programmable aspects of smart phones and computer devices useful to the present invention. For example, the interactive device is further configured to visually identify a test object to the patient for the patient to retrieve from the box. In another aspect, the interactive device is configured to audibly identify a test object to the patient for the patient to retrieve from the box.

In yet another embodiment of the stereognosis training system, an attachment is included for holding the interactive device. Examples of an attachment may be a transparent shelf attached to the walls of the box or a transparent shelf attached to a self-supporting structure further attached to or sitting upon a desk on which the box is placed.

In another feature of the present invention, the interactive device is further configured to accept at least one of a screen tap or an audible sound to determine if the patient correctly identifies and grasps the test object. In a related feature, the interactive device is further configured to automatically determine if the patient correctly identifies and grasps the test object without requiring the patient to touch the interactive device or create an audible sound for the interactive device.

In other aspects of the present invention, the interactive device is further configured to determine an ability of the patient to correctly identify and grasp a test object in response to a request to retrieve the test object. In yet another aspect, the interactive device is further configured to determine an elapsed time from when the patient inserts their hand into the box in response to a request to retrieve a test object until when the patient correctly identifies and grasps the test object and to further record the elapsed time as the ability of the patient to correctly identify and grasp the test object. In a further aspect, the interactive device is configured to record the determination that the patient correctly identified and grasped the test object as a score and transmit the score to a second device.

In another embodiment, the system is configured to measure and record the interaction time that the patient interacts with the interactive device, for example when the patient touches the screen of the interactive device or moves their hand into or out of the field of view of a camera of the interactive device. Such a measure and recording of the interaction time may also provide a measure and recording of the rate of movement outside the box, and a measure and recording of when the hand moves from inside the box to the field of view of the camera. In yet another aspect, the system measures and records the speed of movement and hand position during object exploration.

In another embodiment of the present invention, the stereognosis training system further comprises a stimulation device for the patient wherein the stimulation device is communicatively attached to the interactive device. It is further conceived that the interactive device be configured to determine whether or not the patient's hand is inserted into the box and stimulates the patient with the stimulation device while the patient's hand is inserted into the box. In another aspect of the stimulation feature, the stimulation device is configured to stimulate the vagus nerve of the patient.

The present invention includes an embodiment for a method for improving tactile sensory function in a patient using a stereognosis training system for a patient having a set of objects categorized by tactile sensory function wherein an obstruction visually obscures the set of objects from the patient and having an interactive device in the system configured to select a test object, direct the patient to identify and grasp the test object from the set of objects and determine if the patent correctly identified and grasped the test object. The method for improving tactile sensory function comprises the step of assessing tactile recognition with the stereognosis training system to determine a set of tactile sensory deficits and a tactile sensory score. The method further comprises directing the patient to practice tactile recognition with the stereognosis training system based on the set of tactile sensory deficits.

In another embodiment, the method for improving tactile sensory function in a patient further comprises the steps of targeting a target sensory deficit in the set of tactile sensory deficits for rehabilitation based on the assessment; selecting a subset of the set of objects based on the target sensory deficit; directing the patient via the interactive device to retrieve at least one object from the subset of the set of objects; determining whether the patient retrieved the at least one object; and, determining a tactile function score based on whether the patient retrieved the at least one object.

In a further embodiment, the rehabilitation is adjusted by re-selecting the target sensory deficit for rehabilitation based on the tactile function score. Then the method for improving tactile sensory function is repeated beginning with the step of selecting a subset of the set of objects based on the (different) target sensory deficit.

Other embodiments of the method for improving tactile sensory function in a patient include recording minutes per day of practice with the stereognosis training system, plotting usage history of the stereognosis training system, tracking a history of tactile sensory scores, sending a reminder message to the patient reminding the patient to practice therapy, triggering simultaneous vagus nerve stimulation based on tactile sensor scores, quantifying hand position and speed of movement during haptic exploration and retrieval of the at least one object, providing instructions for using the stereognosis training system. In yet another embodiment a step of tracking a history of tactile sensory scores and determining improvement in tactile sensory function of the patient is included. In yet another embodiment, feedback is provided to the patient based on the improvement in tactile sensory function and the history of tactile sensory scores.

In another aspect of the present invention, the foregoing steps of the method for improving tactile sensory function and the various embodiments can be performed by the interactive device.

Another embodiment is conceived wherein the method for improving tactile sensory function comprises sensing the patient's hand position and causing a stimulator device to stimulate the vagus nerve of the patient based on the patient's hand position.

Objects used in stereognosis training are easily identified visually but challenging for a stroke or spinal cord injury patient to identify by touch alone. Object sets have been conceived that have different levels of difficulty for identification by touch (active exploration, stereognosis). The most distinct objects differ in multiple tactile sensory functions (dimensions). Difficult contrasts in stereognosis will be of a single tactile sensory function (dimension). For example, objects sets are conceived to challenge individual dimensions such as length, curvature, texture roughness and weight.

Object weight and center of gravity can be adjusted by producing hollow spaces in 3D printed objects or by adding weights to hollow spaces. Differences in weight and associated momentum change (during movements) will allow for mass estimation.

It is also conceived that placement of objects in specific locations would be advantageous for use and assessment of tactile memory. This becomes more important when a greater number of objects and greater level of difficulty in training is required.

For example, the objects in each set are a different color so it is easy to ensure the right objects for a particular tactile sensory function are in each set and returned there after each discrimination. Additionally, each object is optionally labeled with a number (that cannot be felt). Object sets of real world objects are also conceived such as a brush, a spoon, a set of keys, a tube of toothpaste or pair of eye glasses (for example). For severely impaired individuals, object sets are conceived to have an upward facing handle or putty (which adheres to the shape of the hand when grasping).

In addition to object sets, a system and method is disclosed for the patient to assign tasks, interact with an object set and complete tasks with the object set is conceived. For example, a box to obscure vision is provided without obscuring hand access wherein the box can be loaded from above so locations of the objects are not known at the beginning of each task.

An interactive device is integrated with the stereognosis training system to direct, monitor and provide feedback for patient activity. In an illustrative embodiment, a smart phone operating a programmed application uses an on-board camera to detect that the patient's hand has entered the box. The box (or another embodiment of stereognosis apparatus) is modified to hold the phone and angle the camera appropriately to make observations and allow for patient interaction. Such an event can be time-stamped and utilized to trigger time-coordinated external stimulation, such as vagus nerve stimulation. In one embodiment, an easily identifiable object is worn on the hand (for example colored bracelet) to confirm when the hand of the patient is engaged with the object set. In another embodiment, the pattern of the patient's active hand exploration is determined to analyze stimulation timing.

A clinical tool is conceived to confirm improvement in stereognosis and tactile sensory function by measuring individual dimensions of density, texture, compliance, shape, and so forth. Repeated testing and use of quantitative measures (average time required to identify objects with specific physical differences) will yield more reliable and more sensitive assessments of sensory function compared to current clinical methods.

The stereognosis system of the present invention provides a much needed improvement in the art of stereognosis assessment, rehabilitation and treatment in that: it is inexpensive from a hardware/software and treatment perspectives (no therapist is required), it is transportable with potentially lightweight construction and easy setup, it can provide challenging and directed practice for the patient in individual dimensions and in dual or multiple physical dimensions, it can utilize real world objects, the objects sets are color coded, the objects cover a wide range of difficulty to cover the wide range of impairment from easy to grasp objects to more difficult, it blocks visual cues during object exploration but provides clear visual feedback when needed using an interactive device, it can provide motivating encouragement and reminders through the interactive device, it is practical for home use and the treatment can be paired with external stimulation (for example vagus nerve stimulation) using the interactive device, it can reduce inactivity and contractures through grasp-search-release-repeat structure, it can detect and record history of practice time and assess progress in training, it is normed to real tactile sensory function data to set appropriately difficult tasks as the patient progresses, video and audio advice are provided to the patient to guide therapy based on performance.

A stereognosis training system comprises: a box with a hand access opening; a camera with a lens; a computing device with a video input coupled to the camera; an interior surface within the box that is reachable by a patient via the hand access opening; and a set of objects located within the box and on the interior surface; wherein at least one of the set of objects is optically tracked using the camera and the computing device to generate a time domain stream of data on at least one of location, rotation, and vibration for the at least one object of the object set. In a preferred embodiment, the computing device has a signal output to trigger a closed loop nerve stimulation to the patient. In a preferred embodiment, a mirror is optically coupled between the lens of the camera and the interior surface. In a preferred embodiment, the camera and the computing device are integrated components of a mobile device such as a smart phone, tablet or laptop. In a preferred embodiment, the mobile device is mechanically connected to an adaptor that is mechanically coupled to the enclosure to hold the mobile device and optically couple the lens of the camera to the mirror. In a preferred embodiment, the enclosure has an arm rest positioned beneath the hand access opening. Optionally, the arm rest can be removable. In a preferred embodiment, the enclosure has a chute to introduce the object set onto the interior surface.

A method of stereognosis training comprises: cuing a patient to identify and retrieve at least one member of an object set; and optically tracking a hand of the patient and the at least one member of the object set using computing device having a camera and a microprocessor to generate a time domain stream of data on the hand of the patient and the at least one member of the object set. In a preferred embodiment, the method comprises automatically triggering a vagus nerve stimulation (CL VNS) to the patient with a signal output from the computing device.

In a preferred embodiment, the system and method comprise providing within the box a set of objects (object set) where each of the objects is characterized by a different color. In this way, the camera and microprocessor can track each of the objects. Tracking can include recognizing and locating. This recognizing and locating by color can be verified based on the pixels that the camera associates with the color. In this way, each object can be identified by a color and a number of pixels. Each of the pixels can have three or four component intensities such as red, green, and blue, or cyan, magenta, yellow, and black.

In an alternative embodiment, the system and method comprise providing at least one fiducial on each of the plurality of objects that uniquely identifies each object and that indicates both scalar position of each object and directional orientation of each object. The use of at least one fiducial on each of the objects enables readily available augmented reality tools for mobile devices to generate a time domain stream of data on at least one of position, rotation, and vibration for each of the objects of the object set.

A nerve stimulation signal can be triggered based on the time domain stream of data meeting criterion associated with a performance threshold. The performance threshold can be moving the object that was cued and/or removing the object that was cued from the box (from the view of the camera). In a preferred embodiment, the signal is automatically handled in a closed loop from the microprocessor to an implanted vagus nerve stimulator via a network interface and a wireless local area network. The time domain stream of data can be reported to a remote device such as a clinical device monitored by a therapist or an application server that is connected to a database. The determination of whether the time domain stream of data meets the criterion associated with the performance threshold can be performed with software by the computing device and/or the remote device, without the need for a therapist or clinician. This is an important advantage of the invention because obviating the need for a therapist or clinician dramatically reduces costs. It also makes the determination more objective and less subjective.

In an embodiment of the present invention, the computer is configured to detect and measure hand insertion into the stereognosis system. The tablet computer also detects and measures duration times for a patient searching for an object and/or retrieving the object from the box.

It is an object of the present invention to engage the patient in practice of stereognosis leading to rehabilitation of tactile sensory function. In so doing, an interactive device records minutes of use per day, number of attempts and number of successes.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIGS. 6A-6G are schematic diagrams of various sets of objects in accordance with illustrative embodiments of the invention.

FIG. 8A is a summary table of sets where three sets are constructed for each object type within a range of features and objects in some sets may be more difficult to distinguish than in other sets in accordance with illustrative embodiments of the invention.

FIG. 8B is a schematic drawing of a cutaway view of an exemplary object set.

FIGS. 14A-14B are a set of bar graphs illustrating reversal of pathological plasticity restores sensory function after nerve injury in accordance with an illustrative embodiment of the invention.

FIGS. 15A-15B are a set of bar graphs showing reversal of pathological plasticity is necessary to restore sensory function after nerve injury in accordance illustrative embodiments of the invention.

FIG. 16C is a graph of a benchmarked assessment in accordance with an illustrative embodiment of the invention.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness.

In the description of the embodiments and experimental details that follows, the term "plasticity" means a capacity of a human brain to reorganize itself to form new connections between neurons. The term "rehabilitation" means any standard physical rehabilitative exercise, such as those targeted to improve range of motion or strength, performed with a therapist or self-guided, and includes the use of rehabilitative devices. The term "successful rehabilitation" is defined as specific movements or exercises during rehabilitation that meet specified quantitative or qualitative improvement criteria, such as force, speed, range of motion, or stability, as defined by a therapist or a measurement system. The term "regeneration" or, alternatively, "regenerative therapies," are defined as any strategy that promotes nerve regrowth or reinnervation, including surgical techniques, nerve conduits, treatment with growth factors, electrical stimulation of the damaged nerve, or pharmacological treatments. The term "closed-loop vagus nerve stimulation" (CL-VNS) means a neuromodulation strategy wherein electrical stimulation of the vagus nerve of a subject occurs substantially simultaneously to a measured action of the subject. The term "open-loop vagus nerve stimulation" (OL-VNA) means a stimulation of the vagus nerve of a subject that is not substantially simultaneously with a measured action of the subject. The term "substantially simultaneous" means within no more than three (3) seconds before or after the observed patient action.

"Stereognosis" is the ability to perceive or the perception of material qualities (such as shape) of an object by handling or lifting it to get tactile information. "Astereognosis" is the failure to identify or recognize objects by palpation in the absence of visual or auditory information.

Figure 1B:
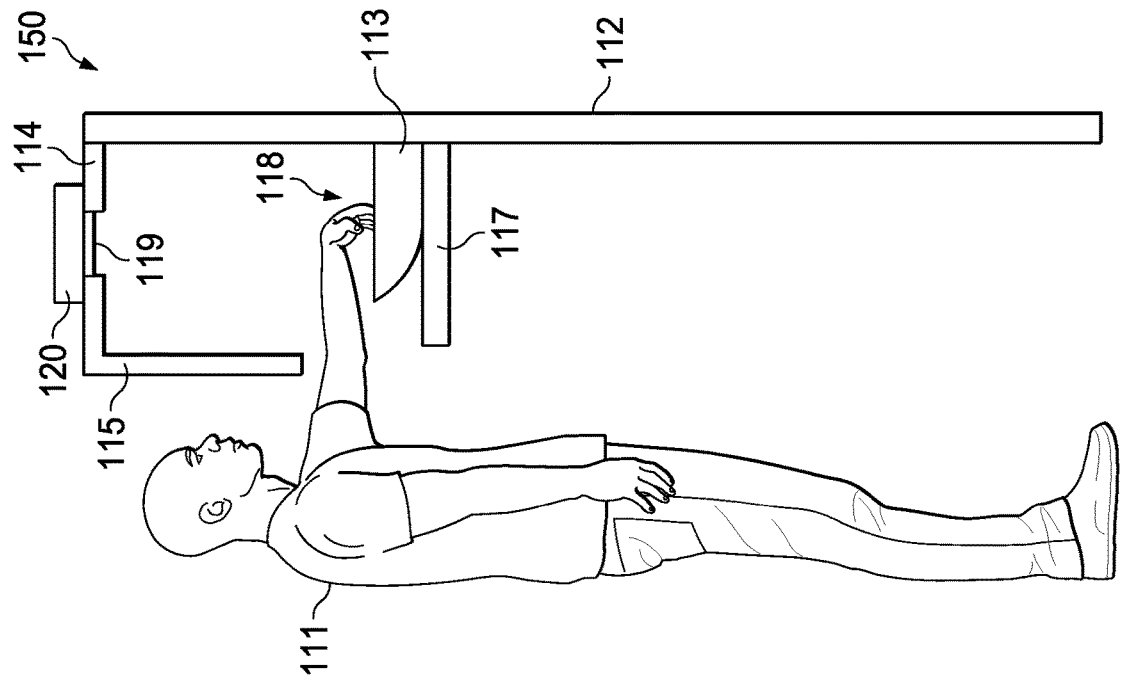
FIG. 1B is a schematic diagram of a stereognosis training system with an obscuring screen in accordance with an illustrative embodiment of the invention.
Figure 1A:
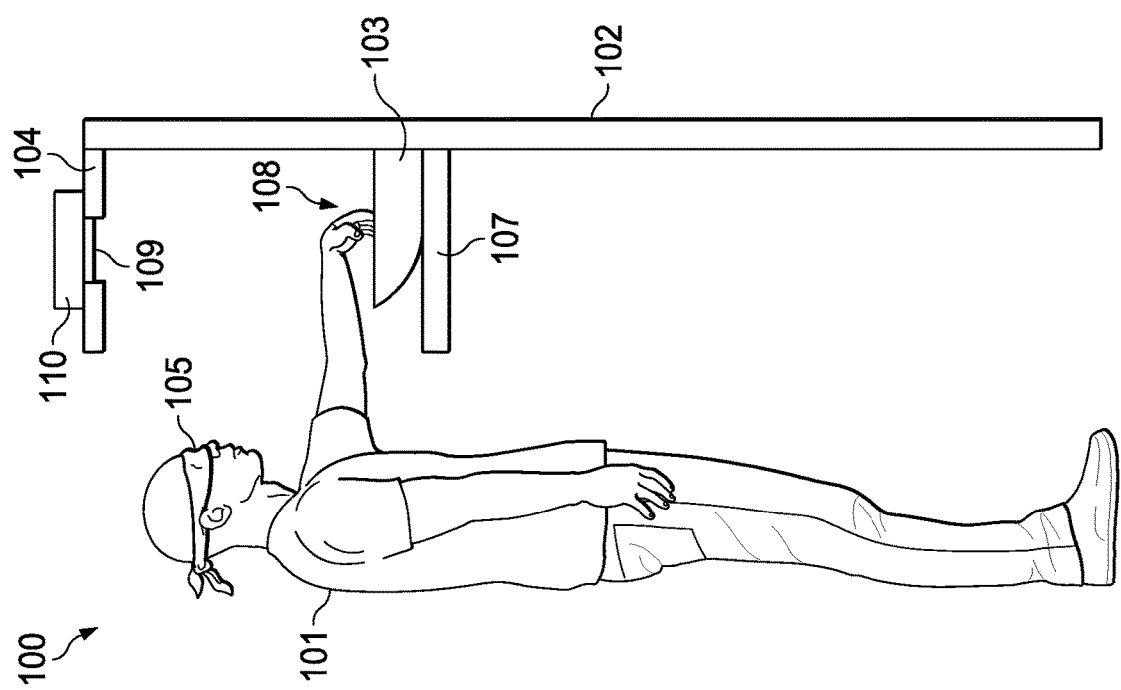
FIG. 1A is a schematic diagram of a stereognosis training system with a blindfold in accordance with an illustrative embodiment of the invention.

FIG. 1A shows an illustrative embodiment of stereognosis training as a simple blindfold based stereognosis training system 100. System 100 comprises container 103 on support 107 in which set of objects 108 are placed. Support 102 is attached to support 107. Surface 104 is attached to support 102. Surface 104 includes transparent window 109. Interactive device 110 is positioned adjacent the window. In a preferred embodiment, the interactive device is a tablet counter configured with a downward facing camera and an upward facing display. The downward facing camera is positioned to view the container and the blocks through the window. The interactive device can record images of patient 101 interaction with set of objects 108. System 100 also includes blindfold 105 for obscuring the patients view of set of objects 108.

FIG. 1B shows an illustrative embodiment of stereognosis training system 150. System 150 comprises container 113 on support 117 in which set of objects 118 are placed. Support 112 is attached to support 117. Surface 114 is attached to support 112. Surface 114 includes transparent window 119. Interactive device 120 is placed adjacent transparent window 119. The interactive device can record images of the patient 111 interaction with set of objects 118. Opaque panel 115 is attached to surface 114 and obscures the patient's view of set of objects 118.

FIGS. 2A, 2B, 2C, 2D, and 2E show perspective and cutaway views of an alternate preferred embodiments of the stereognosis training system. Training system 200 comprises front wall 204, back wall 207 side walls 202a and 202b and floor 203 attached together form light tight box 201. Set of objects 208 is placed on floor 203, preferably randomly distributed. Preferably, the area of the floor is sufficient to allow for considerable haptic exploration, but yet small enough to be easily portable. Front wall 204 further comprises opening 210. The opening is large enough to accommodate stroke patients with spasticity, or poor motor control. In one embodiment, the box is approximately 2 foot square with a height of about 2 feet. In this embodiment, the opening is about 6"×18". The interior surfaces of the floor and the walls are preferably rubberized to reduce auditory cues about object identity.

Device support 218 is attached near the top of the box to one or more of the front, back and side walls. Device support 218 is comprised of a transparent material which is safe, such as plexiglass. In a preferred embodiment, the device support is positioned at angle 250 relative to the floor. In this embodiment, angle 250 must be sufficient to allow the camera to view the entirety of the floor inside the box.

Front wall 204 further comprises curtain 205 to allow a patient to insert a hand through opening 210 without seeing set of objects 208. Curtain 205 is opaque and preferably black. Further to the visual obstruction of the set of objects from the patient, the box sides are positioned and of sufficient dimension to obstruct the line of sight from the top of the box. The top of the box includes opening 260. In a preferred embodiment, opening 260 is of sufficient size to allow for an impaired patient to drop object sets onto the floor. Adjacent opening 260 is guide 206. Guide 206 is attached to back wall 207 and side wall 202a. The guide forms a downward facing ramp which allows easy placement into the box and assist in randomly distribute them on the floor.

Figure 2A:
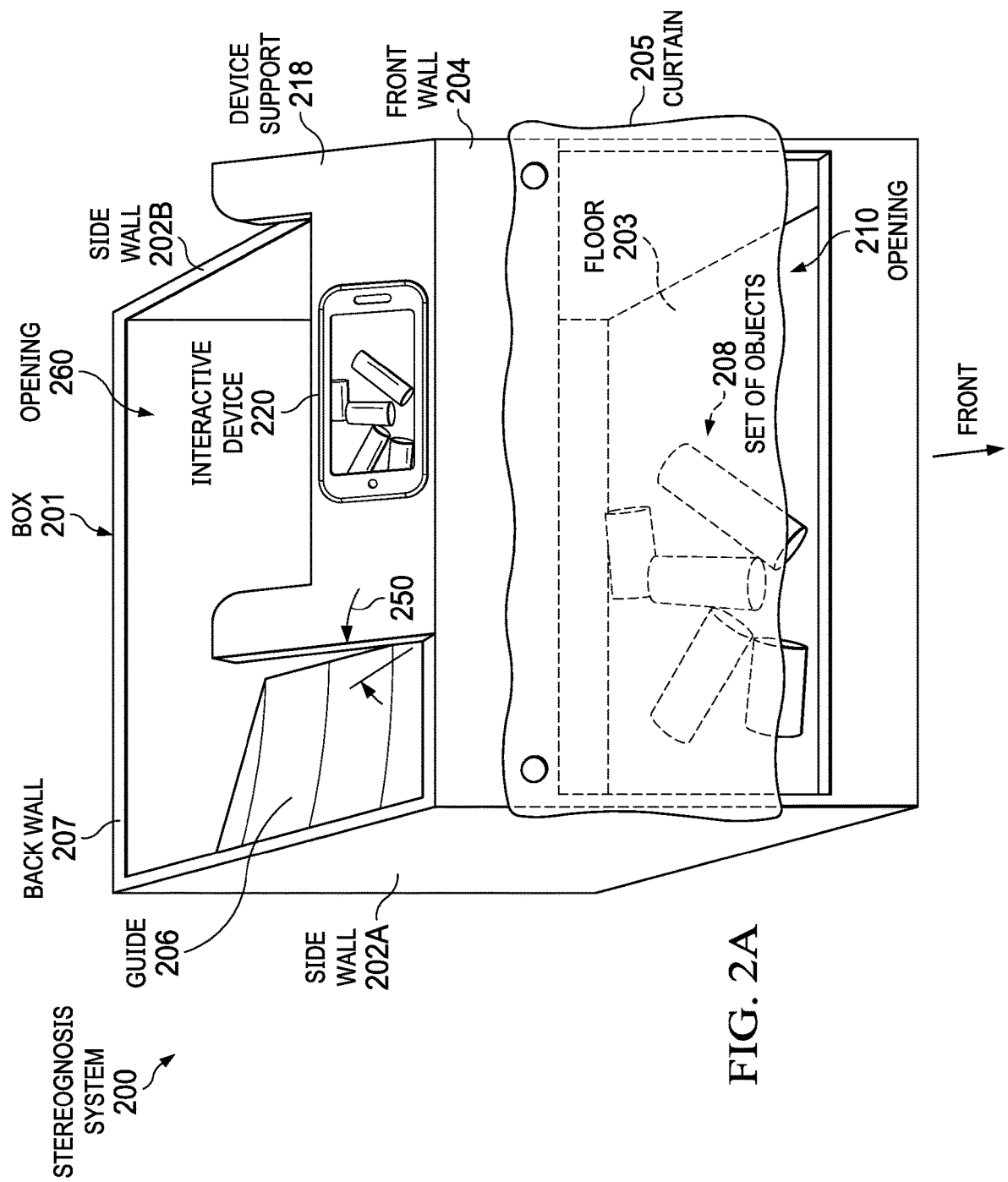
FIG. 2A is a perspective view of a stereognosis training system with a box, an obscuring screen and a curtain in accordance with an illustrative embodiment of the invention.
Figure 2B:
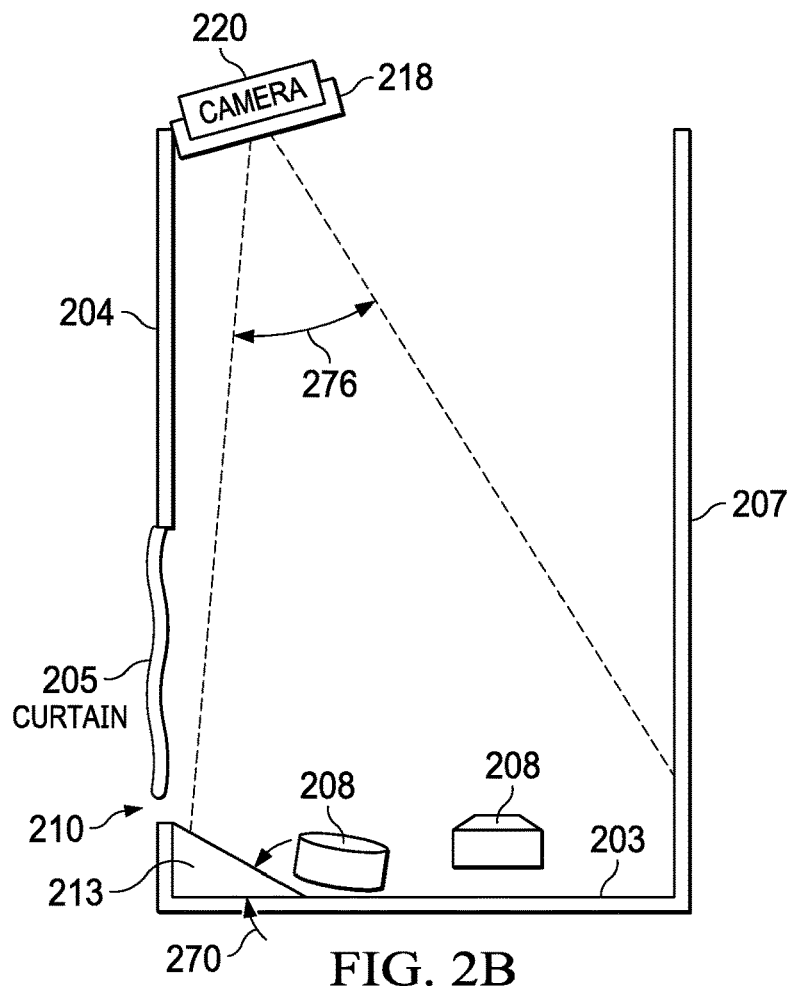
FIG. 2B is a side view of a stereognosis training system utilizing a box with a slope insert, an obscuring screen and a curtain in accordance with an illustrative embodiment of the invention.
Figure 2C:
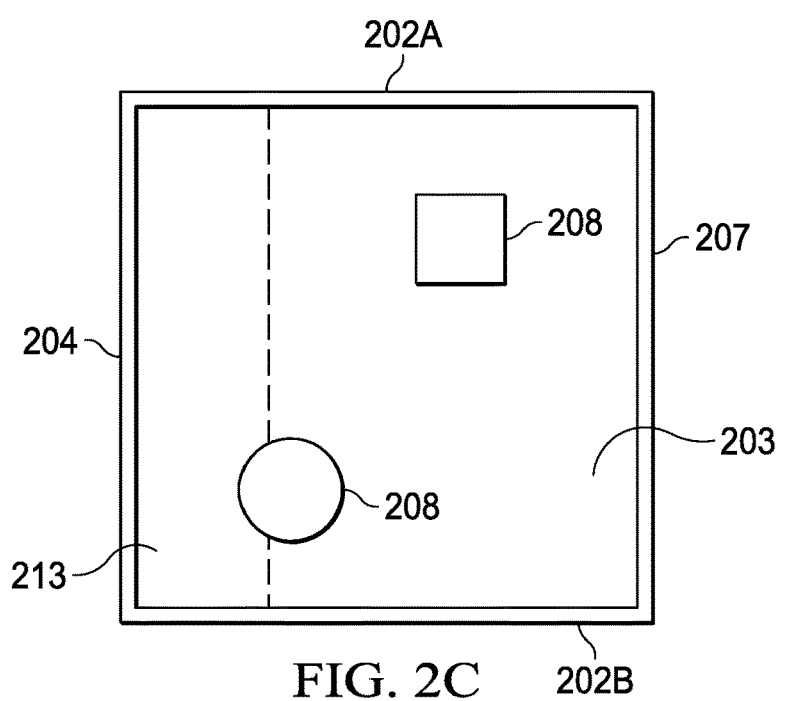
FIG. 2C is a top view of a stereognosis training system utilizing a box with a slope insert, an obscuring screen and a curtain in accordance with an illustrative embodiment of the invention.

In FIGS. 2B and 2C, the system further comprises sloped floor section 213 which begins at opening 210 and slopes downward at angle 270 toward back wall 207. Preferably angle 270 is about 30°. In a preferred embodiment, the sloped floor section is about 4" long and spans the entirety of front wall 204 directly below the opening. The sloped floor may be accomplished by a removable insert.

In this embodiment, interactive device 220 includes field of view 276 which can be seen to encompass the entirety of sloped floor section 213 and floor 203. The purpose of the slope floor is to distribute the set of objects away from front wall 204 so that blocks are not placed beneath the patient's palm or wrist and are more easily found during a search.

Figure 2D:
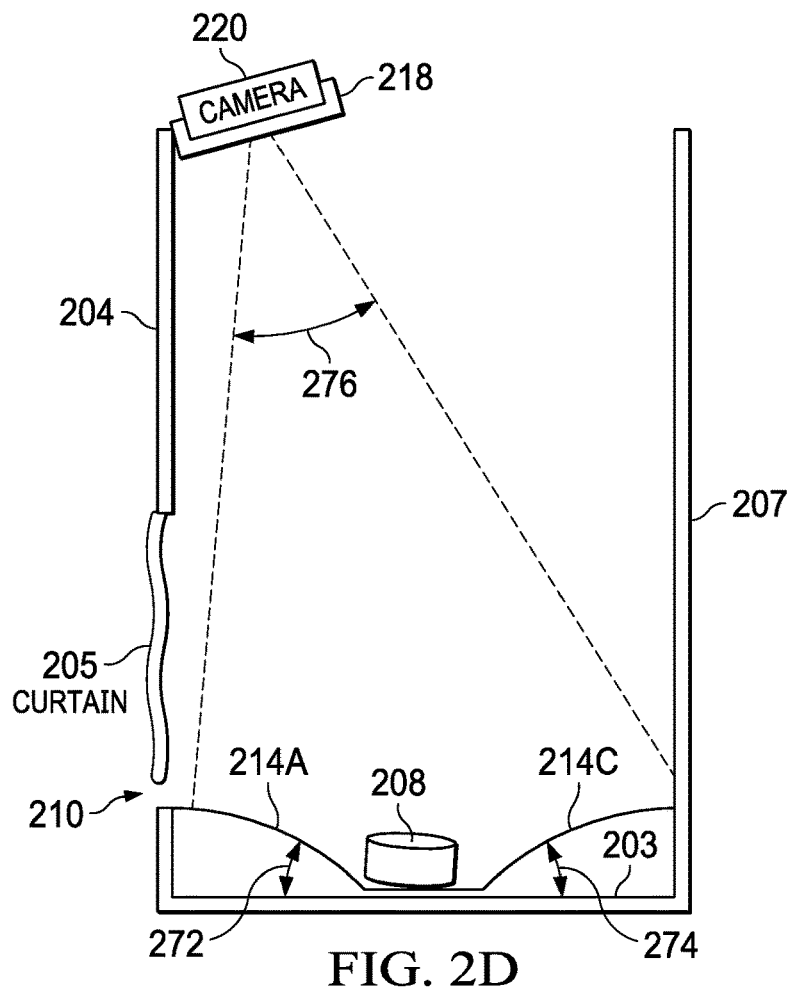
FIG. 2D is a side view of a stereognosis training system utilizing a box with a centering insert, an obscuring screen and a curtain in accordance with an illustrative embodiment of the invention.
Figure 2E:
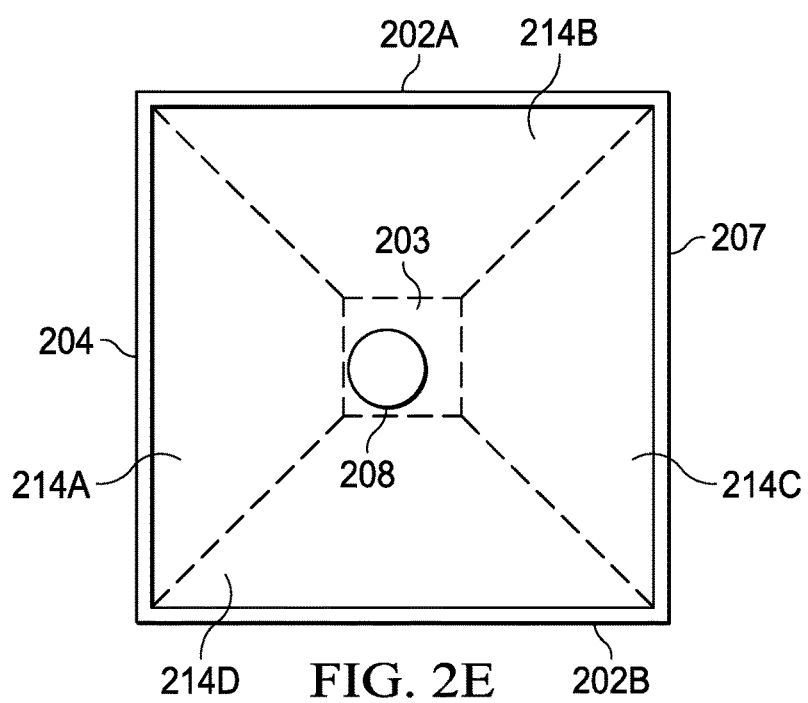
FIG. 2E is a top view of a stereognosis training system utilizing a box with a centering insert, an obscuring screen and a curtain in accordance with an illustrative embodiment of the invention.

In FIGS. 2D and 2E, training system 200 further comprises centering insert 214 adjacent floor 203.

The centering insert is further comprised of sloping section 214a, 214b, 214c and 214d. Section 214a begins at the lower surface of opening 210 and extends to floor 203 and contacts sections 214b and 214d. Similarly, section 214b begins at side wall 202a and extends to floor 203, contacting sections 214a and 214c. Likewise, section 214c begins at back wall 207 and slopes toward floor 203, contacting sections 214b and 214d. Section 214d begins at side wall 202b and slops toward floor 203, contacting section 214c and 214a. Each of the sections makes an angle of approximately 30° from the floor, shown in this example as angle 272 and 274. The insert comprises an inverted pyramid. However, in other embodiments, the insert can comprise an inverted frustoconical surface beginning at the sidewalls and terminating at the floor. The centering floor system could also be integrated with the floor. The purpose of the insert is to distribute the set of objects away from walls so that they are more easily accessible to the patient during use.

The opening must be such that objects will not escape when loaded from the top. The sloped sections from provide this function.

Figure 3:
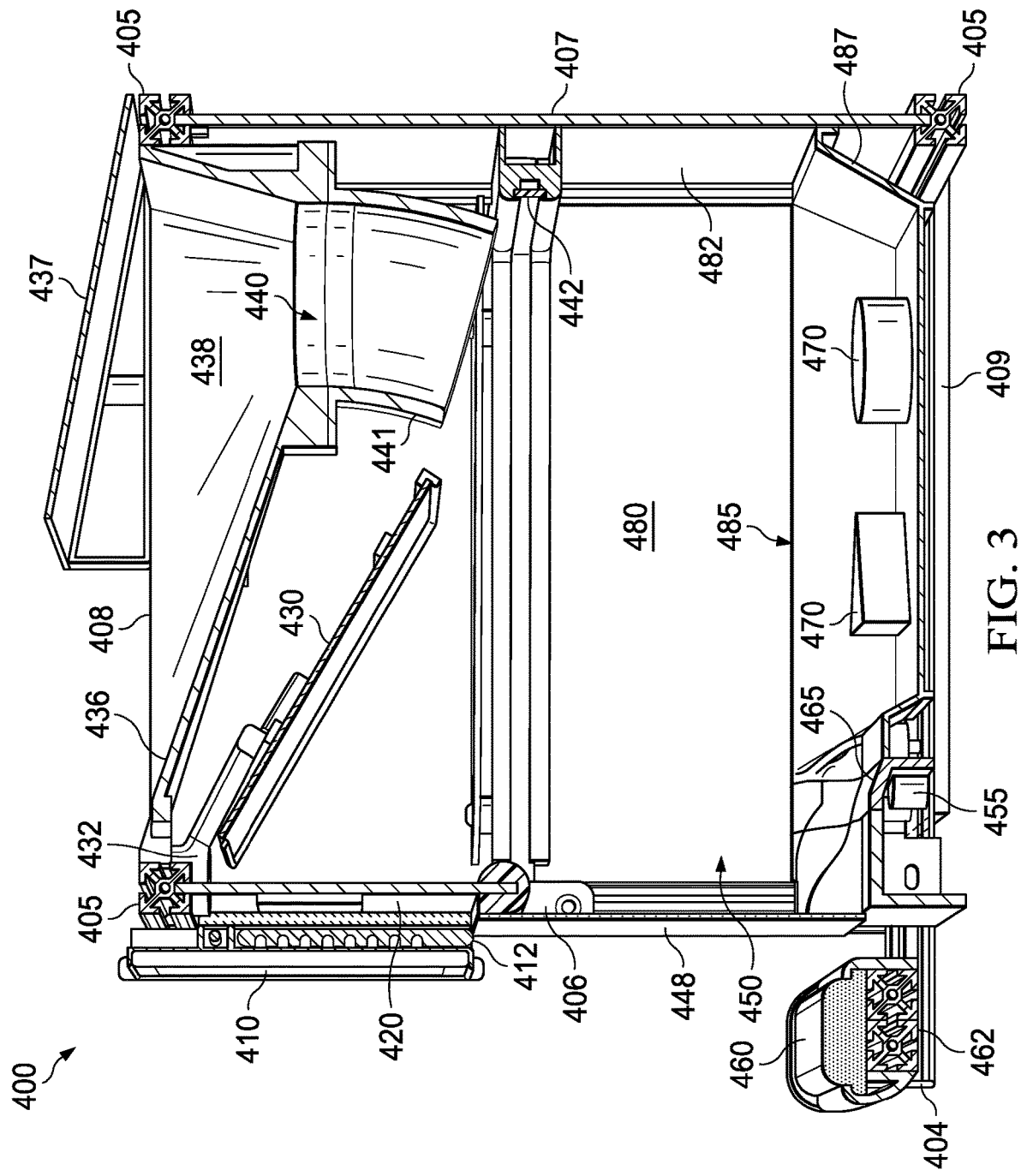
FIG. 3 is a cutaway view of a stereognosis training system according to an illustrative embodiment of the invention.

Referring to FIG. 3, a preferred embodiment of training system 400 will be described.

Training system 400 is comprised front wall 406, back wall 407, side wall 408 and floor 409. A second side wall is provided but is not shown in the cutaway view. The side walls and the floor are held in position by track railing 405. In a preferred embodiment, track railing 405 comprises an "X-bar" aluminum extrusion approximately 2" square. In a preferred embodiment, the walls and the floor are comprised are of rigid plastic material such as Teflon® or Delrin® preferably coated on the interior with a sound damping surface, such as sound dampening surface 482. The sound dampening surfaces are preferably an open cell polyurethane foam material. In other embodiments, the sound dampening surfaces may be applied as a rubberized sound dampening coating on the interior surfaces of the walls and the floor.

Figure 4:
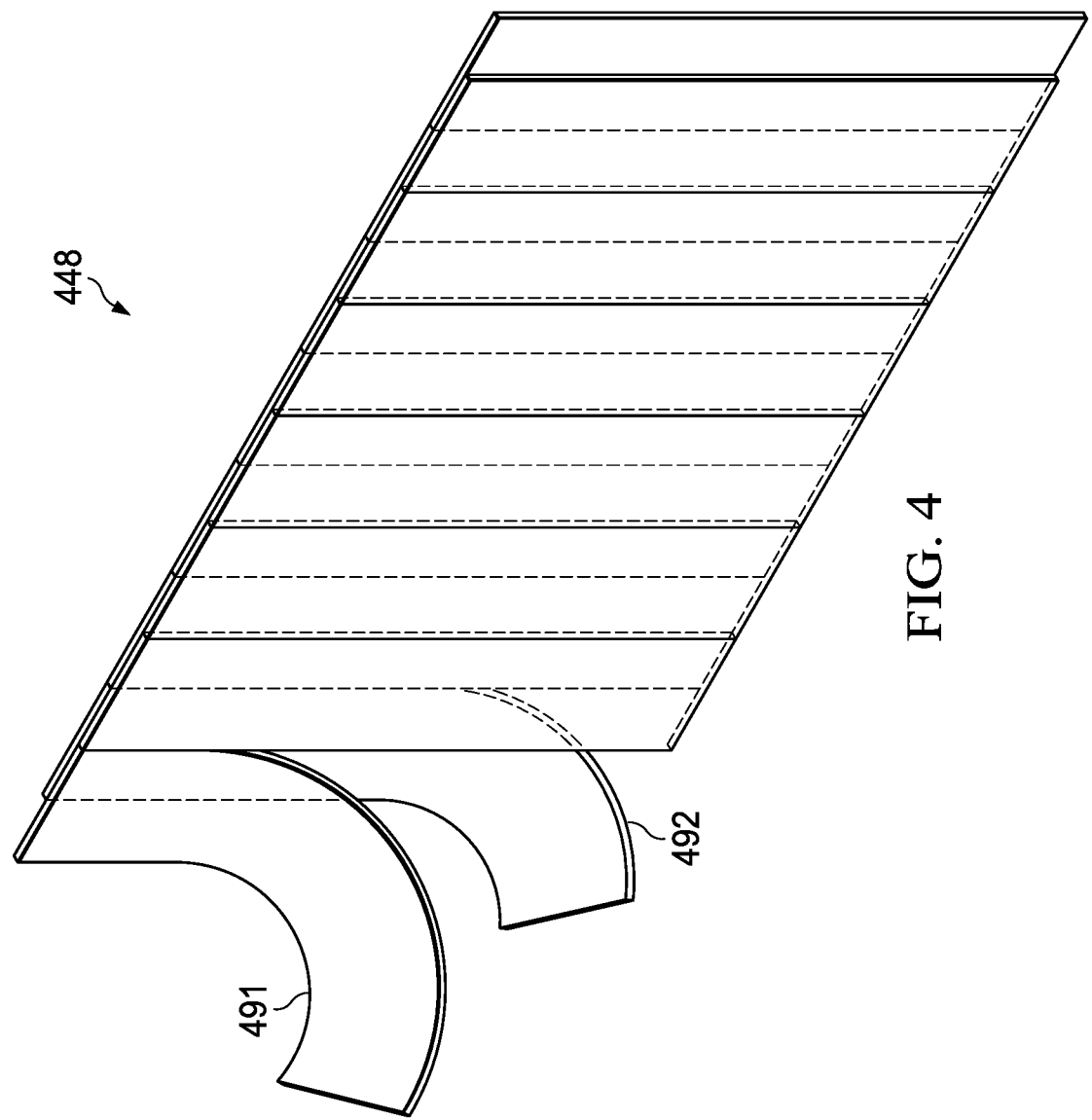
FIG. 4 is a perspective view of an offset curtain in accordance with an illustrative embodiment of the invention.

Track railing 405 further supports object entry portal 438. Object entry portal 438, in a preferred embodiment comprises a frustoconical inverted cone 436 terminating in chute 440. Hood 437 is an angular baffle attached to the side walls and back wall 407. The baffle serves to direct objects downward toward the chamber. The hood also prevents light from entering chamber 480 and prevents the patient from a line of sight into the interior of removable container 485. Chute 440 forms a curved directional surface 441 directed toward chamber 480. The walls and the floor when connected form a light tight chamber. Positioned within light tight chamber 480 is removable container 485. Removable container 485 is positioned within chamber 480 adjacent horizontal placement guide 455 adjacent front wall 406 and floor 409. Front wall 406 further comprises opening 450 adjacent horizontal placement guide 455. Opening 450, in a preferred embodiment is covered by offset curtain 448. Offset curtain 448 in a preferred embodiment includes overlapping flaps 491, and 492, as shown in FIG. 4, as will be further described.

Horizontal ring light 442 is held in position above removable container 485 by track railing 405. In a preferred embodiment, ring light 442 circles the interior periphery of the box and is comprised of white LED illumination of approximately 6000° Kelvin color temperature. The frequency of light is important because, it must fully and evenly illuminate blocks of different colors in order to provide an accurate reflection of each color. Front wall 406 further supports bracket 412. Bracket 412 further supports computing device 410. Adjacent bracket 412 is transparent window 420. Transparent window 420 is held directly adjacent computing device 410 by bracket 412. Computing device 410 further comprises a processor and a camera, which will be further described. The camera (not shown) is positioned by bracket 432 toward mirror 430. Mirror 430 directs light from objects 470 to the camera. In a preferred embodiment, mirror 430 is placed at approximately a 30° angle with respective to floor 409.

Adjacent opening 450 on horizontal placement guide 455, is blue bar 465. Blue bar 465 includes, in a preferred embodiment, a blue anodized reflective surface having a defined color temperature and a defined pixel count, as seen by the camera and computing device 410.

Base rail 404 supports arm rest 460 adjacent opening 450. Arm rest 460 is supported on the base rail by adjustable bracket 462. Adjustable bracket 462 enables movement of arm rest 460 toward and away from opening 450 to accommodate different patients. In a preferred embodiment, adjustable bracket 462 is fixed to base rail 404 by a releasable toggle, not shown.

Removable container 485 includes antibounce pad 487 sufficient to prevent objects 470 from moving when dropped through chute 440.

In a preferred embodiment, computing device 410 further comprises integrated components of a mobile device, such as a smartphone, tablet or laptop.

Referring to FIG. 4, offset curtain 448 will be described. In a preferred embodiment, offset curtain 448 comprises opposing sets of flaps, such as flap 491 and 492. The flaps are offset in a such a fashion that when a hand is inserted, they completely block light from exiting chamber 480 from opening 450.

Figure 5A:
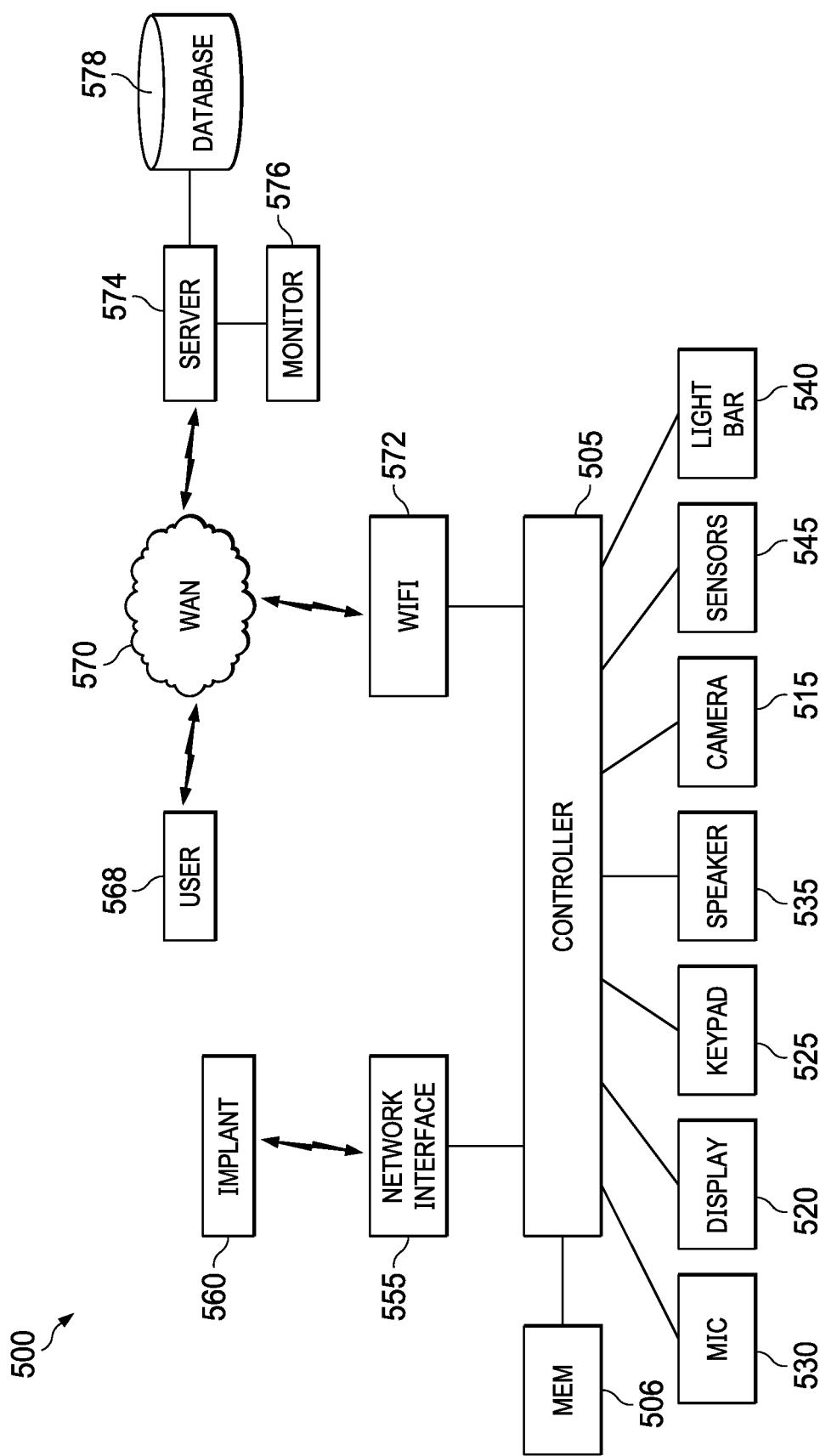
FIG. 5A is a network diagram of a system for a stereognosis training system according to an illustrative embodiment of the invention.

FIG. 5A is an architecture diagram of embodiment 500 of a computing device preferred for use in the system. Controller 505 is connected to microphone 530, HDMI display 520, keypad 525, speaker 535, camera 515, sensors 545, light bar 540 and memory 506, as will be further described.

Controller 505 is further connected to network interface 555 which wirelessly communicates with implant 560. Controller 505 communicates to wide area network 570, such as the Internet, through Wi-Fi adapter 572. Controller 505 communicates through the wide area network to user device 568 and server 574.

Server 574 is connected to monitor 576 and database 578.

Controller 505 draws program instructions for operation and communication functions from memory 506.

Implant 560 preferably is ReStore Wireless Vagus Nerve Stimulator available from Teliatry.

Figure 5B:
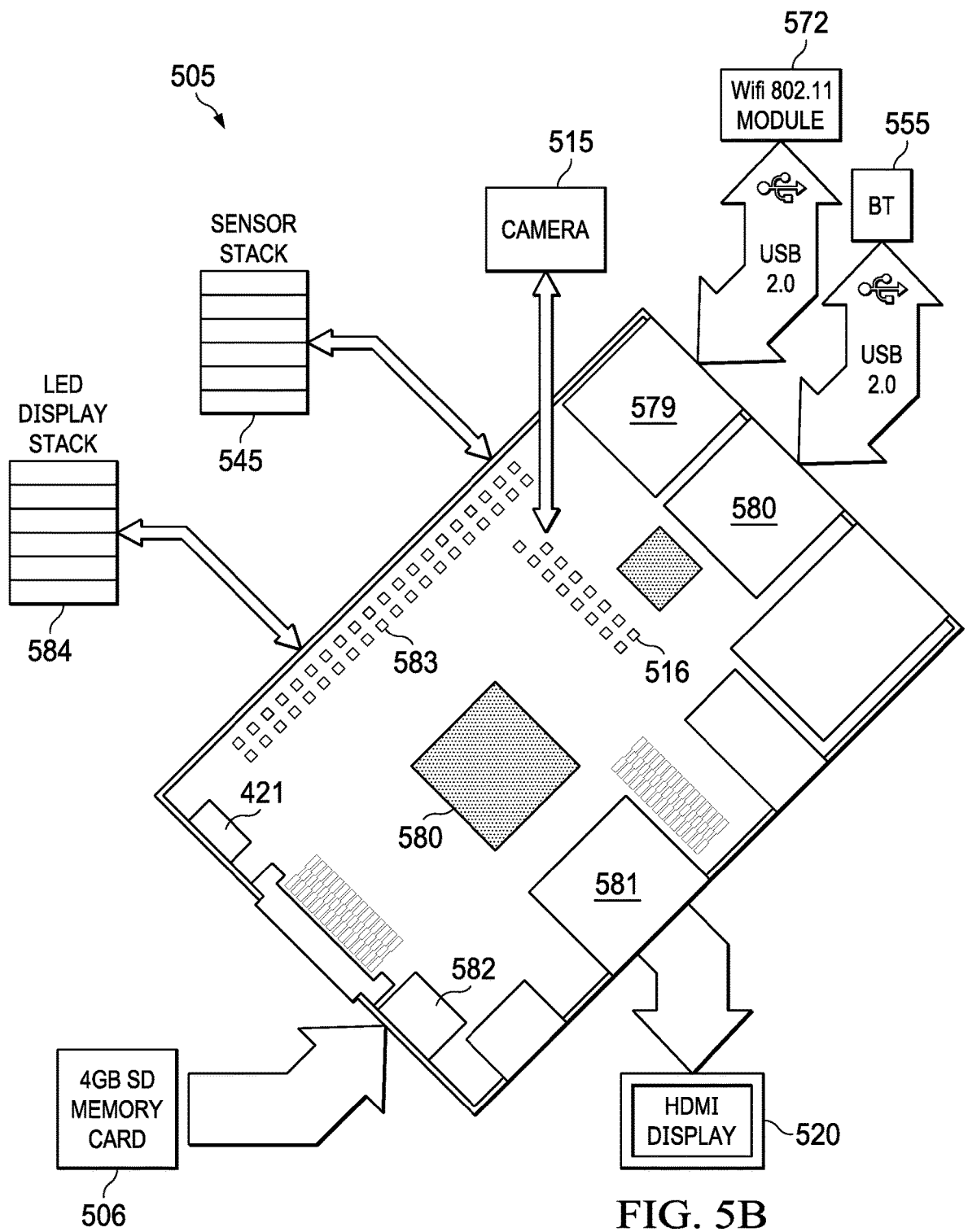
FIG. 5B is a schematic diagram of a computer system architecture for a stereognosis training system according to an illustrative embodiment of the invention.

Referring then to FIG. 5B, a preferred embodiment of controller 505 will be described. In a preferred embodiment, the controller is a dedicated Raspberry Pi 3 Model B available from Adafruit Industries. The controller includes processor 580. In a preferred embodiment, processor 580 is a Broadcom BCM 2837 1.2 GHz Quad-Core processor. Controller 505 includes two USB 2.0 ports 579 and 585. USB port 579 is connected to Wi-Fi adapter 572 which provides local Internet connection. In one embodiment, USB port 585 is connected to keypad 525. In another embodiment, USB port 585 is connected to a Bluetooth communication module or network interface. Wi-Fi adapter 572 in a preferred embodiment is Product ID 1012 USB Wi-Fi module 802.11 B/G/N available from Adafruit. In a preferred embodiment, network interface 555 is a Bluetooth RF transceiver, such as HC-11 Module 433 MHz wireless Bluetooth module available from Alibaba at www.alibaba.com.

Controller 505 further includes HDMI adapter 581 connected to HDMI display 520. In a preferred embodiment, HDMI display 520 includes integrated microphone 530, speaker 535 and keypad 525. Controller 505 includes processor 580 connected to memory card 506 via access slot 582. Controller 505 further includes GPIO connector 583. Sensor stack 545 includes optical sensors positioned adjacent opening 450, as previously described. LED display stack 584 is operatively connected to the processor through GPIO connector 583. Sensor stack 545 and LED display stack 584 are both operatively connected to the processor through the GPIO connector. In a preferred embodiment, the sensor stack includes optical detectors having both an LED and phototransistor onboard. In a preferred embodiment, the sensor stack includes four QRD 1114 optical detectors available from Sparkfun at www.sparkfun.com. The optical detector provide reflective sensitivity without the need for separate phototransistors and LED's. In another preferred embodiment, sensor stack includes a fully automatic PIR motion sensor such as Vithal HC-SR501 available from Alibaba at www.alibaba.com. LED display stack 584 further comprises an array of white LED's connected through current limiting resistors to GPIO connector 583. Camera 515 is connected to dedicated video connector 516 from which it communicates with processor 580.

Instructions stored in memory card 506 and executed by processor 580 cause processor 580 to interact with the system. Processor 580 receives software updates from server 574 through Wi-Fi adapter 572. The processor communicates with user device 568 also through Wi-Fi module 572, as will be further described.

In a preferred embodiment, processor 580 is coupled to a remote application server via the wide area network. A database is coupled to the remote application server. The remote application server and its associated database can be accessed by processor 580 and/or by a remote clinical device via wide area network 570.

FIGS. 6A-6G provide illustrative embodiments of object sets, however the invention is not limited by the object sets shown. Many other embodiments of object sets are possible. Some primary considerations for selecting object sets are: (1) for tactile sensory dysfunction, object sets map to tactile sensory functions, (2) for more severe brain injury or stroke, objects sets include real world objects, and (3) for peripheral and somatosensory dysfunction object sets map to the specific sensory features that are most impaired. In one embodiment, each object set relates to a different tactile sensory function and each object set has a distinctly different color so that the sets can be kept separate and easily identified in the directions and feedback given to the patient.

Figure 6A:
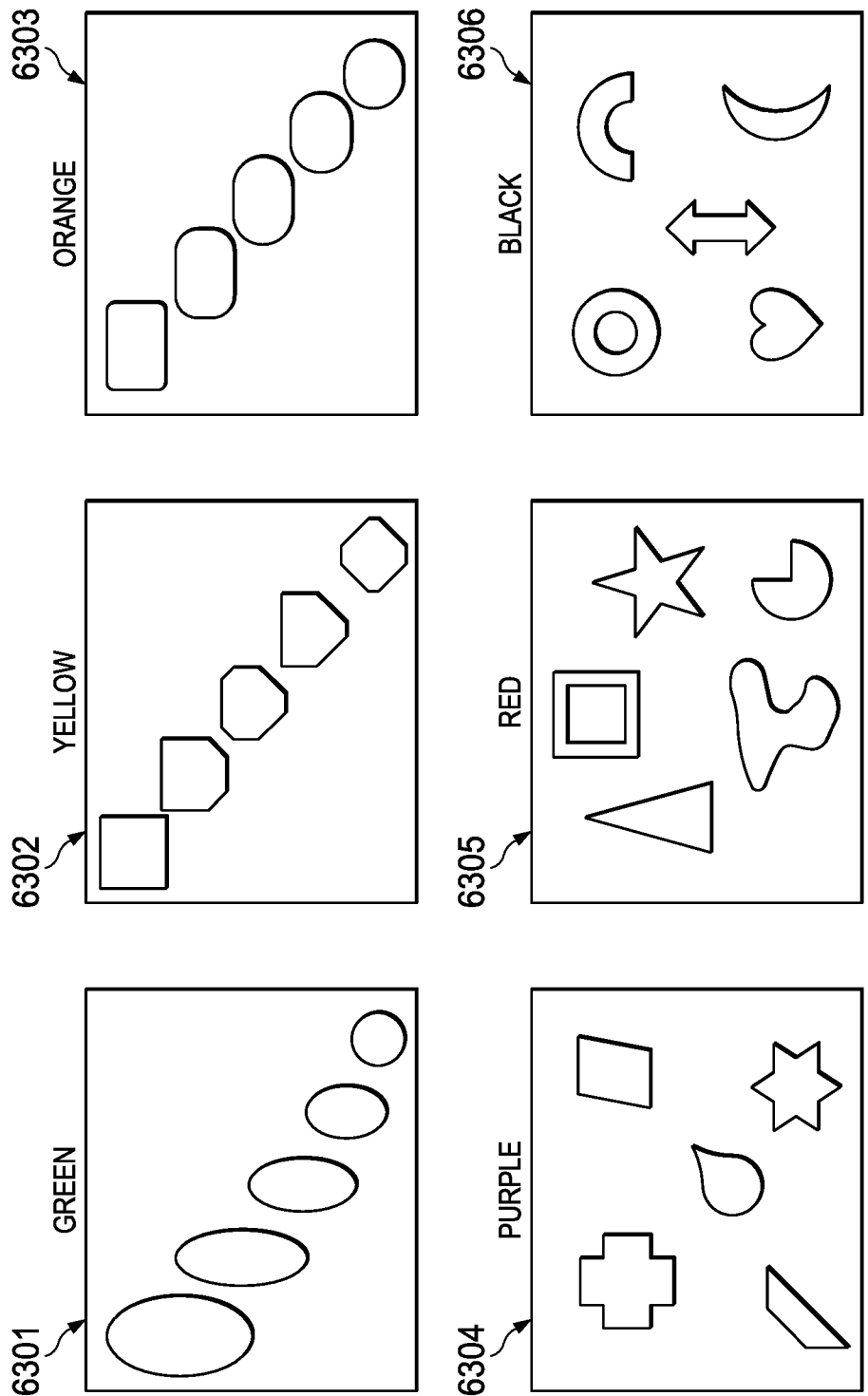

For example, in FIG. 6A, green set 6301 is for size discrimination, yellow set 6302 is for shape discrimination, orange set 6303 is for contour discrimination, purple set 6304, red set 6305 and black set 6306 are for profound sensory loss where multiple features are needed to discrimination between objects. In some embodiments, object sets of differing color relate to the difficulty of tactile recognition.

Figure 6B:
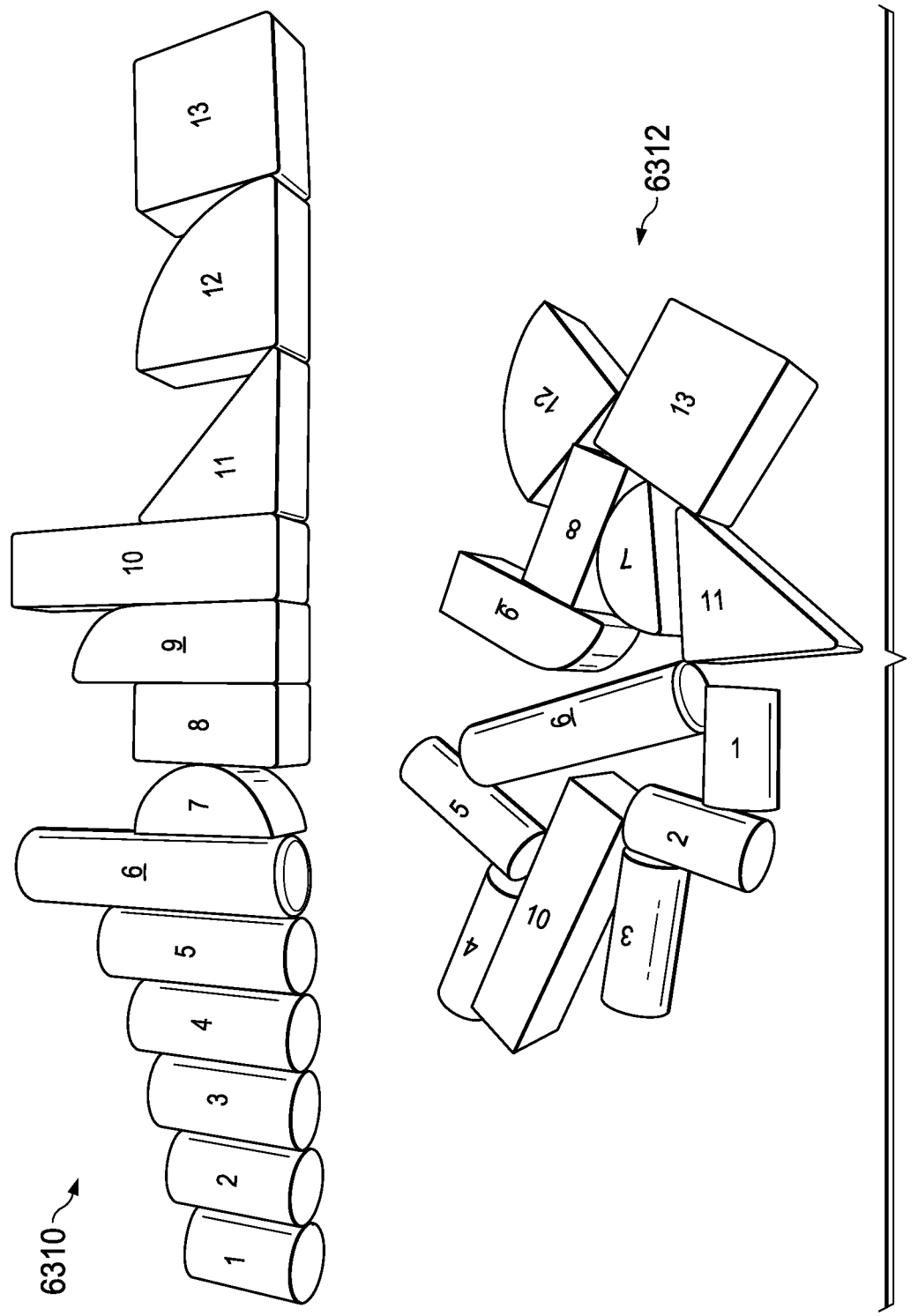

In FIG. 6B, further exemplary sets of objects are shown as 6310 and 6312. In example 6310, objects may be constructed of wood, for example, and be numbered according to size, shape and function. In example 6312, a randomized arrangement of the set of objects is shown.

Figure 6C:
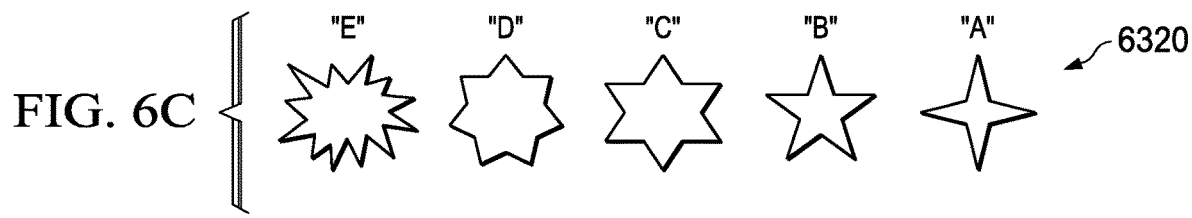

In FIG. 6C, a further exemplary set of object shapes 6320 is shown. In this example, the numbers of "points" on each object increases from right to left. As can be seen, object "A" includes four points. Object "B" includes five points. Object "C" includes six points. Object "D" includes seven points. Object "E" includes twelve points. A typical task for a patient with object set 6320 would be to locate the object with a specific number of points within a specific time limit.

Figure 6D:
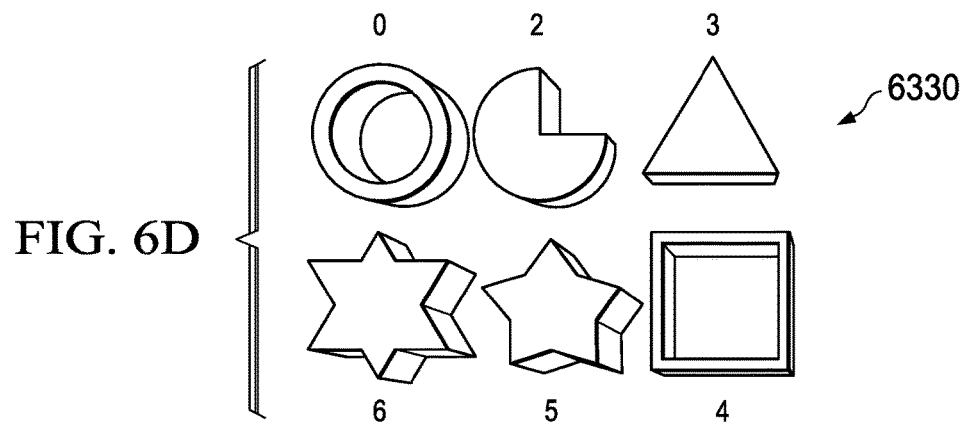

In FIG. 6D, a further exemplary a set of objects 6330 is shown. In this example, both solid and hollow objects are included in the object set. Set 6330 may be 3D printed as those shown or constructed of other materials or by other methods, for example, flexible or rigid injection molded polyvinyl chloride. A typical task for a patient with object set 6330 would be to locate either a hollow or solid shape within a specific time limit.

Figure 6E:
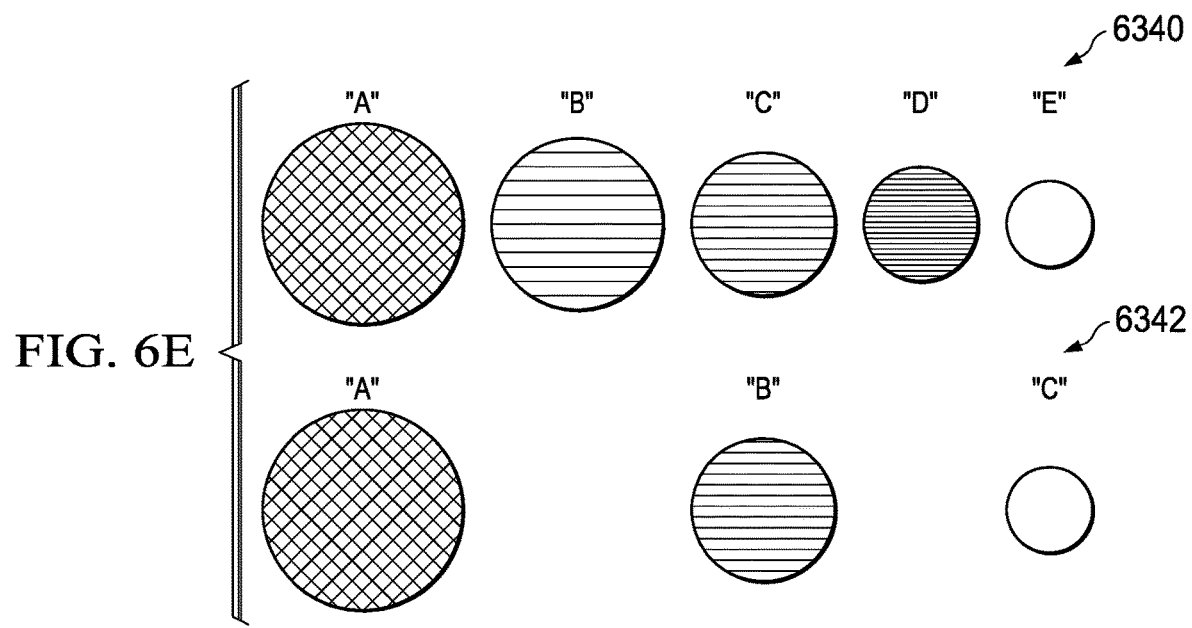

In FIG. 6E, a further exemplary set of spherical objects 6340 varying in size and texture. Set 6340 is designed to test dual tactile sensory function. Set 6340 includes large ball "a" with diamond shaped indentions, smaller ball "b" with fine lines, medium ball "c" with medium thickness lines, small ball "d" with very fine lines and small smooth ball "e". An illustrative task with set 6340 would be to locate the balls in ascending or descending order according to size. Set 6340 would be considered a "difficult" object set because the differences between the sizes is small.

A further exemplary set of objects 6342 is shown in FIG. 6E. Set 6342 includes three objects, large ball with diamond shaped indentions "a", medium ball with medium thickness lines "c" and small ball and smooth ball "c". Set 6342 would be considered "easier" than set 6340 because the differences in sizes and textures between the balls is more significant.

Figure 6F:
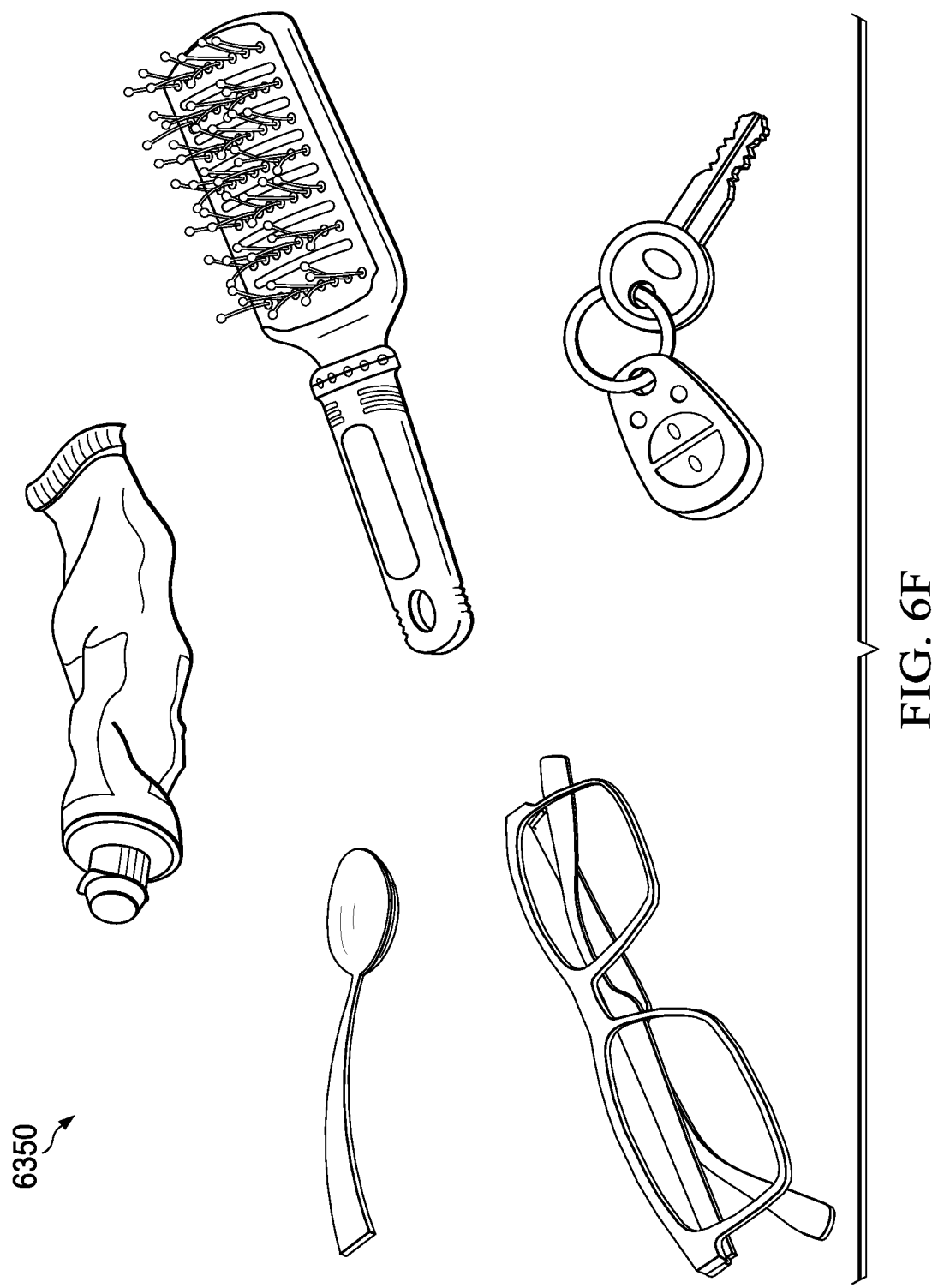

FIG. 6F shows a set of real world objects 6350 that may be used with the invention. Set 6350 includes everyday objects with very different shapes and textures which can be used for profound stereognosis deficits. An illustrative task with set 6350 would be to find the glasses, find the brush, then find the keys.

FIG. 6G shows multiple sets of objects for an illustrative embodiment of a stereognosis training method. Object set 6361, object set 6362 and object set 6363 include three objects of decreasing degree of tactile recognition between the objects included the set. For example, object set 6361 has objects that are very distinct in tactile recognition whereas object set 6363 has three objects that are less distinct and more difficult to distinguish in tactile recognition. Objects set 6364, object set 6365 and object set 6366 include more than three objects of varying tactile recognition, with the most recognizable differences in object set 6364 and the least recognizable differences in object set 6366.

A stereognosis training method is prescribed at step 6370 to begin stereognosis training prescribing tasks using sets of three objects with distinctly different shapes and texture, including for example, smooth/hard, heavily textured, soft/pliable shapes. At step 6371, the method proceeds to prescribe tasks with more challenging objects that differ in fewer properties or with less distinction in tactile recognition than in step 6370. Step 6372 proceeds to prescribe tasks with more objects of a mixed distinction and difficulty in tactile recognition.

Stereognosis deficits can result from one or more of poor motor control, poor proprioception (joint position) and poor tactile sensation (touch). Object differences can be designed to require judgement of a single feature or a combination of features (as in everyday objects). Differences between objects in an object set will be adjusted to create uniform differences in difficulty.

FIGS. 7A-7D show examples of object sets that exhibit varying degrees of difficulty in a single parameter. In this example, the objects vary only in length and color. For example, object 701 is the shortest, while object 705 is the longest. The weight, texture and shape of the objects is held constant. In a preferred embodiment, each of the objects varies in density so that its weight is the same, approximately 500 grams. The objects vary by ½" each and range from 2" to 4" in length.

Object 701, object 702, object 703, object 705, and object 704 can be divided into sets of differing difficulty based on their relative lengths.

Figure 7A:
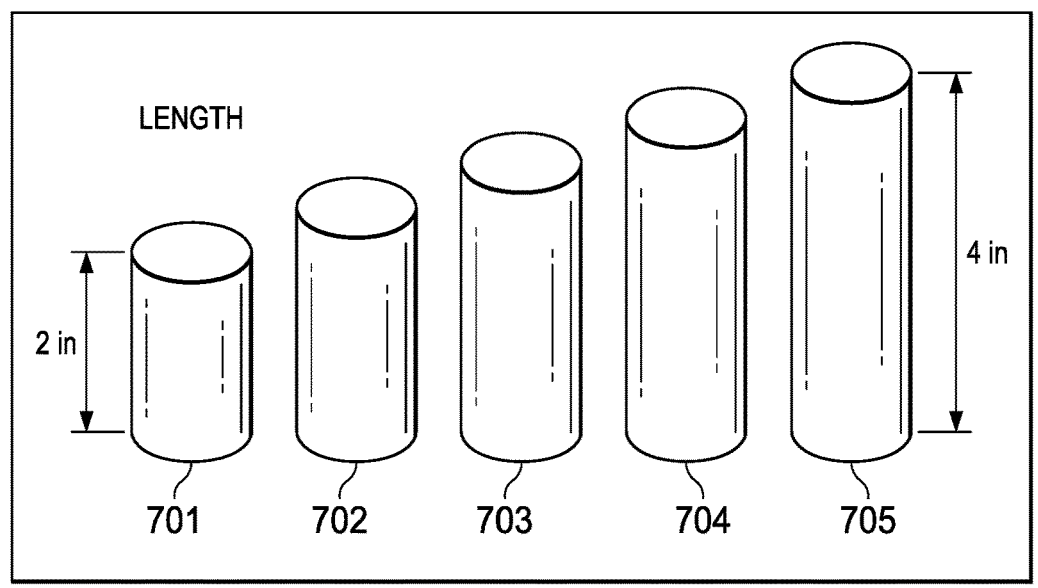
FIGS. 7A-7D are schematic diagrams of object sets that exhibit varying degrees of difficulty in a single parameter in accordance with illustrative embodiments of the invention.
Figure 7B:
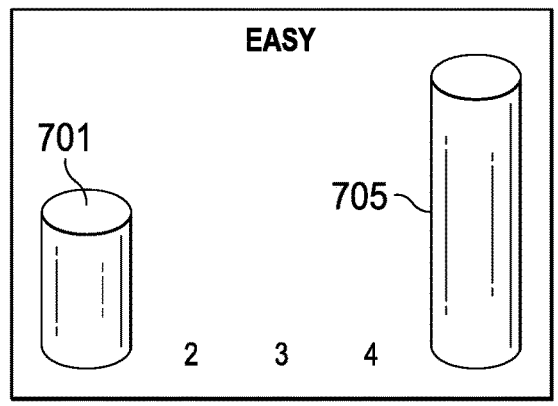

FIG. 7B shows an "easy" difficulty set comprised of object 701 and object 705, which exhibit the greatest difference in length, thereby being the easiest to recognize.

Figure 7C:
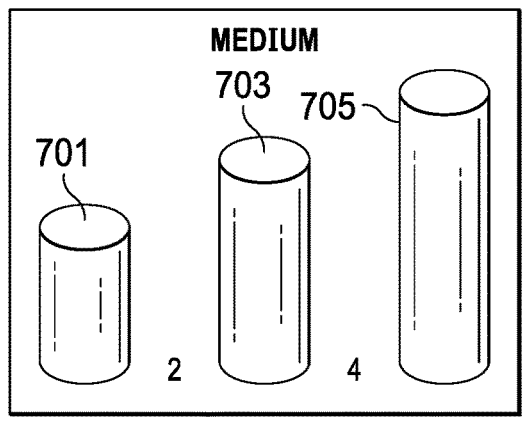

FIG. 7C shows a "medium" difficulty set comprised of object 701, object 703 and object 705. The objects in this object set are more difficult to tell apart because the differences in length are smaller.

Figure 7D:
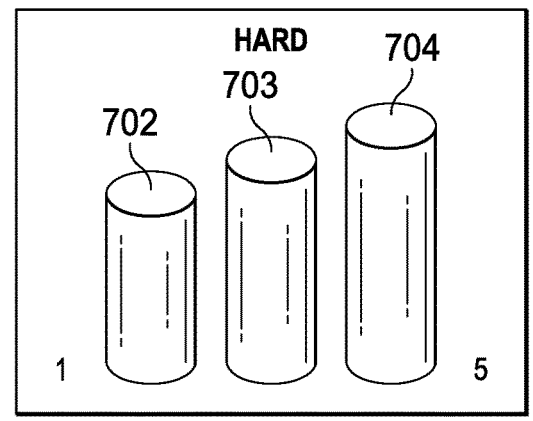

FIG. 7D shows "hard" difficulty set comprised of object 702, object 703 and object 704. These objects are the most similar in length and hence the most difficult to tell apart.

In FIG. 8A, a further exemplary set of objects is shown. A table of four object sets. The set of objects 800 can categorized into several subsets according to length, texture, shape and weight. Row 801 identifies subsets of objects based on length. The basic shape for the subset of row 801 is a cylinder. Row 802 identifies subsets of objects based on texture. Row 803 identifies subsets of objects based on shape. Row 804 identifies subsets of objects based on weight. The subsets of objects may be further categorized by basic object 805, type 806, difficulty ranges "easy" 807, "medium" 808 and "hard" 809 and range of difficulty column 810, and Somatosensory Receptor column 827.

The subsets of objects are further identified by color. Each subset of two objects include two different primary colors. In one preferred embodiment, these colors are red and green. In subsets of objects including three objects, three different primary colors are applied. In a preferred embodiment, these three primary colors are red, yellow and green. The objects in each subset are required to be different colors so that they may be differentiated by the computer system.

The basic object for subsets in row 801 can be seen to be a cylinder. The basic object for the subsets in row 802 can be seen to be a "tri-toroid". The basic shape for objects in row 803 can be seen to be flat and three dimensional. The basic shape of objects in row 804 are seen to be generally cylindrical. The basic shapes for each row of object subsets can change so long as each of the basic shapes remains constant for each subset in each row.

Referring then to row 801, subset 811 is comprised of two cylindrical objects which range in length from 2" to 4". Subset 811 is categorized as "easy." Subset 812 is comprised of three objects ranging in length from 2" to 3" to 4". Subset 812 is categorized as "medium" in difficulty. Subset 813 is comprised of three cylindrical objects ranging in size from 2.5" to 3" to 3.5". Subset 813 is categorized as "hard" in difficulty. The primary receptor type stimulated 828 for row 801 objects is mechanoreceptor Ruffin endings.

Referring to row 802, subset 815 is comprised of two tri-toroidal objects having textures "a" and "b". Texture "a" includes a range between features of about 0.045 cm². The texture of object "b" includes a different texture with a range between features of about 0.045 cm². Subset 815 is characterized as "easy" in difficulty. Subset 816 comprises three tri-toroidal objects having textures "a", "b" and "c", respectively. Texture "a" and texture "c" have a range between features of feature of about 0.09 cm². Object "b" has a smooth texture and therefore is designated as a feature size of 0. Subset 816 is characterized as "medium" in difficulty.

Subset 817 comprises three tri-toroidal objects having textures "a", "b" and "c". The texture frequency of texture "a" is approximately about 0.045 cm². The texture frequency of texture "c" has a feature size of about 0.045 cm². The texture "b" is smooth and therefore is characterized by a feature frequency of 0 cm². Primary stimulation type 829 for row 802 objects is mechanoreceptor Meissner corpuscles.

Referring then to row 803, object subset 818 is comprised of two objects. In this example, the objects comprise of flat, three dimensional cylinder and a flat three dimensional triangle. Subset 818 is comprised as "easy" in difficulty. The range of points in subset 818 is 0 and 3. Subset 819 is comprised of three objects. The shapes of the objects comprise a flat three-dimensional cylinder, a flat three-dimensional square and a flat three-dimensional triangle. Subset 819 is characterized as "medium" in difficulty. The range of points in subset 819 is 0, 3 and 4. Subset 820 is comprised of three objects, a flat three-dimensional hexagon, a flat three-dimensional square and a flat three-dimensional five pointed star. Object subset 820 is characterized as "hard" in difficulty. The primary receptor type stimulated 830 for row 803 objects is mechanoreceptor Merkel's disks.

Range 814 indicates that the objects in row 801 can have a range in length between 2" and 4". Range 824 indicates that the objects in row 802 can vary between 0 and 0.09 cm² in feature size. Range 825 indicates that the object in row 803 can vary between 0 and 6 points. The objects in line 804, range between 42 and 85 grams.

Referring then to row 804, subset 821 is comprised of two objects. Objects weighing 42 grams and an object weighing 85 grams. Subset 821 is categorized as "easy" in difficulty. Object subset 822 is comprised of three objects. One object weighs 42 grams, one object weighs 64 grams and one object weighs 85 grams. Subset 822 is characterized as "medium" in difficulty. Subset 823 is comprised of three objects, one weighing 53 grams, one weighing 64 grams and one weighing 74 grams. Object subset 823 is characterized as "hard" in difficulty. The primary receptor type stimulated 831 for row 804 objects is proprioceptor.

The object subsets in row 801 are each of equal weight, have the same texture, and have the same shape. Each of the objects and each of the subsets varies only by length.

The objects in row 802 are of the same length, shape, and weight and vary in only texture.

The objects in row 803 are of the same length, are the same general size, texture and weight and vary only in shape.

The object subsets in row 804 are the same length, texture and shape and vary only in weight.

As can be seen, the object subset allow only one parameter, namely length, texture, shape or weight to vary within each subset.

Referring to FIG. 8B, an exemplary subset of objects will be described. This subset comprises object 850 and object 890. The two objects are the same size, the same weight, the same texture but different colors. In a preferred embodiment, object 850 is red and object 890 is green. The single parameter varied between these objects is tactile vibration. Hence, the primary receptor stimulated is Pacinian corpuscles.

Object 850 is comprised of body 858 which includes hollow internal chamber 851. Internal chamber 851 includes motor 852 operatively connected to off center weight 854 by shaft 853. Motor 852 is operatively connected to battery 855 and switch 856. When switch 856 is activated, current is supply from the battery to the motor thereby rotating the off center weight in order to create a vibration. In a preferred embodiment, motor 852, shaft 853 and off center weight 854 are available prepackaged as a vibration motor available from Uxcell. In this embodiment, the motor is three fold motor weighing approximately 24 grams and vibrating at approximately 1,000 rpm. Battery 855 comprises a three volt lithium battery weighing approximately 35 grams. Switch 856 is single pole single throw switch weighing approximately 2 grams. Body 858 in this embodiment weighs approximately 20 grams. The total weight of object 850 then is approximately 81 grams.

Object 890 comprises body 888 and centrally located weight 891. Body 888 weighs approximately 20 grams. Central weight 891 weighs approximately 61 grams. In a preferred embodiment, body 858 and body 888 are both comprised of brightly colored polypropylene plastic. Weight 891 is comprised of a light zinc alloy.

Figure 8C:
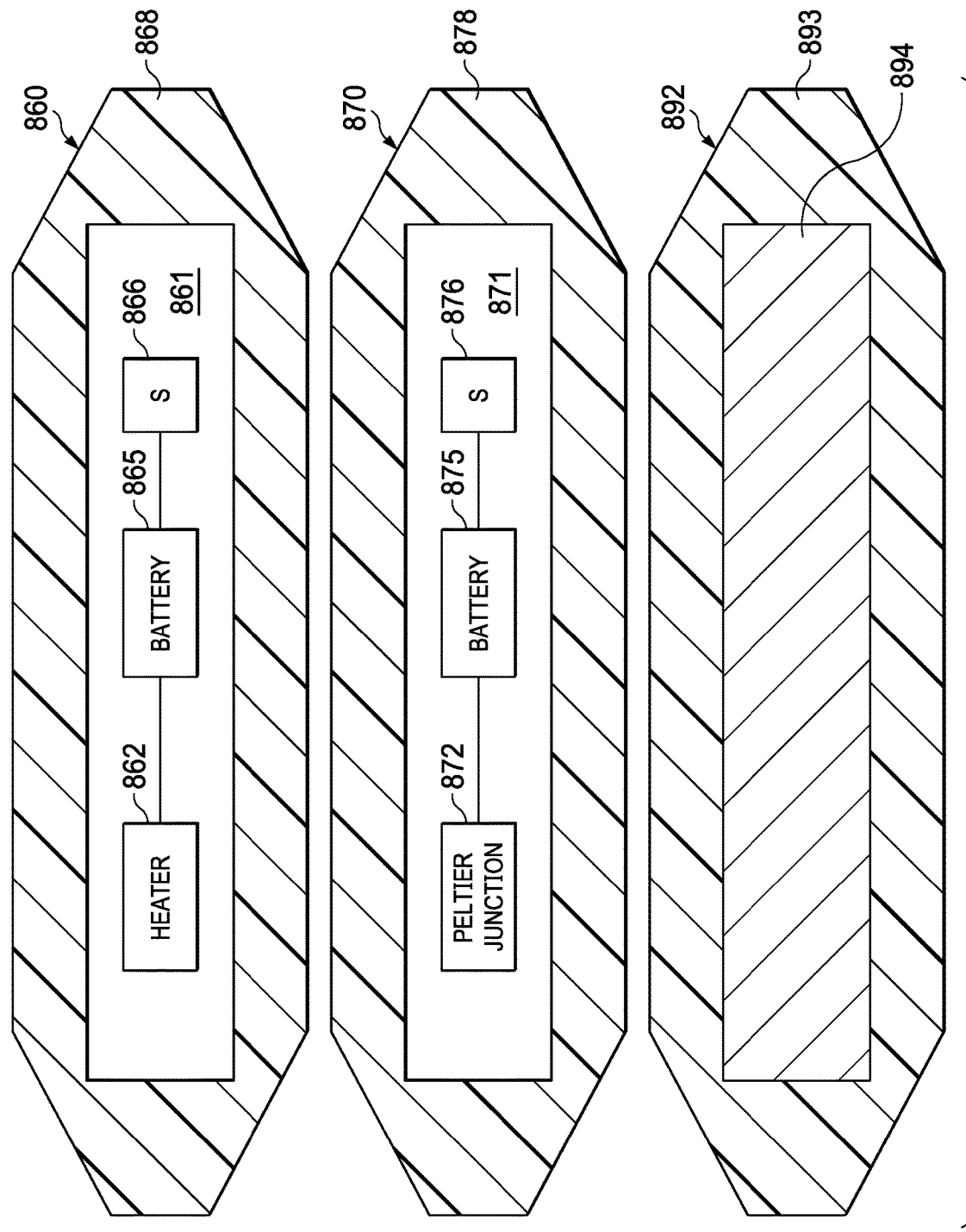
FIG. 8C is a schematic drawing of a cutaway view of an exemplary object set.

Referring to FIG. 8C, an exemplary subset of objects will be described. This subset comprises object 860, object 870 and object 892. The three objects are the same size, the same weight, the same texture, but different colors. In a preferred embodiment, object 860 is red, object 870 is yellow, and object 892 is green. The single parameter varied between these objects is tactile temperature. Hence, the main receptors stimulated are the thermoreceptors and nociceptors.

Object 860 is comprised of body 868 which includes hollow internal chamber 861. The body is probably a light zinc aluminum alloy. Internal chamber 861 includes heater 862 operatively connected to battery 865 and switch 866. The internal chamber is backfilled with epoxy to stabilize the components. The heater is positioned against an interior surface of the internal chamber to facilitate heat transfer. In a preferred embodiment, heater 862 is a standard rectangular 1.5 volt ultrathin flexible heater Model No. TSA0100016ARO.705, 3.19 watt heater available from Pelonis Technologies, Inc. of Exton, Pa. When switch 866 is activated, current is supplied from the battery to the heater in order to increase the object's temperature. The total weight of object 860 then is approximately 95 grams.

Object 870 is comprised of body 878 which includes hollow internal chamber 871. Internal chamber 871 includes Peltier junction 872 operatively connected to battery 875 and switch 876. When switch 876 is activated, current is supply from the battery to the Peltier junction in order to decrease the object's temperature. In a preferred embodiment, the Peltier junction is a TEC-30-36-127 Peltier cooler module assembly created at 3 amps at approximately 15.4 volts available from Wakefield Thermal Solutions, Inc. of Pelham, N.H. The internal chamber is backfilled with epoxy to stabilize the components. The junction is positioned against an interior surface of the internal chamber to facilitate heat transfer. The total weight of object 870 then is approximately 95 grams.

Object 892 comprises body 893 and centrally located weight 894. Body 893 weighs approximately 20 grams. Weight 894 is comprised of a light zinc alloy with sufficient voids to demonstrate a weight of approximately 95 grams.

Figure 9:
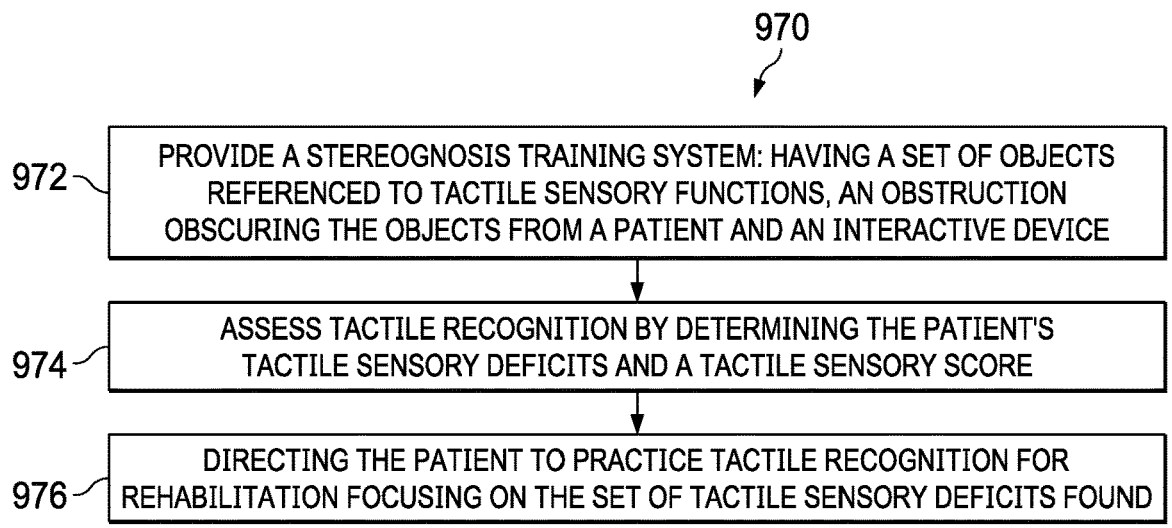
FIG. 9 is a block diagram of a method for assessment for stereognosis training and rehabilitation according to illustrative embodiments of the invention.

In FIG. 9, method 970 for stereognosis training is shown. Method 970 begins at step 972, by providing a stereognosis training system having a set of objects that stimulate a set of tactile sensory functions, an obstruction obscuring the set of objects from a patient and, optionally, an interactive device. The interactive device is preferably programmed to select a test object, direct the patient to identify and grasp the test object from the set of objects and determine if the patent correctly identified and grasped the test object.

At step 974, tactile recognition of the patient is assessed by determining a set of tactile sensory deficits of the patient and determining a tactile sensory score based on the tactile sensory deficits.

At step 976, the stereognosis system, preferably via the interactive device, directs the patient to practice tactile recognition and focusing the practice on the set of tactile sensory deficits found in step 974.

Figure 10:
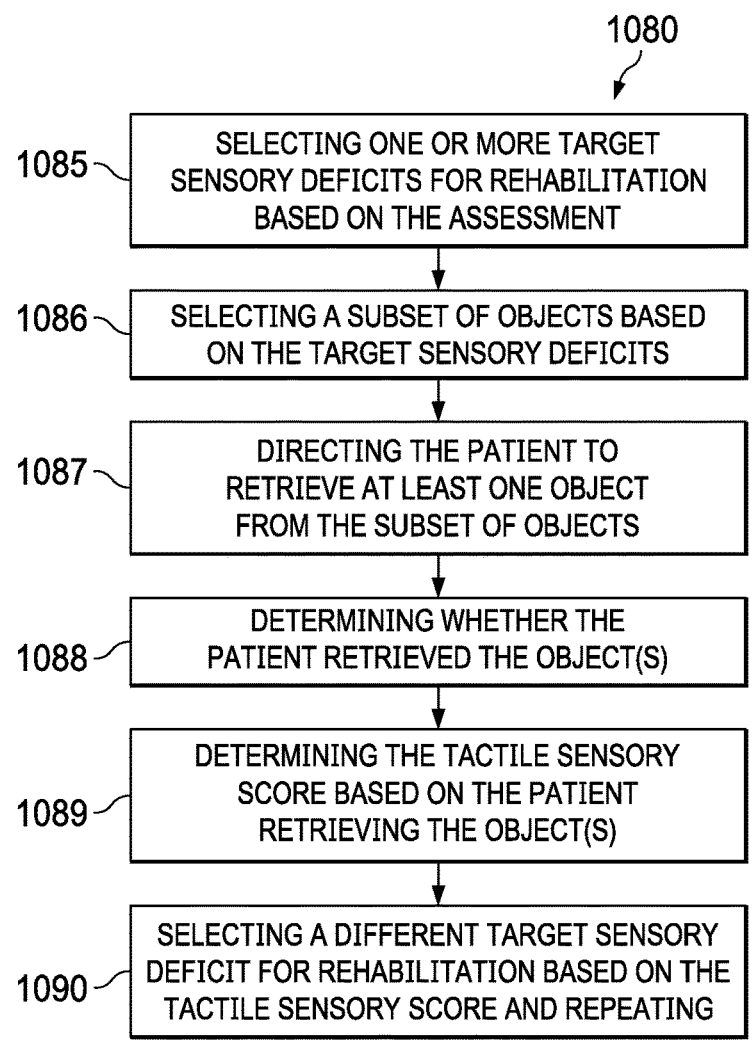
FIG. 10 is a block diagram of a method for stereognosis rehabilitation according to illustrative embodiments of the invention.

Referring to FIG. 10, a method of rehabilitation is further described as method 1080. At step 1085, one or more target sensory deficits for rehabilitation are selected based on the set of tactile sensory deficits. At step 1086, a subset of objects are selected that are known to stimulate the target tactile sensory deficits. At step 1087, the interactive device directs the patient to retrieve at least one object from the subset of objects.

A determination is made, at step 1088, as to whether or not the patient accurately retrieved the object. The determination can be made in a number of ways. In one embodiment, the interactive device displays a picture of the object. The patient then simply lifts or retrieves the object into sight and compares it visually to the picture and either presses a button on the interactive device or audibly speaks into the interactive device to provide a response that the object was correctly or incorrectly selected. The interactive device determines the response and records it. In another embodiment, the interactive device records video images of the patient's hand and the object being selected and, through image processing techniques and/or visual cues attached to the object, determines whether the object was correctly or incorrectly selected.

At step 1089, a tactile sensory score is determined based on the result found in step 1088. In one embodiment, the tactile sensory score is the percentage of correct objects found in the subset of objects, which is updated at step 1089 as each object is retrieved.

At step 1090, the tactile recognition ability of the patient is re-assessed for changes in tactile sensory deficits. For example, when the tactile sensory score for a target sensory deficit crosses a threshold, then the next highest tactile sensory deficit found in the original assessment or in a new assessment is selected as the target sensory deficit and the method repeats beginning with step 1085.

Figure 11:
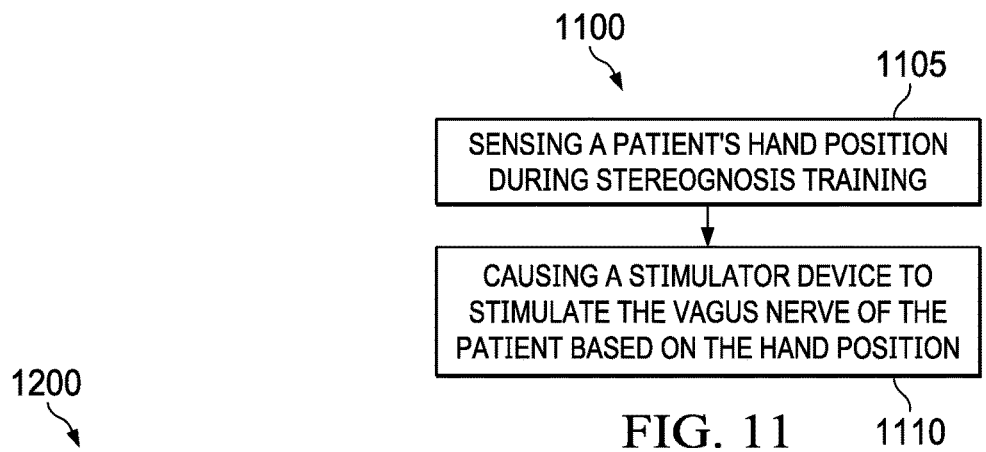
FIG. 11 is a block diagram of a method for paired therapy of external stimulation and stereognosis training according to illustrative embodiments of the invention.

Referring to FIG. 11, a method for paired therapy using the stereognosis training system is shown as method 1100. At step 1105, a patient's hand position is sensed during stereognosis training to determine if the patient's hand is engaged in searching for an object within a set of objects. Preferably the time of engagement with the set of objects and the duration of the engagement with the set of objects is determined in step 1105. At step 1110, a stimulator device, capable of stimulating the vagus nerve of the patient, stimulates the patient's vagus nerve at a prescribed time and for a time duration determined by the time of engagement with the set of objects and the duration of engagement with the set of objects. For example, the 0.5 second trains of vagus nerve stimulation is delivered during active object engagement. Stimulation is typically off for at least 5 second between stimulation events.

Figure 12:
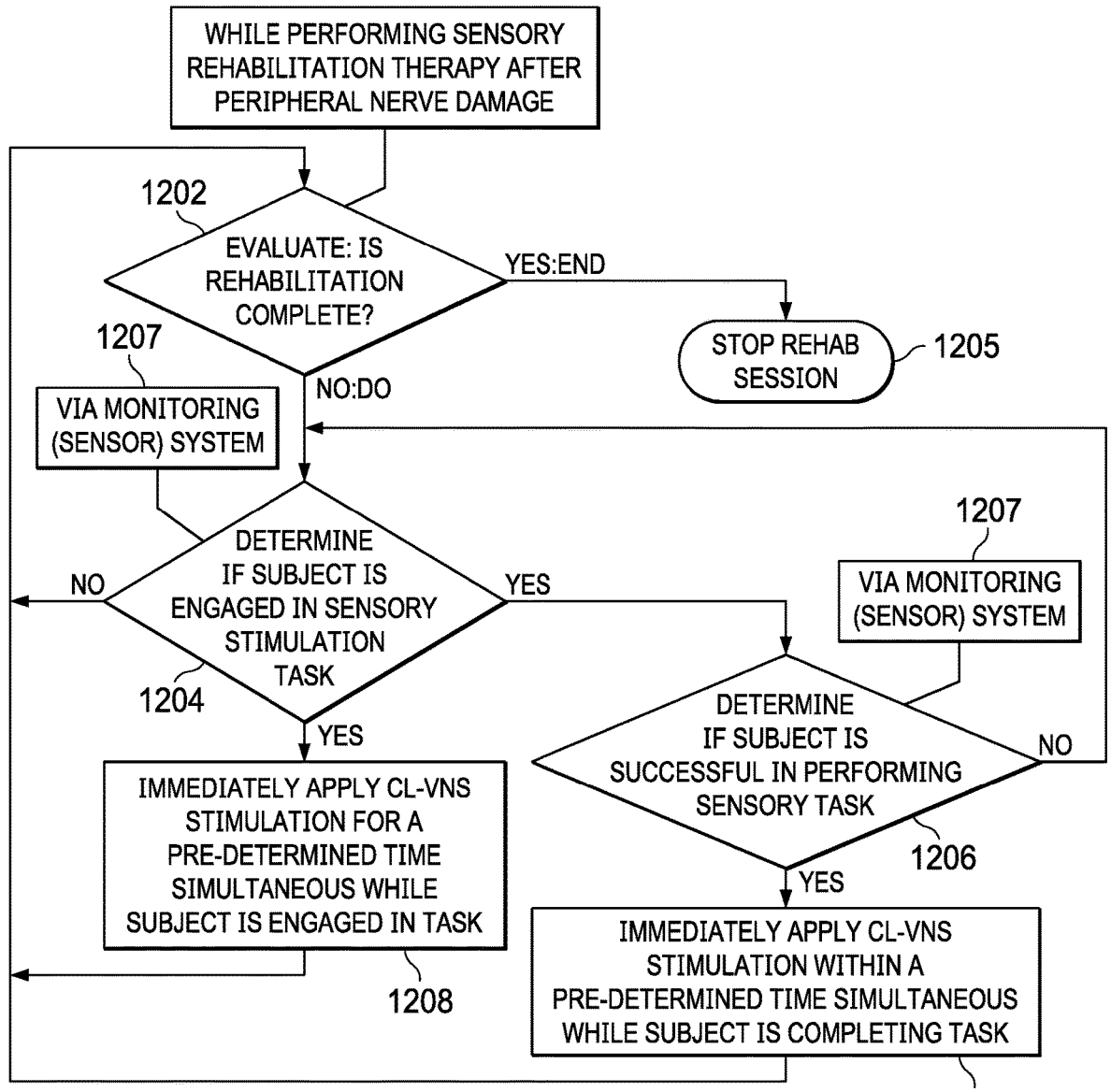
FIG. 12 is a flow chart depicting a task based sensory rehabilitation treatment method in accordance with an embodiment of the invention.

Referring to FIG. 12, a flow chart depicts CL-VNS treatment 1200 during sensory rehabilitation of a subject. Method 1200 is applicable for sensory dysfunction resulting from nerve damage and in particular, peripheral nerve damage in which one or more rehabilitation tasks of the subject's sensory network is prescribed. During a rehabilitation session, an evaluation is made at step 1202 of whether or not the session is complete. If so, the method moves to step 1205 and concludes. If not, the method moves to step 1204. A subject is required to performing a task that is monitored via a monitoring and triggering system 1207.

At step 1204, a determination is made as to whether or not the subject is engaged in performing the rehabilitation task. If so, the method moves to step 1206 and, optionally also to step 1208. If not, the method returns to step 1202.

At step 1206, the rehabilitation task may be further monitored to determine if the subject was "successful" in completing the rehabilitation task according to a pre-defined threshold for success (for example, engage a switch twice, lift an object for a given amount of time and so forth). If so, then the method moves to step 1209. If not, then the method returns to step 1204.

At step 1208, a neural stimulus is applied to the subject's vagus nerve immediately upon sensing the subject's engagement with the rehabilitation task. The method then returns to step 1202. At step 1209, a neural stimulus is applied to the subject's vagus nerve immediately upon sensing the subject's "successful" completion of the rehabilitation task. In a preferred embodiment, only step 1209 is required for vagus nerve stimulation during rehabilitation treatment. In other embodiments of method 1200, either or both of steps 1208 and 1209 may be executed. In other embodiments, the time, duration or pulse width of VNS stimulation may vary between steps 1208 and 1209.

Figure 13A:
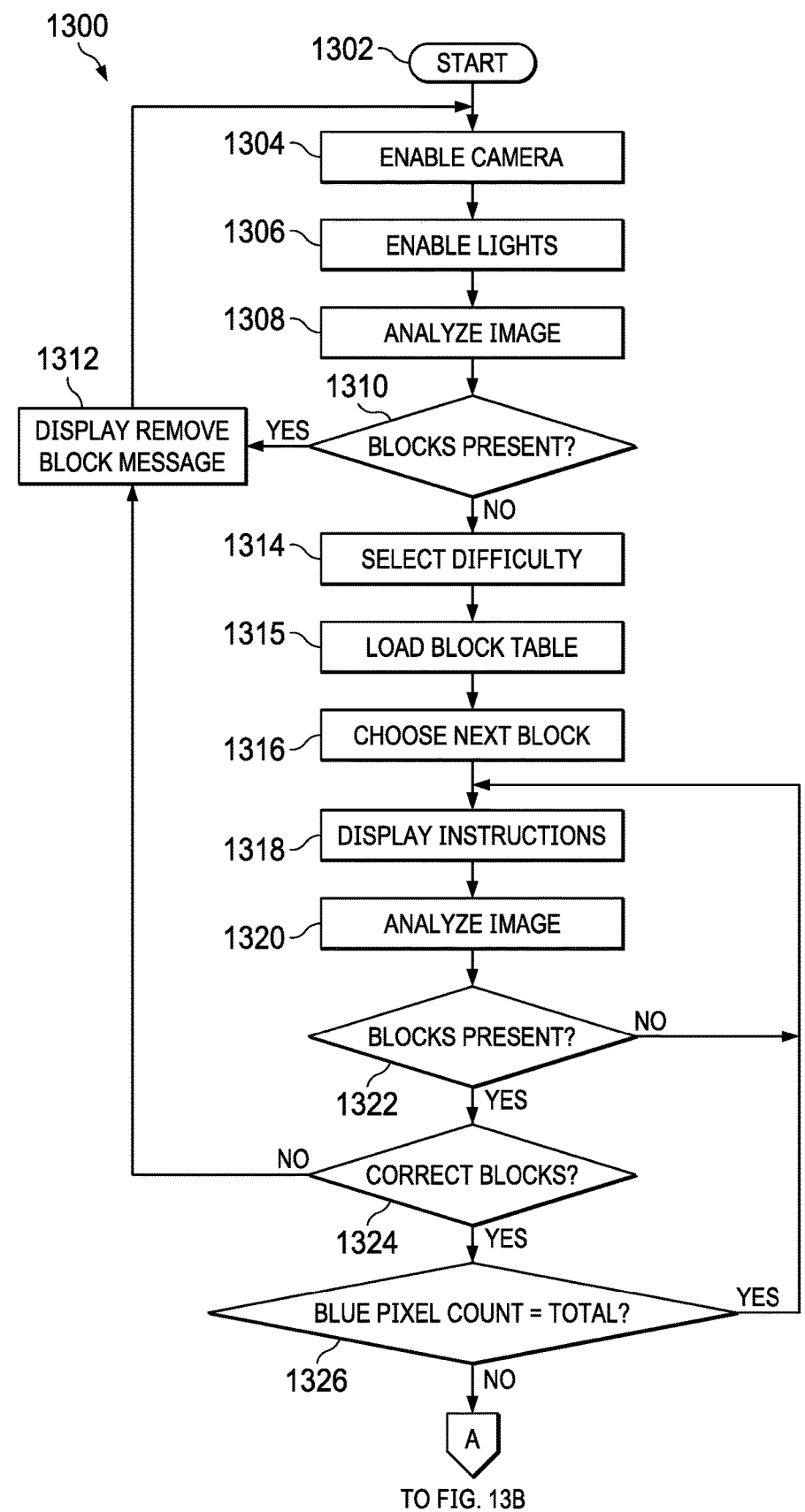
FIGS. 13A and 13B are a flow chart depicting a method of software process in accordance with an illustrative embodiment of the invention.
Figure 13B:
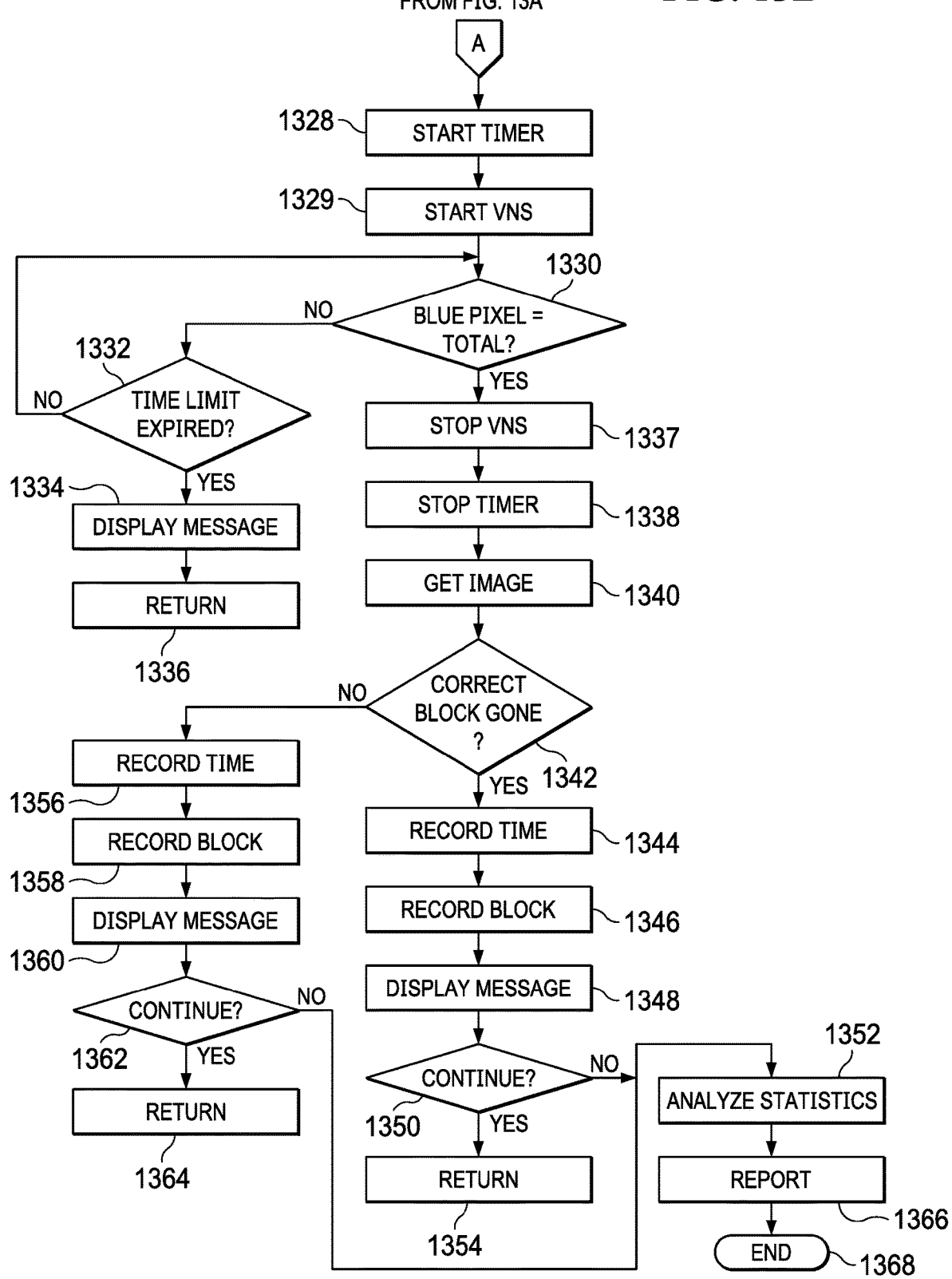

Referring to FIGS. 13A and 13B, method 1300 of a software process resident in memory 506 will be described.

In general, the sensorimotor task is both mediated and monitored by software loaded into the controller. Instructions to the operator are displayed on the screen, as well as an image of the object the participant is to retrieve. The participant then reaches into the box, finds the object by touch, retrieves it, and drops in back into the box through the chute on the top of the box. The controller uses a camera to detect the presence of the participants hand by detecting the apparent size of a blue bar adjacent the opening and color of the objects inside the box. Because each object in a set is a different color, the color is used to determine whether or not each object returned by the participant is correct. If it was correct, a new object is displayed; if not, task repeats. The software records the object set difficulty, the object target and the elapsed time between the beginning of the task and the end of the task.

At the conclusion of the sensor motor task a message is sent to the participant via text message or email that includes a report of progress. During the sensor motor task, the camera view and a running summation of progress is sent to and recommended by the server, and may be monitored by a remote computer. The summation of progress includes a table of trial and error, subject type, elapsed time per task, and average elapsed time. The server compiles statistics from all the sensor motor tasks. The controller also may send sensor motor task schedules to participants informing them of scheduled task times.

Referring then to FIG. 13A, at step 1302, the method begins.

At step 1304, the processor enables the cameras. At step 1306, the processor enables the lights interior to the box. At step 1308, the processor analyzes the image provided by the cameras. At step 1310, the processor decides whether or not blocks are present in the camera image. If so, the method moves to step 1312. If not, the process moves to step 1314. At step 1312, the processor displays a message to remove any blocks that are present in the box. The method then returns to step 1304.

At step 1314, the processor receives a selection of difficulty from the keypad.

At step 1315, the processor loads one of any number of block tables as chosen by the keypad input. A preferred embodiment of a set of block tables is shown below:

TABLE 1

EASY

| Block ID | Pixel Count | Color |
|---|---|---|
| A1 | 100 | Red |
| A2 | 150 | Green |
| A3 | 175 | Yellow |

TABLE 2

MEDIUM

| Block ID | Pixel Count | Color |
|---|---|---|
| B1 | 125 | Red |
| B2 | 175 | Green |
| B3 | 195 | Yellow |

TABLE 3

HARD

| Block ID | Pixel Count | Color |
|---|---|---|
| C1 | 130 | Red |
| C2 | 180 | Green |
| C3 | 200 | Yellow |

At step 1316, the processor chooses the next target block. In a preferred embodiment, the next target block is different from the previous target block.

At step 1318, the processor displays instructions to the patient. In a preferred embodiment, the instructions include instructions to insert the set of blocks corresponding to the block table into the entry portal of the device.

At step 1320, the processor analyzes the camera image. At step 1322, the processor decides whether or not blocks are present in the camera image. If not, the process returns to step 1318. If so, the processor proceeds to step 1324. At step 1324, the processor analyzes whether or not the blocks present in the camera display are the same blocks as those in the corresponding block table. In a preferred embodiment, the processor analyzes both the color and the pixel count for each block and compares each one to the color and pixel count in the corresponding block table. In this step, each block must match the color and the pixel count for the table, with no extraneous blocks and no missing blocks for the method to return "true." If the correct blocks are not present, the method returns to step 1312. If the correct blocks are present, the method moves to step 1326.

At step 1326, the processor analyzes the pixel count in the blue start bar present in the image. If the pixel count is equal to the total predetermined pixel count for the blue start bar, then the processor assumes that the patient has not inserted his hand into the hand portal, and returns to step 1318. If the pixel count is not equal to the total predetermined pixel count for the blue start bar, then the processor assumes that the patient has inserted his hand into the hand portal and proceeds to step 1328.

Referring then to FIG. 13B, at step 1328, the processor starts the timer. At step 1329, the processor sends a signal to the impact, to start VNS. At step 1330, the processor again observes the blue pixel count image from the start bar in the camera image. If the blue pixel count is the same, then the processor assumes that the patient's hand is still in the hand portal and proceeds to step 1332. At step 1332, if a time limit has not expired then the processor returns to step 1330. If the time limit has expired, then the processor proceeds to step 1334. At step 1334, timeout display message is sent from the processor to the display. At step 1336, the processor returns to step 1302.

At step 1330, if the blue pixel count is equal to the total, then the processor assumes that the patient's hand has been withdrawn from the hand portal and moves to step 1337. At step 1337, the processor sends a signal to the implant to stop VNS. At step 1338, the processor stops the timer. At step 1340, the processor retrieves the image from the camera. At step 1342, the processor decides whether or not the correct block is missing from the camera image. If the correct block is missing from the camera image, then the processor moves to step 1344. At step 1344, the processor records the time lapsed. At step 1346, the processor records the block that is missing. At step 1348, the processor displays a message to the patient. At this step, in a preferred embodiment, the processor may display a reward "image" or otherwise reward the patient for correct block choice. At step 1350, the processor receives an input from the patient as to whether or not to continue. If not, the processor moves to step 1352. If so, the processor moves to step 1354 and returns to step 1302.

If at step 1342 the correct block is not missing from the image, the processor moves to step 1356. At step 1356, the processor records the elapsed time. At step 1358, the processor records the block is missing from the image. At step 1360, the processor displays a negative message to the patient and may apply negative feedback. At step 1362, the processor displays an image on the display requesting a decision from the patient as to whether or not to continue. If so, the processor moves to step 1364 and returns to step 1302. If not, the processor moves to step 1352. At step 1352, the processor analyzes the current statistics present in memory, as will be further described.

At step 1366, the processor provides a report to the patient, and to the server.

At step 1368, the process ends.

Figure 13C:
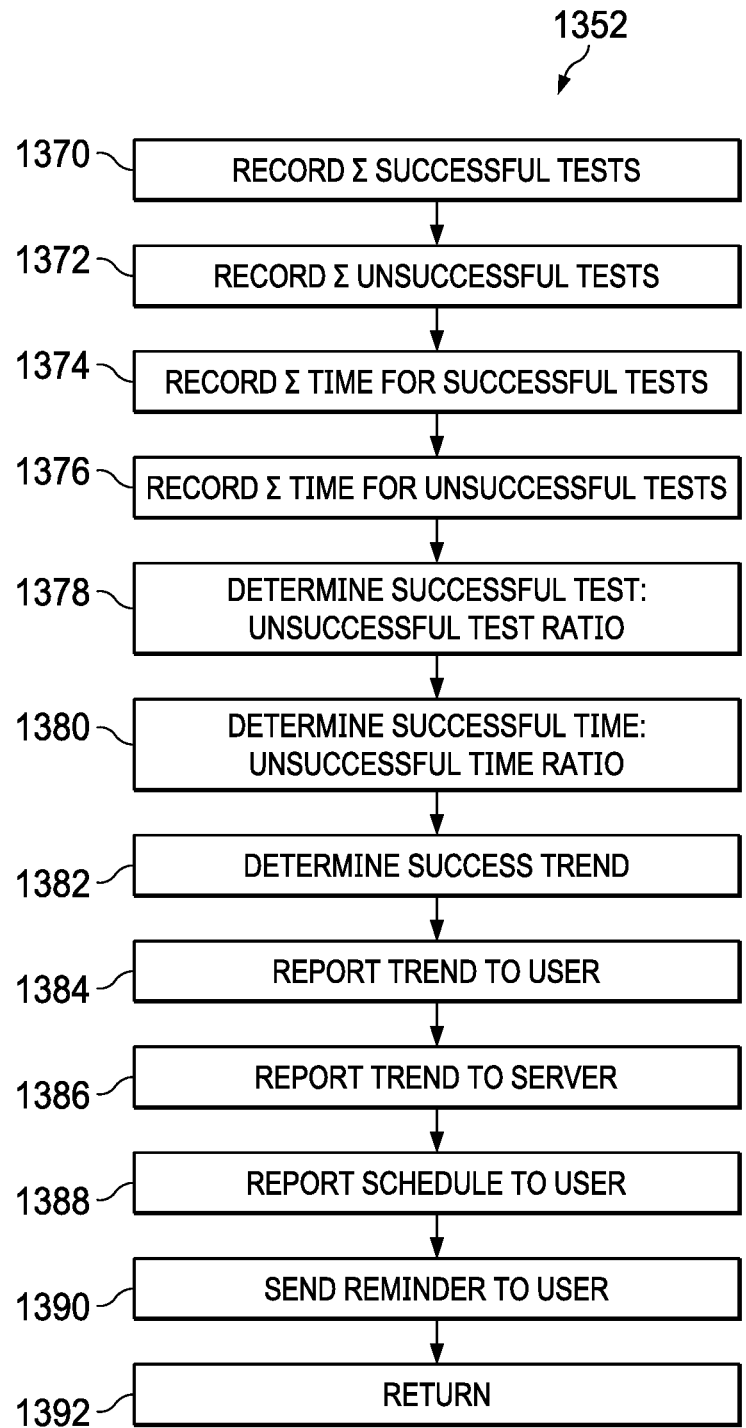
FIG. 13C is a block diagram of a method for analyzing statistics present in accordance with an illustrative embodiment of the invention.

Referring then to FIG. 13C, step 1352 will be further described.

At step 1370, the processor records a summation of the number of successful test results.

At step 1372, the processor records a running summation of the number of unsuccessful tests.

At step 1374, the processor records a running summation of the time for successful tests.

At step 1376, the processor records a running summation for the time for unsuccessful tests.

At step 1378, the processor determines a ratio of the number of successful tests to the number of unsuccessful tests.

At step 1380, the processor determines a ratio of the running total of successful time to the running total of unsuccessful time.

At step 1382, the processor determines a trend in the number of success. In a preferred embodiment, a "positive" or "negative" trend is reported. An "positive" trend is determined if the average daily number of successful is greater than the running summation of the number of successful tests. A "negative" trend is determined when the number of daily successful tests is below the running average of successful tests.

At step 1384, the successful tests and the successful test ratio, the successful time to the unsuccessful time ratio, and the success trend is reported to the user.

At step 1386, all calculated statistics noted above are reported to the server.

At step 1388, the processor reports a predetermined schedule of preferred times for rehabilitation therapy and lengths of rehabilitation are reported to the user.

At step 1390, the processor sends a text message or email to the user as a reminder to conduct therapy according to the schedule.

At step 1392, the processor returns.

EXAMPLES

Specific exemplary embodiments will now be further described by the following, nonlimiting examples which will serve to illustrate in some detail various features of the invention. The following examples are included to facilitate an understanding of ways in which embodiments of the present disclosure may be practiced. However, it should be appreciated that many changes can be made in the exemplary embodiments which are disclosed while still obtaining like or similar result without departing from the scope of embodiments of the present disclosure. Accordingly, the examples should not be construed as limiting the scope of the present disclosure.

Example 1

This example is based on experimental results from laboratory rats that show reversal of pathological plasticity restores sensory function after nerve injury. The results also show reversal of pathological plasticity is necessary to restore sensory function after nerve injury.

CL-VNS provides precisely-timed release of neuromodulators, including acetylcholine, during rehabilitation. Rats underwent complete transection and repair of the median and ulnar nerves in the right forelimb. After six weeks to allow reinnervation to occur, short bursts of vagus nerve stimulation were delivered coincident with forelimb rehabilitative training (CL-VNS). Two control groups that either decoupled VNS from rehabilitation or depleted acetylcholine in the brain were included to control for VNS effects independent of central plasticity, including potential effects on reinnervation. The examples described below show that CL-VNS reversed the maladaptive central reorganization resulting from nerve damage without influencing peripheral nerve or muscle health, and subsequently enhanced recovery of motor and sensory function. These data demonstrate a causal role for central plasticity in dysfunction after nerve injury and introduces CL-VNS paired with motor and/or tactile rehabilitation as a unique therapy having unexpectedly advantageous results.

Referring to FIG. 14A, sensory threshold in grams is plotted on the vertical axis. The horizontal axis of FIG. 14A is a separation of different groups of rats as follows. Group 1405 shows left paw results from an experimental group that received rehabilitation. Group 1410 shows left paw results from an experimental group that received VNS and rehabilitation. Group 1415 shows left paw results from an experimental group that received delayed VNS. Group 1420 shows left paw results for an uninjured control group. Group 1425 shows right paw results from an experimental group that received rehabilitation. Group 1430 shows right paw results from an experimental group that received VNS and rehabilitation. Group 1435 shows right paw results from an experimental group that received delayed VNS. Group 1440 shows right paw results for the uninjured control group.

Referring to FIG. 14B, right forelimb use in percent is plotted on the vertical axis. The horizontal axis of FIG. 14B is a separation of different groups of rats as follows. Group 1450 shows right paw forelimb use percent results from an experimental group that received rehabilitation. Group 1460 shows right paw forelimb use percent results from an experimental group that received VNS and rehabilitation. Group 1470 shows right paw forelimb use percent results from an experimental group that received delayed VNS. Group 1480 shows right paw forelimb use percent results for an uninjured control group.

FIG. 14A shows that sensory thresholds in the injured paw were significantly increased, consistent with a loss of sensation following nerve injury (Two-Way ANOVA, main effect of paw, $F[1,41]=79.93$, $p=1.13\times10^{-10}$). VNS+Rehab significantly improved tactile sensation in the denervated forepaw (right) compared to both Rehab and Delayed VNS ($F[2,20]=6.35$, $p=0.008$). This reduction in sensory threshold in the injured right paw toward uninjured is an advantageous unexpected result. No change was observed in the uninjured forepaw (left) ($F[2,20]=2.22$, $p=0.14$). FIG. 14B shows that VNS+Rehab improved spontaneous forelimb use during exploration on the cylinder task compared to both Rehab and Delayed VNS. This increase in injured paw use toward uninjured is an advantageous unexpected result.

Referring to FIG. 15A, sensory threshold in grams is plotted on the vertical axis. The horizontal axis of FIG. 15A is a separation of different groups of rats as follows. Group 1505 shows left paw results from an experimental group that received rehabilitation. Group 1510 shows left paw results from an experimental group that received VNS and rehabilitation. Group 1515 shows left paw results from an experimental group with depletion of acetylcholine that received VNS and rehabilitation. Group 1520 shows left paw results for an uninjured control group. Group 1525 shows right paw results from an experimental group that received rehabilitation. Group 1530 shows right paw results from an experimental group that received VNS and rehabilitation. Group 1535 shows right paw results from an experimental group with depletion of acetylcholine that received VNS and rehabilitation. Group 1540 shows right paw results for the uninjured control group.

Referring to FIG. 15B, right forelimb use in percent is plotted on the vertical axis. The horizontal axis of FIG. 15B is a separation of different groups of rats as follows. Group 1550 shows right paw forelimb use percent results from an experimental group that received rehabilitation. Group 1560 shows right paw forelimb use percent results from an experimental group that received VNS and rehabilitation. Group 1570 shows right paw forelimb use percent results from an experimental group with depletion of acetylcholine that received VNS and rehabilitation. Group 1580 shows right paw forelimb use percent results for an uninjured control group.

FIG. 15A shows that sensory thresholds in the injured paw were significantly increased, consistent with a loss of sensation following nerve injury (Two-Way ANOVA, main effect of paw, $F[1,29]=51.7$, $p=1.97\times10^{-7}$). VNS+Rehab significantly improved tactile sensation in the denervated forepaw (right) compared to both Rehab and ACh-:VNS+Rehab ($F[2,14]=7.54$, $p=0.008$). This reduction in sensory threshold in the injured right paw toward uninjured is an advantageous unexpected result. No change was observed in the uninjured forepaw (left) ($F[2,14]=0.31$, $p=0.74$). FIG. 15B shows that VNS+Rehab improved spontaneous forelimb use during exploration on the cylinder task compared to both Rehab and ACh-:VNS+Rehab (depletion of acetylcholine in rats that receive equivalent VNS paired with rehabilitation). The acetylcholine depleted prevention of VNS-dependent reversal of pathological plasticity in ACh-:VNS+Rehab and the increase in VNS+Rehab injured paw use almost back to uninjured are both advantageous unexpected results.

Example 2

This second example is based on experimental results from human patients. To quantify stereognosis scoring using the various stereognosis object sets, discrimination of different stereognosis object sets are benchmarked versus standard assessments such as Fugl-Meyer upper extremity scale (UEFM), Action Research Arm Test (ARAT), Wolf Motor Function Test (WMFT), Stroke Impact Scale (SIS), Box and Block test, 9-hole peg test, grip and pinch force, two-point discrimination, tactile threshold, and proprioception.

Figure 16A:
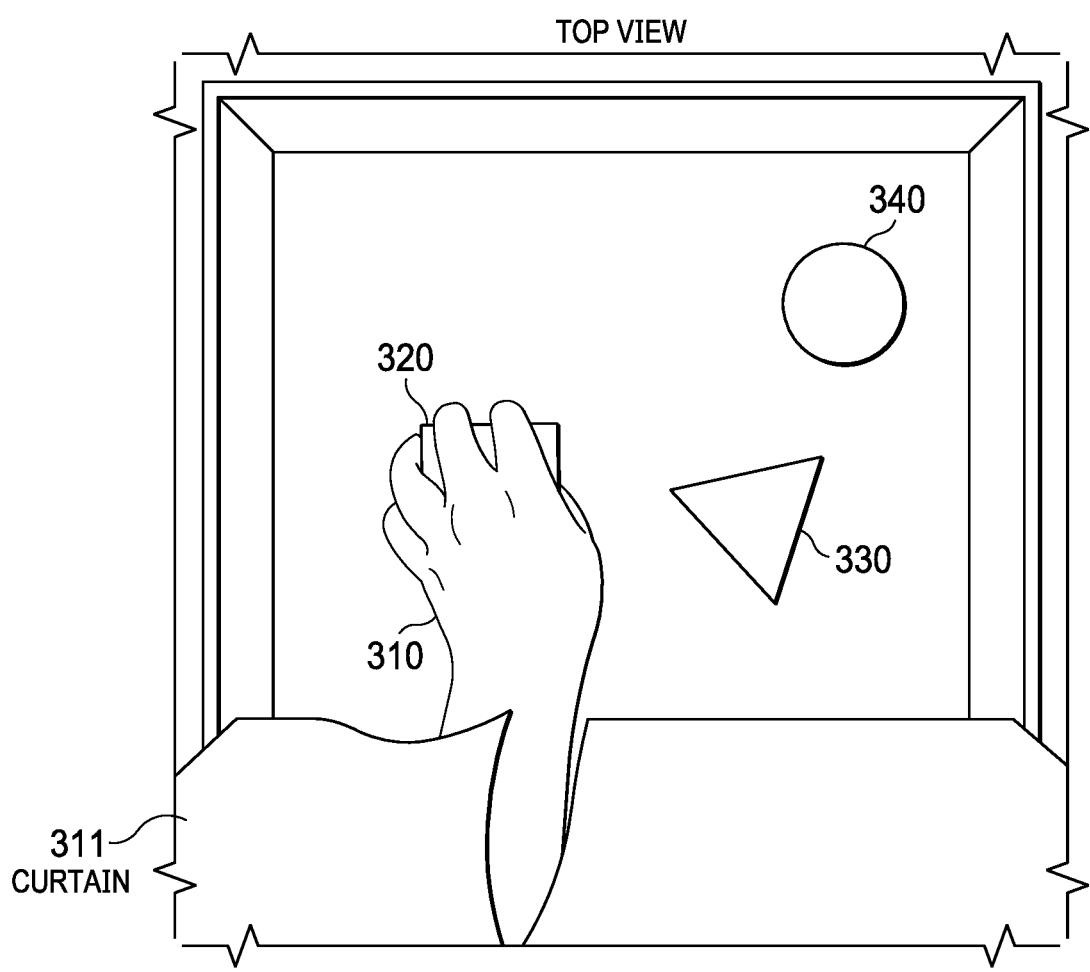
FIG. 16A is a top view of a stereognosis training system in use according to an illustrative embodiment of the invention.
Figure 16B:
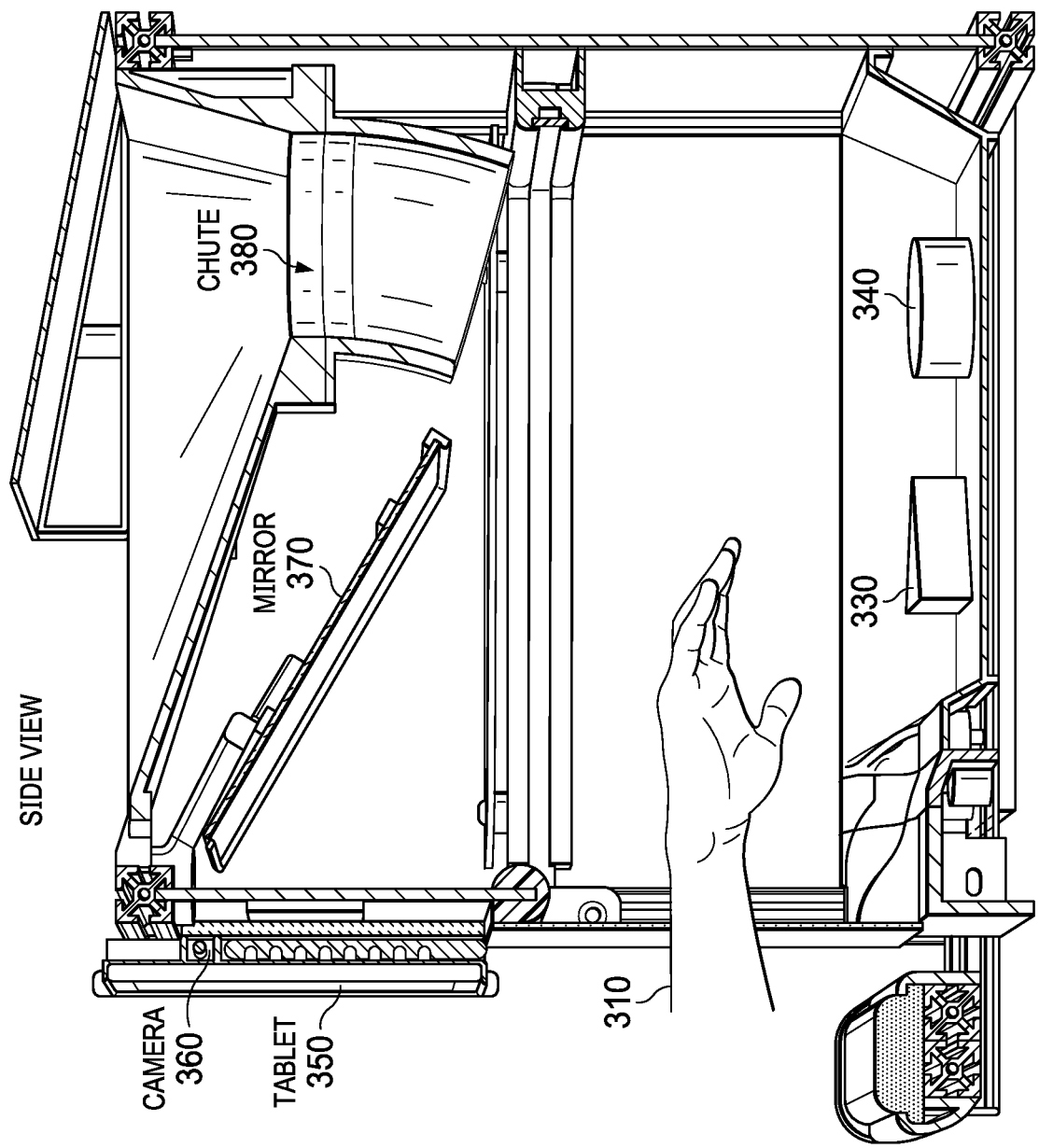
FIG. 16B is a side view of a stereognosis training system according to an illustrative embodiment of the invention.

Referring then to FIGS. 16A and 16B, the experimental setup will be described. FIG. 16A is a top view from the camera of an experiment in process. As can be seen, patient's hand 310 is reaching through curtain 311 and toward objects 320, 330 and 340. The objects in this object set correspond to object set 819. Similarly, FIG. 16B shows a cutaway side view of the apparatus used for this experiment. Patient's hand 310 can be seen reaching toward objects 330 and 340. Tablet computer 350 including camera 360 observes patient's hand in movement via mirror 370, as shown in FIG. 16A. Once the experiment task was completed the target block removed was placed back in chute 380 where it was returned to the floor of the device.

Referring to FIG. 16C, benchmarking relationship 1600 between a standard stroke score and a stereognosis score for a group of patients is shown.

To quantify stereognosis scoring using the various stereognosis object sets, discrimination of different stereognosis object sets were benchmarked versus standard assessments such as Fugl-Meyer upper extremity scale (UEFM), Action Research Arm Test (ARAT), Wolf Motor Function Test (WMFT), Stroke Impact Scale (SIS), Box and Block test, 9-hole peg test, grip and pinch force, two-point discrimination, tactile threshold, and proprioception. An example of a benchmarking relationship between a standard stroke score and a stereognosis score for a stereognosis object set (or multiple sets) is shown in FIG. 16C. In an embodiment of the present invention, the interactive device of the stereognosis system is programmed to evaluate the stereognosis score of a patient assessment and apply the benchmarking relationship.

X-axis 1602 represents standard stroke "score" for a patient. The standard stroke score is provided in "points" and reflects an integer sum of several subscores based on a clinical evaluation. For example, zero points is awarded for no performance (such as inability to complete test). 1 point is awarded for poor performance, 2 points are awarded for normal or slightly below average performance, 3 points is awarded for above average performance. 4 points is awarded for good performance. The y-axis 1604 represents stereognosis score for the same patient. The stereognosis score is provided in number of objects successfully retrieved in a predetermined 1 minute time interval. Each of the data points 1606, 1608, 1610, 1612, 1614, 1616, 1618, 1620,

1622, 1624, 1626 and 1628 represent two tests for the same patient and the resulting standard stroke score and stereognosis therapy score.

Diagonal line 1630 indicates the mean average of all tests as can be seen, the diagonal line shows that for each individual patient, the standard stroke scores generally correlates positively to the stereognosis scores.

Figure 17:
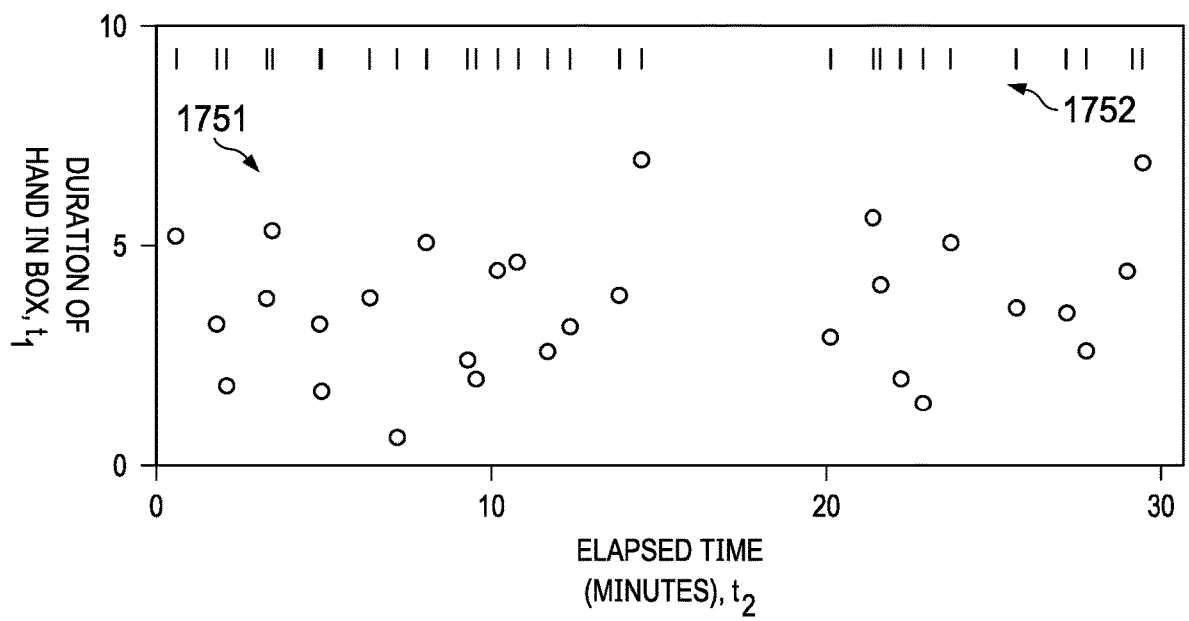
FIG. 17 is a graph plotting duration of time hand in box versus elapsed time in accordance with an illustrative embodiment of the invention.

FIG. 17 is a time series plot 1750 of the duration that a patient's hand is inside the box engaging the set of objects to perform a task versus the elapsed time for the task to be completed. Time series plot 1750 shows patient engagement times 1751 (shown as dots) with the stereognosis system. Analysis of time series plot 1750 further indicates appropriate timing for external stimulation. Time marks 1752 show appropriate intervals for external stimulation (time that stimulation is started and duration of stimulation in time). For example, at time marks 1752, vagus nerve stimulation is applied to a patient, at a specific time and for a duration of time, based on the patient's current engagement time with the blocks (measured by the duration of a hand being in the box). In this example, the duration of the stimulation is about 3 seconds. The stimulation can be seen to be delivered approximately simultaneously to the conclusion of the task.

Figure 18:
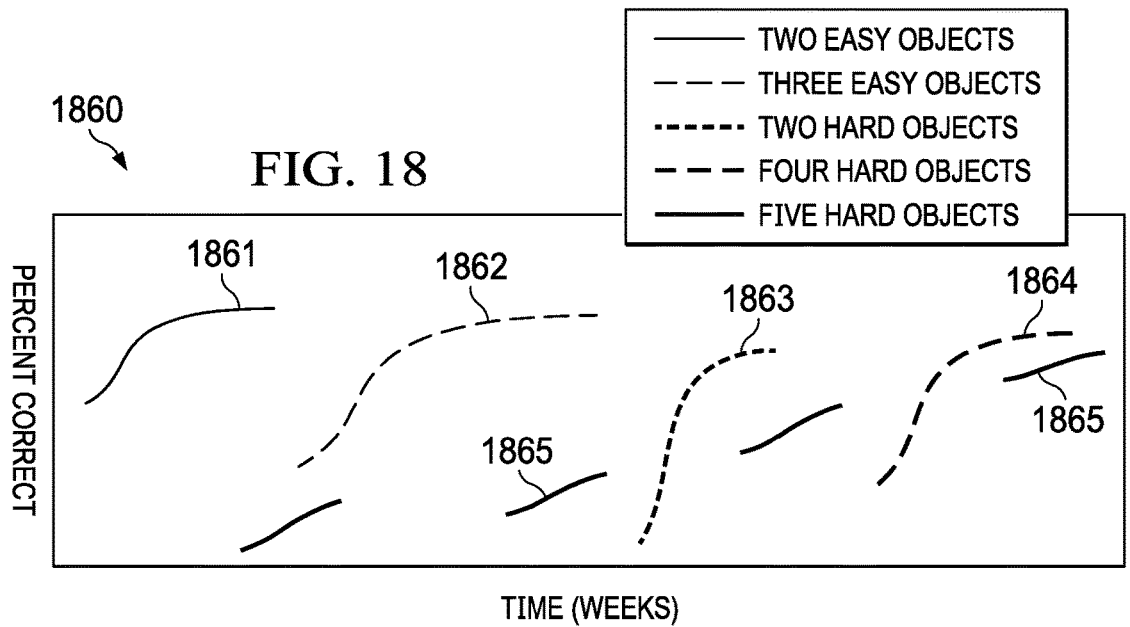
FIG. 18 is a graph of performance history for various object sets in accordance with an illustrative embodiment of the invention.

Referring to FIG. 18, a plot 1860 of use history and tactile sensory improvement over time, is shown. Sets of objects and performance history plots are color coded to match task difficulty and tactile sensory function. For example, a patient is first given a task of a set of purple objects and the percentage of correct attempts is recorded and shown as graph 1861. When reaching a plateau percentage, the patient is given a task for a set of green objects which are slightly more difficult for tactile recognition. The patient's progress is recorded as a percentage of correct attempts and plotted in graph 1862. When mastering the green object tasks, the training program continues with the patient given tasks for yellow objects and thereafter a task blue objects based on mastery of the task for yellow objects. The results are shown in graph 1863 and graph 1864, respectively. Simultaneous to the purple, green, yellow and blue tasks, the training program begins to introduce tasks for red objects having a difficult level of tactile recognition. The patient's progress with the red object tasks are tracked and plotted as graph 1865. While gathering the tactile sensory results in graph 1861, graph 1862, graph 1863, graph 1864 and graph 1865 the interactive device can make suggestions and confirm the number and category of objects used. The early and sustained improvement in the percent correct for the much more difficult object set of 5 hard objects shown in the segments of graph 1865 is an advantageous unexpected result for tactile training paired with CL VNS. The interactive device can be configured to suggest changes to the object set to make the task easier or more difficult as needed. Furthermore, the interactive device can adjust the level of vagus nerve stimulation and trigger the stimulation based on task performance in the use history.

Example 3

This third example is based on experimental results from human patients. FIGS. 19A, 19C, 19E and 19G show performance as measured by success rate on sets of all difficulties from each object type. The object sets can be seen to correspond to these of FIG. 8A. Success rate is an aggregated version of the search time indicating the number of successful retrievals per minute of search time. This can be termed object selection rate. It can be used to describe performance in a single session or performance overall. In each figure blue (the taller bar graph of each of the three pairs in a given figure) indicates control subjects (n=4), and red (the shorter bar graph of each of the 3 pairs in a given figure) indicates impaired subjects (n=9).

Figure 19A:
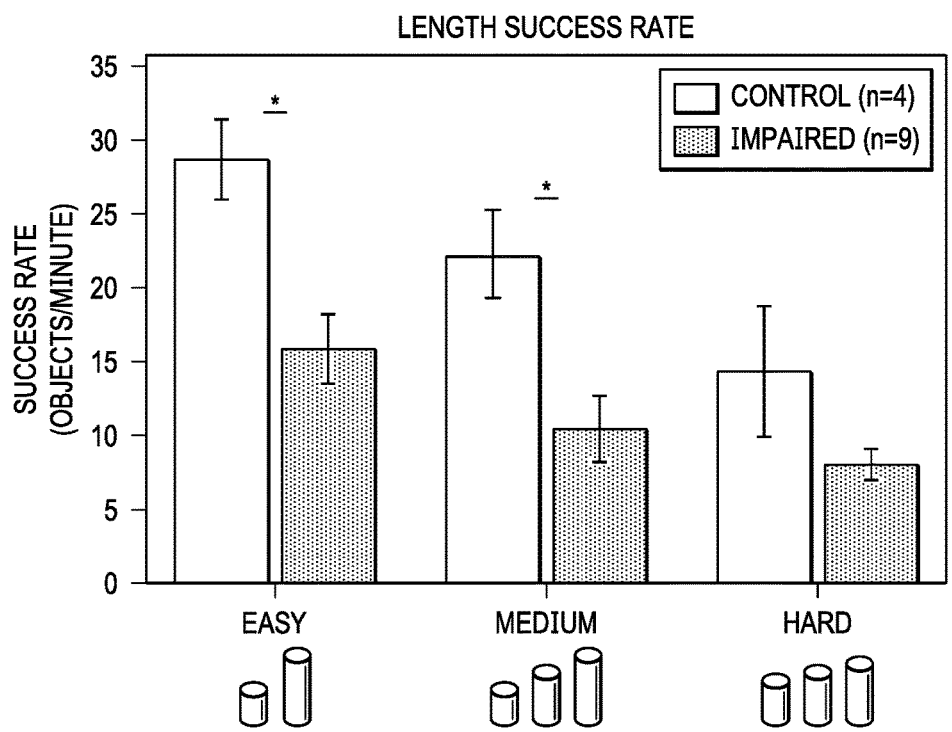
FIGS. 19A-19H are graphs depicting success rate and correct percentage based on task difficulty in accordance with an illustrative embodiment of the invention.
Figure 19B:
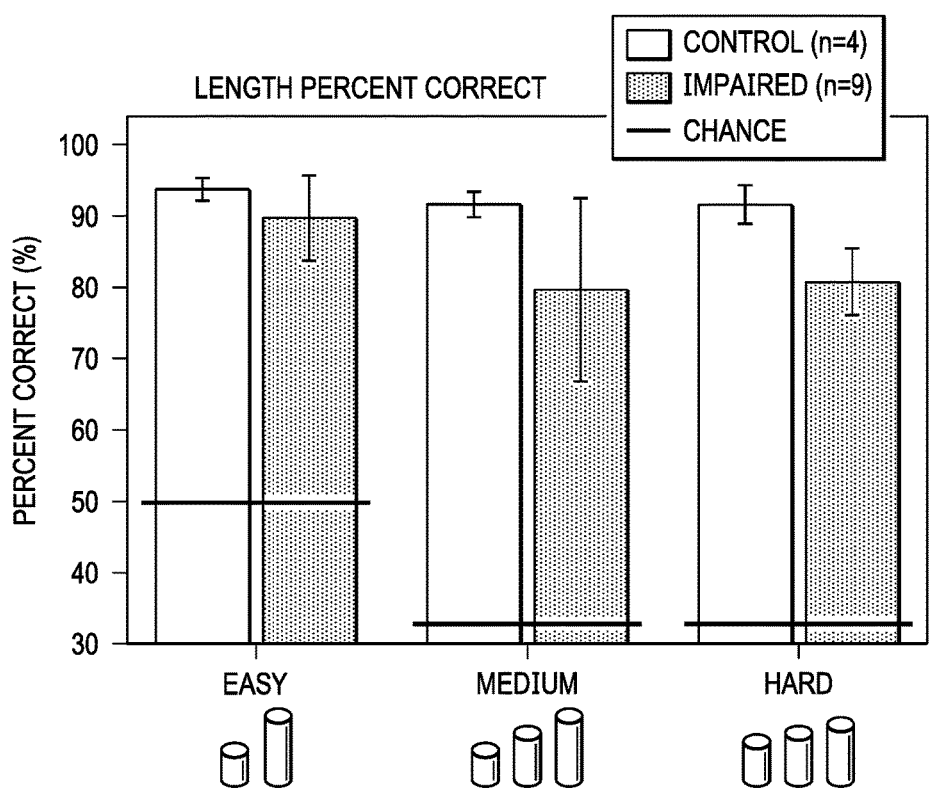
Figure 19C:
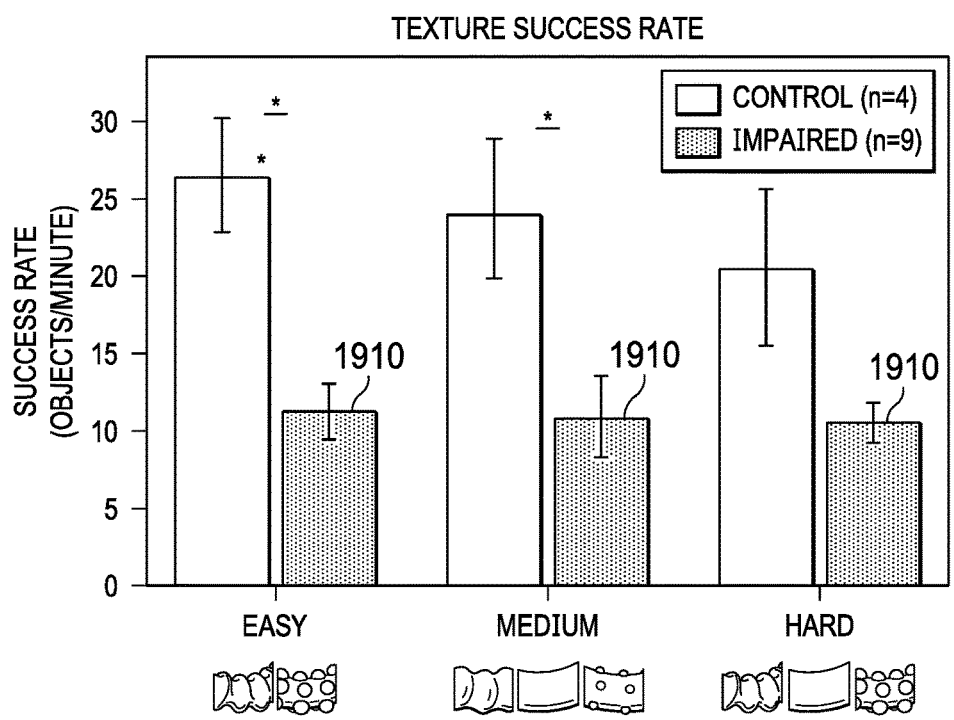

Of note, FIG. 19C shows that success rate (object selection rate) for texture for the impaired group 1910 did not go down with the progression from easy to medium to hard as it did with the other 3 object types. This is an advantageous unexpected result because it shows that the texture type object sets remained equivalently challenging (plasticity eliciting) for the impaired participants even while the participants accumulated more experience with the task.

FIGS. 19B, 19D, 19F and 19H show performance as measured by percent correct on sets of all difficulties from each object type. Percent correct is defined as the percent of retrievals that found the correct object and can be averaged over all sessions to describe a participant's overall performance. The grey lines indicate the chance performance for percent correct.

Figure 19D:
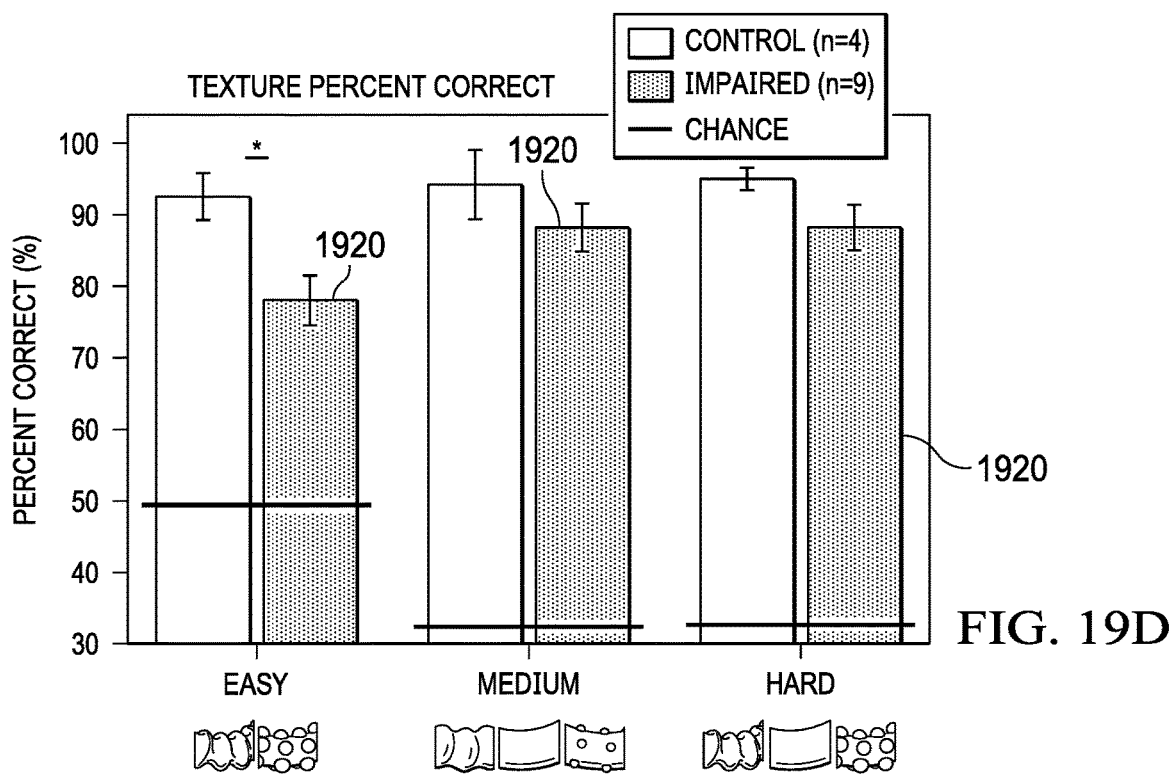
Figure 19E:
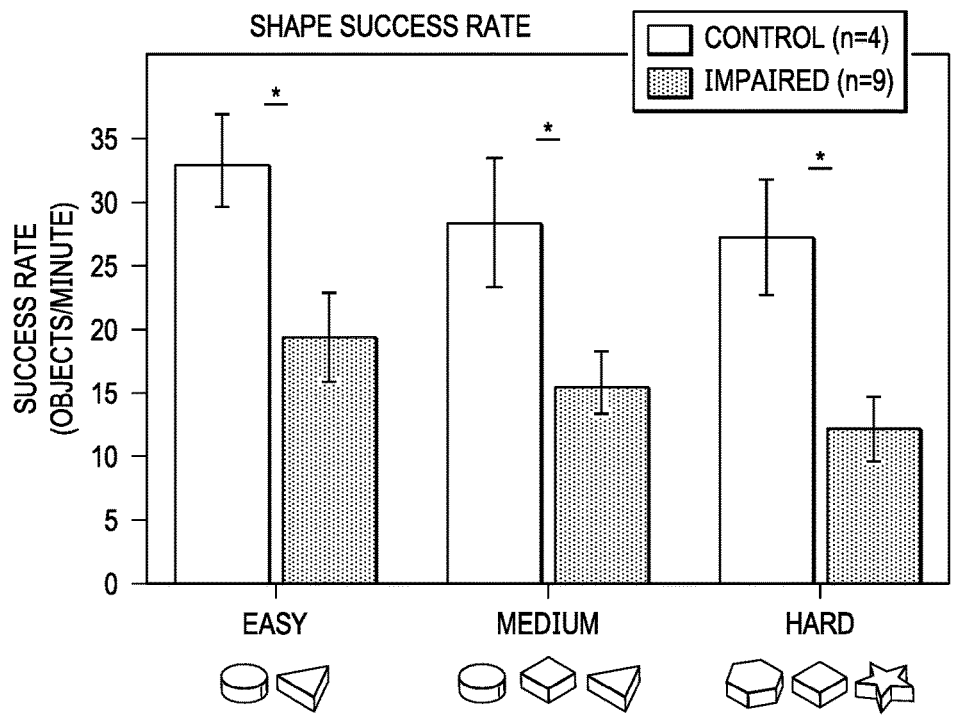
Figure 19F:
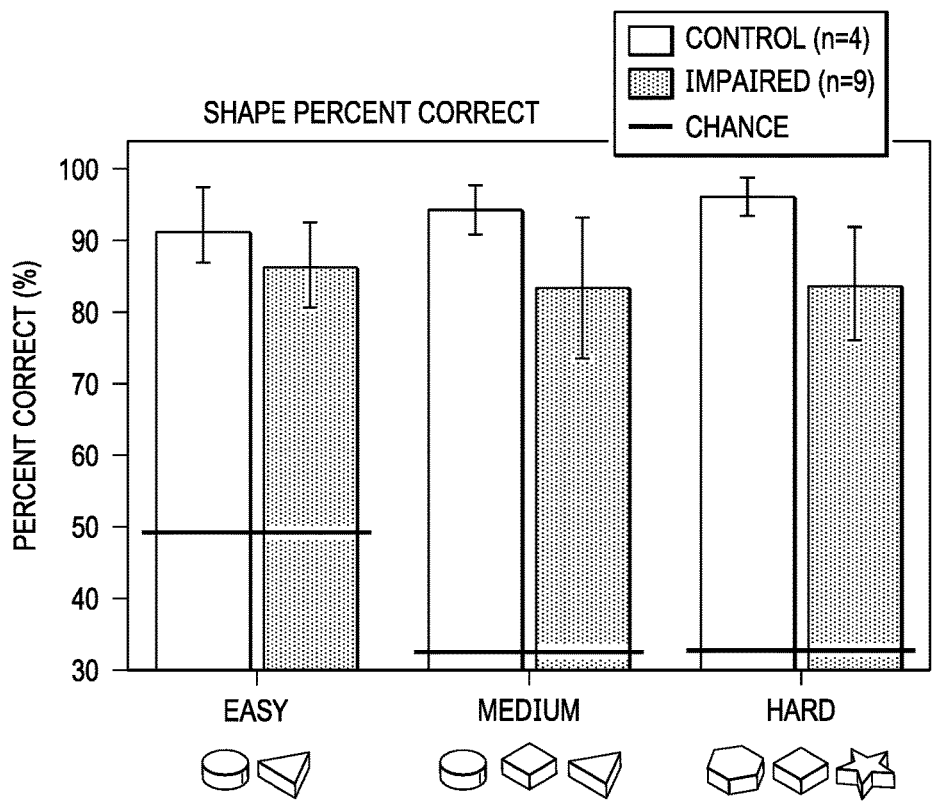
Figure 19G:
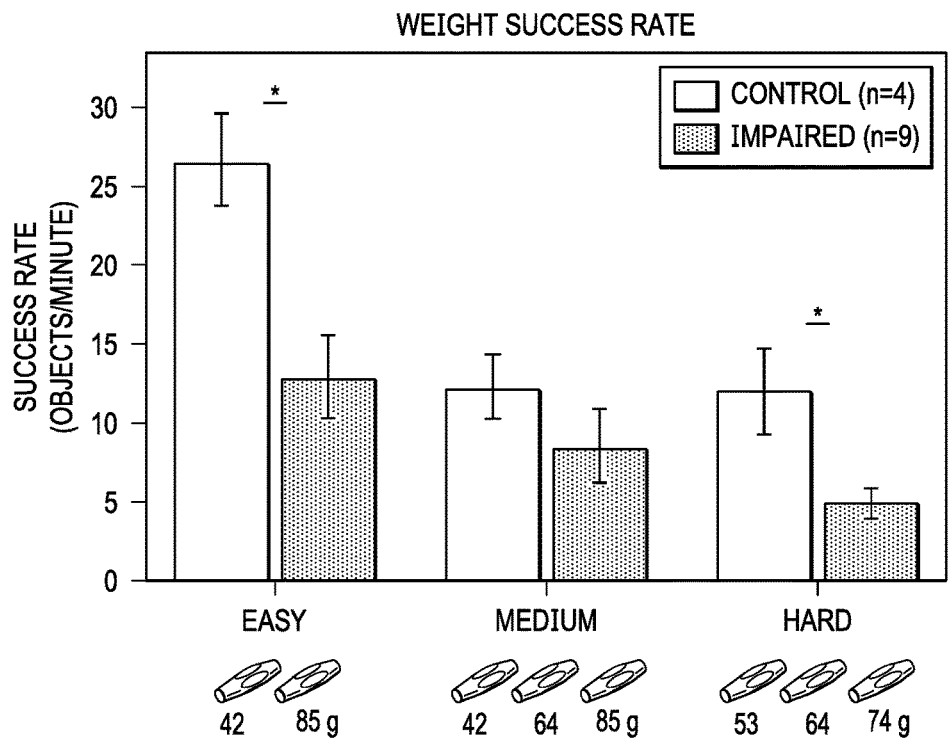
Figure 19H:
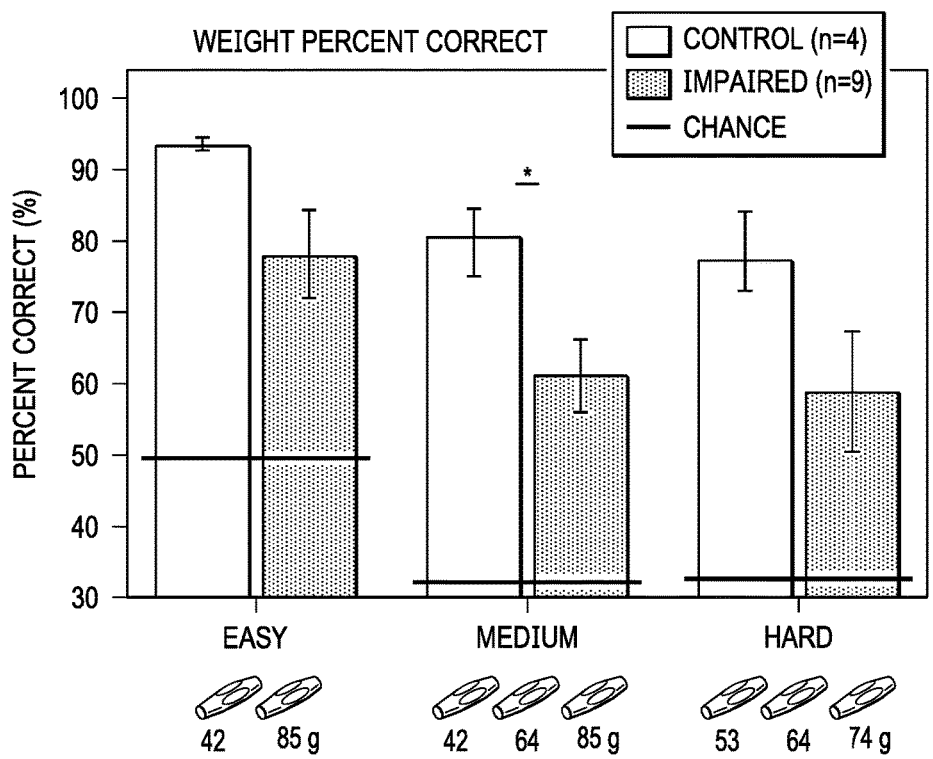

Also of note, FIG. 19D shows that percent correct for texture for the impaired group 1920 went up with the progression from easy to medium to hard in contrast to the decline or steady state with the other 3 object types. This is an advantageous unexpected result because it shows that the impaired participants continued to improve with texture type object sets in absolute terms even while the object sets became more difficult (overcoming maladaptive central plasticity). In view of the results shown in FIGS. 19C-19D, it may be an advantageous rehabilitation strategy for impaired participants to devote relatively more training time to texture object sets compared to the other types of object sets.

Figure 20:
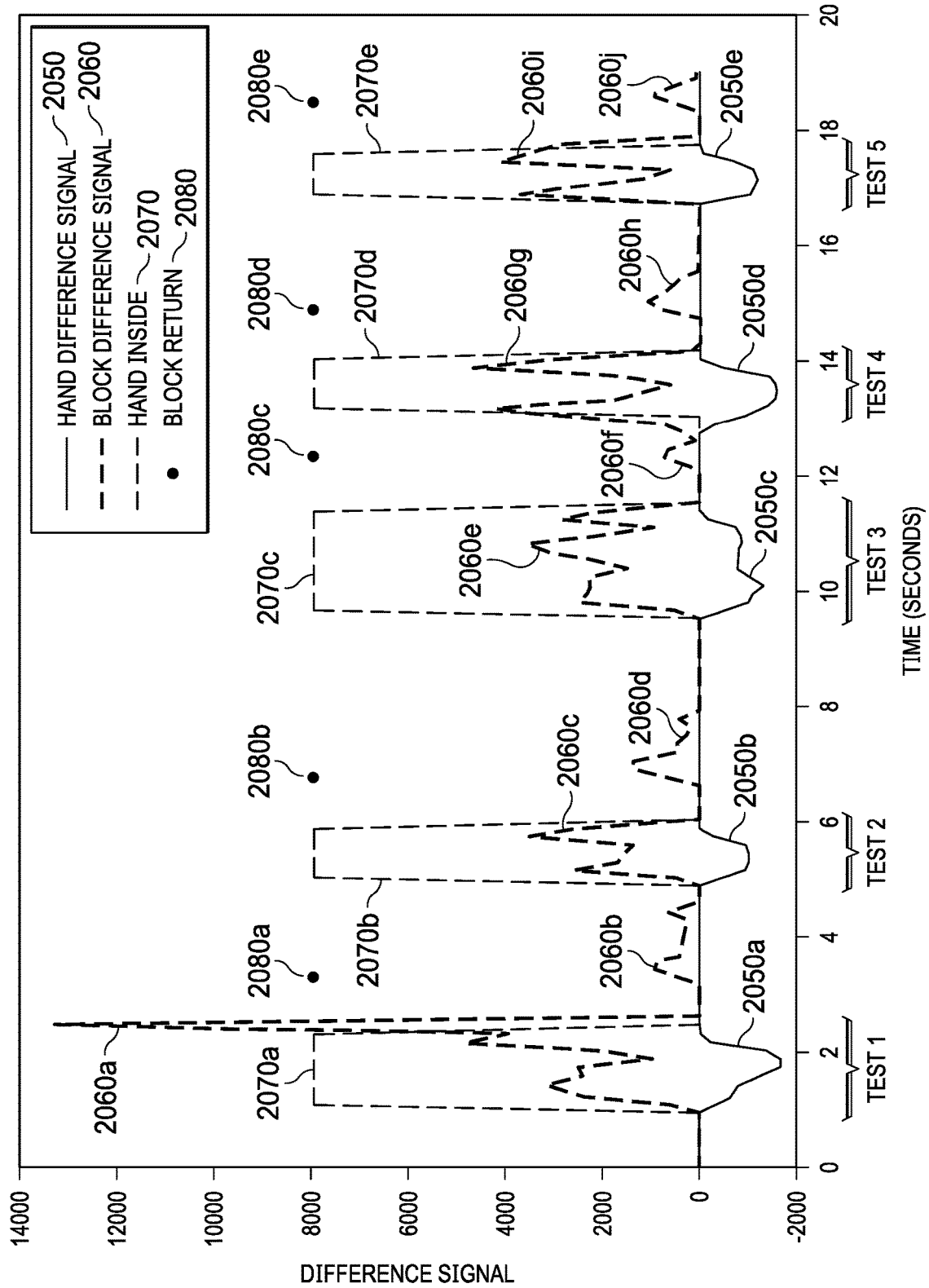
FIG. 20 is a graph comparing different signals returned from a camera over time in accordance with an illustrative embodiment of the invention.

Referring then to FIG. 20, a comparison of difference signals returned from the camera versus time, for five independent test are shown. The difference signal is related to the number of pixels received by the camera for various colors. Hand difference signal 2050 indicates the total pixel count for the blue line adjacent the hand opening. Block different signal 2060 indicates the cumulative pixel count for all blocks of all colors observed by the camera over time, on the floor of the container. Hand inside signal 2070 indicates the period of time that the patient's hand was inside the box. Block return indicator 2080 indicates the time when the blocks were reintroduced into the chute, as recorded by onboard sensors connected to the processor.

Referring then to Test 1, it can be seen that the pixel count for the block differential signal 2060a increased from 0 to approximately 13,500 over the space of approximately 2.25 seconds. The block differential signal then returns to 0. Correspondingly, hand differential signal 2050a shows a decrease in blue pixels by nearly 2,000 pixels indicating that the patient's arm is extended over at least a portion of the blue bar. Hand inside signal 2070a indicates that the patient's arm was inside the box for approximately 1.2 seconds. Block return indicator 2080a indicates that the blocks were returned to the chute after approximately 3 seconds. Block differential signal 2060b indicates that the blocks were returned to the floor of the box in about 3 seconds and 4.25 seconds.

Referring to Test 2, block differential signal 2060c indicates a rise in pixel count from 0 to about 3,000 and then returning back to 0 over the period of about 5 seconds to about 6 seconds. Correspondingly, hand differential signal 2050b indicates the patient's arm was extended over the blue bar from about 5 seconds to about 6 seconds. Hand inside signal 2070b indicates that the patient's hand was inside the box from about 5 seconds to about 6 seconds. Block return indicator 2080b indicates that the blocks were returned to the chute at about 6.25 seconds. Block differential signal 2060d indicates that the blocks returned to the floor of the box between about 6.5 seconds and 8 seconds.

Referring to Test 3, block differential signal 2060e indicates that the blocks were present and moved on the floor of the box from about 9.5 seconds to about 11.5 seconds. Correspondingly, hand differential signal 2050c indicates that the pixel count for the blue bar decreased between about 9.5 seconds and about 11 seconds. Hand inside signal 2070c indicates that the patient's hand was inside the box from about 9.5 seconds to about 11.5 seconds for a total of about 2 seconds. Block return indicator 2080c indicates that the blocks were returned to the chute at approximately 12 seconds. Block differential signal 2060f indicates that the blocks were returned to the floor of the device between about 12 seconds and about 12.75 seconds.

Referring to Test 4, block differential signal 2060g indicates that the blocks were present and moved on the floor of the box from about 12.5 seconds to about 14 seconds. Correspondingly, hand differential signal 2050d indicates that the blue bar was reduced in pixel count from about 12.5 seconds to about 14 seconds. Hand inside signal 2070d indicates that the hand was inside the box from about 13 seconds to about 14 seconds. Block return indicator 2080d indicates that the blocks were returned to the chute at about 14.5 seconds. Block differential signal 2060h indicates that the blocks were present on the floor of the device between about 14.8 seconds and 15.5 seconds.

Referring to Test 5, block differential signal 2060i indicates that the blocks were present and moved on the floor of the device between about 16.8 seconds and 18 seconds. Correspondingly, hand differential signal 2050e indicates that the blue pixel count of the blue bar was reduced between about 16.8 seconds and about 17.8 seconds. Hand indicator signal 2070e indicates that the hand was inside the box from about 16.8 seconds to about 17.8 seconds. Block return indicator 2080e indicates that the blocks were returned through the chute at about 18.5 seconds. Block differential signal 2060j indicates that the blocks were present on the floor of the device between about 18 seconds and 19 seconds.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

The invention claimed is:

1. A stereognosis training system comprising:
a container, including an interior chamber;
a portal, ductedly connected to the interior chamber;
a set of objects, movably disposed in the interior chamber;
an obstruction, for obscuring a view of the set of objects;
a camera, in view of the set of objects;
a processor, having a memory, operatively connected to the camera;
the memory including a set of program instructions that, when executed by the processor, cause the system to perform the steps of:
monitoring the portal for an ingress into the portal and an egress from the portal; and,
identifying an elapsed time between the ingress and the egress.

2. The system of claim 1 wherein the container further comprises:
a frame;
a front wall, a set of sidewalls, a rear wall, and a floor, removably attached to the frame; and,
an entry structure, supported by the frame, ductedly connected to the interior chamber.

3. The system of claim 1, further comprising:
a display, supported by the frame, operatively connected to the processor; and,
wherein the set of program instructions further include instructions that when executed cause the system to:
display at least one object, of the set of objects, on the display.

4. The system of claim 1, further comprising:
a downward facing mirror, adjacent the camera, directed toward the interior chamber.

5. The system of claim 1, wherein the obstruction is adjacent the portal and the interior chamber.

6. The system of claim 1, wherein the set of objects further comprises objects for stimulating at least one of the group of:
mechanoreceptors;
nociceptors; and,
thermoreceptors.

7. The system of claim 1, wherein the set of objects includes at least one of the group of:
a first subset related to Ruffini endings;
a second subset related to Meissner corpuscles;
a third subset related to Merkel's disks;
a fourth subset related to proprioceptors;
a fifth subset related to thermoreceptors; and,
a sixth subset related Pacinian corpuscles.

8. The system of claim 7, wherein:
the first subset is comprised of a first color set;
the second subset is comprised of a second color set;
the third subset is comprised of a third color set;
the fourth subset is comprised of a fourth color set;
a fifth subset is comprised of a fifth color set; and,
a sixth subset is comprised of a sixth color set.

9. The system of claim 7, wherein:
the first subset varies in length;
the second subset varies in texture;
the third subset varies in shape;
the fourth subset varies in weight;
the fifth subset varies in temperature; and,
the sixth subset varies in vibration.

10. The system of claim 9, further comprising:
a trigger bar adjacent the portal and the interior chamber, comprised of a seventh color set;
the camera in view of the trigger bar; and,
the set of instructions further cause the system to perform the steps of:
registering the ingress when a differential signal related to the seventh color set decreases; and,
registering the egress when the differential signal related to the seventh color set increases.

11. The system of claim 8, wherein the set of instructions further cause the system to perform the at least one of the steps from the group of:
identifying each object of the first subset by a first set of differential signals related to the first color set;

identifying each object of the second subset by a second set of differential signals related to the second color set;
identifying each object of the third subset by a third set of differential signals related to the third color set;
identifying each object of the fourth subset by a fourth set of differential signals related to the fourth color set;
identifying each object of the fourth subset by a fifth set of differential signals related to the fifth color set; and,
identifying each object of the fourth subset by a sixth set of differential signals related to the sixth color set.

12. The system of claim 1, further comprising:
a network interface, connected to the processor;
a network, in communication with the network interface;
a user device, connected to the network; and,
wherein the set of instructions further cause the system to perform the step of:
  sending a signal, based on the elapsed time, to the user device.

13. The system of claim 1, further comprising:
a vagus nerve stimulator wirelessly connected to the processor; and,
wherein the set of instructions further cause the system to perform the step of:
  sending a signal to activate the vagus nerve stimulator based on at least one of the group of the ingress and the egress.

* * * * *